US012636307B2

(12) United States Patent
Glass et al.

(10) Patent No.: US 12,636,307 B2
(45) **Date of Patent: *May 26, 2026**

(54) IN VITRO HEPARIN AND HEPARAN SULFATE COMPOSITIONS AND METHODS OF MAKING AND USING

(71) Applicant: TEGA THERAPEUTICS, INC., San Diego, CA (US)

(72) Inventors: Charles Glass, San Diego, CA (US); Bryan Thacker, San Diego, CA (US); Jeffrey Esko, San Diego, CA (US)

(73) Assignee: TEGA THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/470,164

(22) PCT Filed: Dec. 15, 2017

(86) PCT No.: PCT/US2017/066860

§ 371 (c)(1),
(2) Date: Jun. 14, 2019

(87) PCT Pub. No.: WO2018/112434

PCT Pub. Date: Jun. 21, 2018

(65) Prior Publication Data

US 2020/0038430 A1 Feb. 6, 2020

Related U.S. Application Data

(60) Provisional application No. 62/435,633, filed on Dec. 16, 2016.

(51) Int. Cl.
*A61K 31/727* (2006.01)
*A61P 7/02* (2006.01)
*C08B 37/00* (2006.01)

(52) U.S. Cl.
CPC .............. *A61K 31/727* (2013.01); *A61P 7/02* (2018.01); *C08B 37/0075* (2013.01)

(58) Field of Classification Search
None
See application file for complete search history.

(56) References Cited

U.S. PATENT DOCUMENTS

| | | | |
|---|---|---|---|
| 4,421,650 A | 12/1983 | Nagasawa et al. | |
| 5,023,175 A | 6/1991 | Hosoya et al. | |
| 5,104,856 A | 4/1992 | Esko et al. | |
| 7,009,039 B2 | 3/2006 | Yayon et al. | |
| 2003/0139333 A1 | 7/2003 | Pawliuk et al. | |
| 2003/0190737 A1 | 10/2003 | Pecker et al. | |
| 2008/0146522 A1* | 6/2008 | Coombe | A61P 31/12 514/56 |
| 2009/0163435 A1 | 6/2009 | Bader et al. | |
| 2011/0165132 A1 | 7/2011 | Cool et al. | |
| 2011/0244520 A1 | 10/2011 | Doherty et al. | |
| 2011/0281817 A1 | 11/2011 | Nielsen et al. | |
| 2012/0230964 A1* | 9/2012 | Cool | C08B 37/0075 424/93.7 |
| 2012/0295890 A1 | 11/2012 | Crawford et al. | |
| 2012/0301471 A1 | 11/2012 | Kobayashi et al. | |
| 2014/0298497 A1 | 10/2014 | Arock et al. | |
| 2017/0119820 A1 | 5/2017 | Moriarity et al. | |
| 2017/0204362 A1 | 7/2017 | Holman et al. | |
| 2020/0332088 A1 | 10/2020 | Glass et al. | |
| 2022/0305049 A1 | 9/2022 | Glass et al. | |
| 2024/0026404 A1 | 1/2024 | Glass et al. | |
| 2024/0301092 A1 | 9/2024 | Thacker et al. | |

FOREIGN PATENT DOCUMENTS

| | | | |
|---|---|---|---|
| EP | 0144019 A2 | 6/1985 | |
| WO | WO-9014418 A1 * | 11/1990 | C07K 16/18 |
| WO | WO-9106303 A1 | 5/1991 | |
| WO | WO-2004050673 A2 | 6/2004 | |
| WO | WO-2007083274 A1 | 7/2007 | |
| WO | WO-2008116889 A1 | 10/2008 | |
| WO | WO-2011153458 A2 | 12/2011 | |
| WO | WO-2014185858 A1 * | 11/2014 | A61K 31/727 |
| WO | WO-2016091268 A2 | 6/2016 | |
| WO | WO-2016172766 A1 | 11/2016 | |
| WO | WO-2017106782 A1 | 6/2017 | |
| WO | WO-2018112434 A1 | 6/2018 | |
| WO | WO-2021041711 A1 | 3/2021 | |
| WO | WO-2023278631 A1 | 1/2023 | |

OTHER PUBLICATIONS

Ledin et al. "Heparan sulfate structure in mice with genetically modified heparan sulfate production." Journal of Biological Chemistry 279.41 (2004): 42732-42741. (Year: 2004).*
Sugahara et al. "Heparin and heparan sulfate biosynthesis." IUBMB life 54.4 (2002): 163-175. (Year: 2002).*
Oldberg et al. "Cell-surface heparan sulfate. Isolation and characterization of a proteoglycan from rat liver membranes." Journal of Biological Chemistry 254.17 (1979): 8505-8510. (Year: 1979).*
Merry et al. "The Molecular Phenotype of Heparan Sulfate in theHs2st-/- Mutant Mouse." Journal of Biological Chemistry 276. 38 (2001): 35429-35434. (Year: 2001).*
Pan et al. "Functional abnormalities of heparan sulfate in mucopolysaccharidosis-I are associated with defective biologic activity of FGF-2 on human multipotent progenitor cells." Blood 106.6 (2005): 1956-1964. (Year: 2005).*
Pempe et al. "Substrate specificity of 6-O-endosulfatase (Sulf-2) and its implications in synthesizing anticoagulant heparan sulfate." Glycobiology 22.10 (2012): 1353-1362 (Year: 2012).*
Gasimili et al. Bioengineering murine mastocytoma cells to produce anticoagulant heparin. Glycobiology 24(3):272-280 (2013).
Glass. Recombinant Heparin-New Opportunities. Frontiers in Medicine 5(341):1-14 (2018).
Hernaiz et al. Purification and characterization of heparan sulfate peptidoglycan from bovine liver. Carbohydrate Polymers 28:153-160 (2002).
Ledin et al. Heparan sulfate structure in mice with genetically modified heparan sulfate production. J Biol Chem 279:42732-41 (2004).

(Continued)

*Primary Examiner* — Emily A Cordas
(74) *Attorney, Agent, or Firm* — WILSON SONSINI GOODRICH & ROSATI

(57) ABSTRACT

Disclosed herein are cellular derived heparin and heparan sulfate compositions, methods of making and using, and cell lines for making and using.

8 Claims, 9 Drawing Sheets

(56) References Cited

OTHER PUBLICATIONS

Montgomery et al. Stable heparin-producing cell lines derived from the Furth murine mastocytoma. PNAS USA 89(23):11327-11331 (1992).
Pan et al. Functional abnormalities of heparan sulfate in mucopolysaccharidosis-I are associated with defective biologic activity of FGF-2 on human multipotent progenitor cells. Blood 106(6):1956-1964 (2005).
PCT/US2020/048243 International Search Report and Written Opinion dated Feb. 5, 2021.
Shimada et al. Novel heparan sulfate assay by using automated high-throughput mass spectrometry: Application to monitoring and screening for mucopolysaccharidoses. Molecular Genetics and Metabolism 113(Iss. 1-2):92-99 (2014).
U.S. Appl. No. 16/063,670 Office Action dated Feb. 11, 2021.
Zcharia et al. Transgenic expression of mammalian heparanase uncovers physiological functions of heparan sulfate in tissue morphogenesis, vascularization, and feeding behavior. FASEB J 18(2):252-63 (2004).
PCT/US2020/048243 Invitation to Pay Additional Fees dated Dec. 2, 2020.
PCT/US2016/067373 International Search Report and Written Opinion dated Mar. 9, 2017.
PCT/US2017/066860 International Search Report and Written Opinion dated Apr. 25, 2018.
Saksela et al. Endothelial cell-derived heparan sulfate binds basic fibroblast growth factor and protects it from proteolytic degradation. J Cell Biol 107(2):743-751 (1988).
Vieira et al. Acharan sulfate, the new glycosaminoglycan from Achatina fulica Bowdich 1822. Structural heterogeneity, metabolic labeling and localization in the body, mucus and the organic shell matrix. Eur J Biochem. 271(4):845-54 (2004).
Galvis et al.: Transgenic or tumor-induced expression of heparanase upregulates sulfation of heparan sulfate. Nat Chem Biol. 3(12):773-778 (2007).
Holmborn et al.: Heparan sulfate synthesized by mouse embryonic stem cells deficient in NDST1 and NDST2 is 6-O-sulfated but contains no N-sulfate groups. J Biol Chem. 279(41):42355-42358 doi:10.1074/jbc.C400373200 (2004).
Jozaki et al.: Proliferative potential of murine peritoneal mast cells after degranulation induced by compound 48/80, substance P, tetradecanoylphorbol acetate, or calcium ionophore A23187. J Immunol 145(12):4252-4256 (1990).
Tian et al.: Loss of CHSY1, a secreted Fringe enzyme, causes syndromic brachydactyly in humans via increased Notch signaling. Am J Hum Genet. 87(6):768-778 doi:10.1016/j.ajhg.2010.11.005 (2010).
U.S. Appl. No. 16/063,670 Final Office Action mailed Jul. 7, 2021.
U.S. Appl. No. 16/063,670 Non-Final Office Action dated Dec. 29, 2021.
Anders Dagälv, et al. Lowered Expression of Heparan Sulfate/Heparin Biosynthesis Enzyme N-Deacetylase/N-Slfotransferase 1 Results in Increased Sulfation of Mast Cell Heparin. Journal of Biological Chemistry. vol. 286. No. 52 (2011): pp. 44433-44440.
Fuster, Mark M., et al. Genetic Alteration of Endothelial Heparan Sulfate Selectively Inhibits Tumor Angiogenesis. The Journal of Cell Biology. vol. 177, Issue No. 3 (2007): pp. 539-549.
Deanna G Wilson, et al. Chondroitin Sulfate Synthase 1 (Chsy1) is Required for Bone Development and Digit Patterning. Developmental Biology. vol. 363, Issue No. 2 (2012): pp. 413-425.
EP20858364.1 Extended European Search Report dated Oct. 10, 2023.
Forsberg E, et al. Abnormal Mast Cells in Mice Deficient in a Heparin Synthesizing Enzyme. Nature. vol. 400, No. 6746 (1999): pp. 773-776.
Gasimli, Leyla et al. Bioengineering murine mastocytoma cells to produce anticoagulant heparin. Glycobiology vol. 24,3 (2014): 272-80. doi:10.1093/glycob/cwt108.
Jong Youn Baik, et al. Toward a Bioengineered Heparin: Challenges and Strategies for Metabolic Engineering of Mammalian Cells. Bioengineered. vol. 3, Issue No. 4 (2012): pp. 227-231.
Judith Habicher, et al. Glycosaminoglycan Biosynthesis and Function in Zebrafish Development. Sugars Shaping Skeletons. (2015): 60 Pages.
Holmborn, Katarina et al. On the Roles and Regulation of Chondroitin Sulfate and Heparan Sulfate in Zebrafish Pharyngeal Cartilage Morphogenesis. Journal of Biological Chemistry. vol. 287, No. 40, (2012): pp. 33905-33916.
Stickens Dominique, et al. Mice Deficient in Ext2 Lack Heparan Sulfate and Develop Exostoses. Development. vol. 132, No. 22 (2005): pp. 5055-5068.
Esko. Special Considerations for Proteoglycans and Glycosaminoglycans and Their Purification. Curr Protoc Mol Biol Chapter 17:Unit17.2. 1-17.2.9 (2000).
Baik, Jong Youn. et al. Metabolic Engineering of Chinese Hamster Ovary Cells: Towards a Bioengineered Heparin. Metabolic Engineering 14(2):81-90 (2012).
Bashkin, Pnina. et al. Degranulating mast cells secrete an endoglycosidase that degrades heparan sulfate in subendothelial extracellular matrix. Blood 75(11):2204-2212 (1990).
Datta, Payel. et al. Bioengineered Chinese Hamster Ovary Cells With Golgi-targeted 3-O-sulfotransferase-1 Biosynthesize Heparan Sulfate With an Antithrombin-binding Site. Journal of Biological Chemistry 288(52):37308-37318 (2013).
Chica, et al. Semi-rational approaches to engineering enzyme activity: combining the benefits of directed evolution and rational design. Curr Opin Biotechnol 16(4):378-384 (2005).
Kizer, Lance et al. Application of functional genomics to pathway optimization for increased isoprenoid production. Applied and environmental microbiology 74(10):3229-3241 (2008).
Morimoto-Tomita, Megumi et al. Cloning and characterization of two extracellular heparin-degrading endosulfatases in mice and humans. Journal of Biological Chemistry 277(51):49175-49185 (2002).
Prather, Kristala L. Jones, and Collin H. Martin. De novo biosynthetic pathways: rational design of microbial chemical factories. Current opinion in biotechnology 19(5):468-474 (2008).
Singh, Raushan Kumar et al. Protein Engineering Approaches in the Post-Genomic Era. Current Protein and Peptide Science 18:1-11 (2017).

* cited by examiner

IN VITRO HEPARIN AND HEPARAN SULFATE COMPOSITIONS AND METHODS OF MAKING AND USING

CROSS-REFERENCE

This patent application is a U.S. National Stage Entry of International Application No. PCT/US2017/066860, filed Dec. 15, 2017, which claims the benefit of U.S. Provisional Patent Application No. 62/435,633, filed Dec. 16, 2016, which are incorporated herein by reference in their entireties.

BACKGROUND

Heparin and heparan sulfate are useful for their anticoagulant properties. Sourcing heparin and heparan sulfate anticoagulants is dependent, in part, on animal tissues from slaughtered animals, such as pigs and cows. Animal sources of heparin and heparan sulfate pose potential safety risks that could be addressed via synthetic heparin and heparan sulfate. However, synthetic heparin and heparan sulfate have proven expensive and difficult to prepare in amounts sufficient for pharmaceutical use.

SUMMARY OF THE INVENTION

Provided herein are compositions comprising heparin, wherein the composition is at least 99.5% free of chondroitin sulfate. In some embodiments, the heparin composition comprises a heparin purified from a genetically modified cell line. In some embodiments, the composition is purified from a cell line genetically modified to be deficient for one or more genes recited in Table 6. In some embodiments, the composition is purified from a cell line genetically modified to be deficient for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 μlucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM 147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328 In some embodiments, the composition is purified from a cell line genetically modified to be deficient for chondroitin sulfate synthase 1 (ChSy). In some embodiments, the composition is purified from cells that do not produce chondroitin sulfate. In some embodiments, the composition is purified from a cell line genetically modified to be transgenic for one or more genes recited in Table 6. In some embodiments, the composition is purified from a cell line genetically modified to be transgenic for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (579639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 μlucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). In some embodiments, the composition is purified from a cell line genetically modified to be deficient for chondroitin sulfate synthesis (ChA27) and transgenic for Hs3st1. In some embodiments, composition comprises a heparin with a defined pattern of sulfation. In some embodiments, the composition is at least 95% free of protein and nucleic acid contamination. In some embodiments, the composition is at least 95% heparin. In some embodiments, the cell line comprises a cell line in Table 4.

Also provided herein are pharmaceutical compositions comprising any one or the above the composition according to any one of the above embodiments and a pharmaceutically acceptable carrier or excipient.

Further provided herein are compositions comprising heparan sulfate, wherein the composition is at least 99.5% free of chondroitin sulfate. In some embodiments, the composition comprises a hyper-sulfated heparan sulfate. In some embodiments, the heparan sulfate is purified from a genetically modified cell line. In some embodiments, the composition is purified from a cell line genetically modified to be deficient for one or more genes recited in Table 6. In some embodiments, the composition is purified from a cell line genetically modified to be deficient for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 μlucuronyl epimerase (CSEPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM 147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). In some embodiments, the composition is purified from a cell line genetically modified to be deficient for chondroitin sulfate synthase 1 (ChSy). In some embodiments, the composition is purified from cells that do not produce chondroitin sulfate. In some embodiments, the composition is purified from a cell line genetically modified to be transgenic for one or more genes recited in Table 6. In some embodiments, the composition is purified from a cell line genetically modified to be transgenic for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (579639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 μlucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6

(HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). In some embodiments, the composition is purified from a cell line genetically modified to be deficient for chondroitin sulfate synthesis (ChA27) and transgenic for Hs3st1. In some embodiments, the composition comprises a hypersulfated heparan sulfate with a defined pattern of sulfation. In some embodiments, the composition is at least 95% free of protein and nucleic acid contamination. In some embodiments, the composition is at least 95% heparan sulfate. In some embodiments, the cell line comprises a cell line in Table 3.

Also provided herein are pharmaceutical compositions comprising any one of the compositions according to of any one of the above embodiments and a pharmaceutically acceptable carrier or excipient.

Further provided herein are compositions comprising a cell deficient in one or more genes recited in Table 6. In some embodiments, the cell is deficient in one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 μlucuronyl epimerase (CSEPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). In some embodiments, the cell is deficient in chondroitin sulfate synthase 1 (ChSy1). In some embodiments, the cell is deficient in chondroitin sulfate. In some embodiments, the cell is transgenic for one or more genes recited in Table 6. In some embodiments, the cell is transgenic for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 μlucuronyl epimerase (CSEPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). In some embodiments, the cell is genetically modified to be deficient for chondroitin sulfate synthesis (ChA27) and transgenic for Hs3st1. In some embodiments, the cell comprises a cell line in Table 4. In some embodiments, the cell produces a heparin composition substantially free from chondroitin sulfate. In some embodiments, the cell produces a heparin with a defined pattern of sulfation. In some embodiments, the cell produces a heparin that is at least 95% free from protein and nucleic acid contamination. In some embodiments, the cell produces a hyper-sulfated heparan sulfate composition substantially free from chondroitin sulfate. In some embodiments, the cell produces a hyper-sulfated heparan sulfate with a defined pattern of sulfation. In some embodiments, the cell produces a hyper-sulfated heparan sulfate that is at least 95% free from protein and nucleic acid contamination. In some embodiments, the cell is a mast cell, a CHO cell, a mouse embryonic fibroblast, a 293 cell, a HeLa cell, a human fibroblast, a human embryonic stem cell, a stem cell, a an F9 cell, a human cardiac-derived progenitor cell (hCMPC), a tumor cell, or other animal cell. In some embodiments, the cell is from a mammal. In some embodiments, the cell is from a human.

Also provided herein are methods of preparation of a substantially pure heparin or hyper-sulfated heparan sulfate comprising use of any of the compositions according to any one of the above embodiments, wherein the method comprises the steps: (a) growing any of the cells according to any one of the above embodiments, using an appropriate growth media, (b) isolating the growth media from the cells by centrifugation. In some embodiments, the method comprises fractionating the mixture by ion exchange column. In some embodiments, the method comprises removing contaminating nucleic acids by nuclease digestion. In some embodiments, the method comprises removing contaminating proteins by protease digestion. In some embodiments, the method comprises fractionating the resulting product by ion exchange. In some embodiments, the method comprises affinity chromatography. In some embodiments, the method comprises desalting. In some embodiments, the heparin or hyper-sulfated heparan sulfate is substantially free from chondroitin sulfate. In some embodiments, the method does not require the use of a chondroitinase. In some embodiments, the heparin or hyper-sulfated heparan sulfate is at least 95% free from protein and nucleic acid contamination.

Also provided herein are methods of making a cell line capable of producing a heparin or a hyper-sulfated heparan sulfate comprising genetically modifying a cell line to be transgenic or deficient for a gene of Table 6. In some embodiments, the cell line does not produce chondroitin sulfate.

Also provided herein are kits comprising any cell according to any of the above embodiments and instructions for use in preparing a cell-line produced heparin. In some embodiments, the kit comprises instructions for any method according to any of the above embodiments.

Also provided herein are methods of treating a thrombosis in an individual in need thereof comprising administering an effective amount of any composition according to any of the above embodiments or a pharmaceutical composition thereof. In some embodiments, the thrombosis comprises, venous thrombosis, deep vein thrombosis, portal vein thrombosis, renal vein thrombosis, jugular vein thrombosis, Budd-Chiari syndrome, Paget-Schroetter disease, Cerebral venous sinus thrombosis, Cavernous sinus thrombosis, arterial thrombosis, stroke, myocardial infarction or Hepatic artery thrombosis.

Further provided herein are compositions according to any the above embodiments or pharmaceutical compositions thereof for use in treating a thrombosis.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
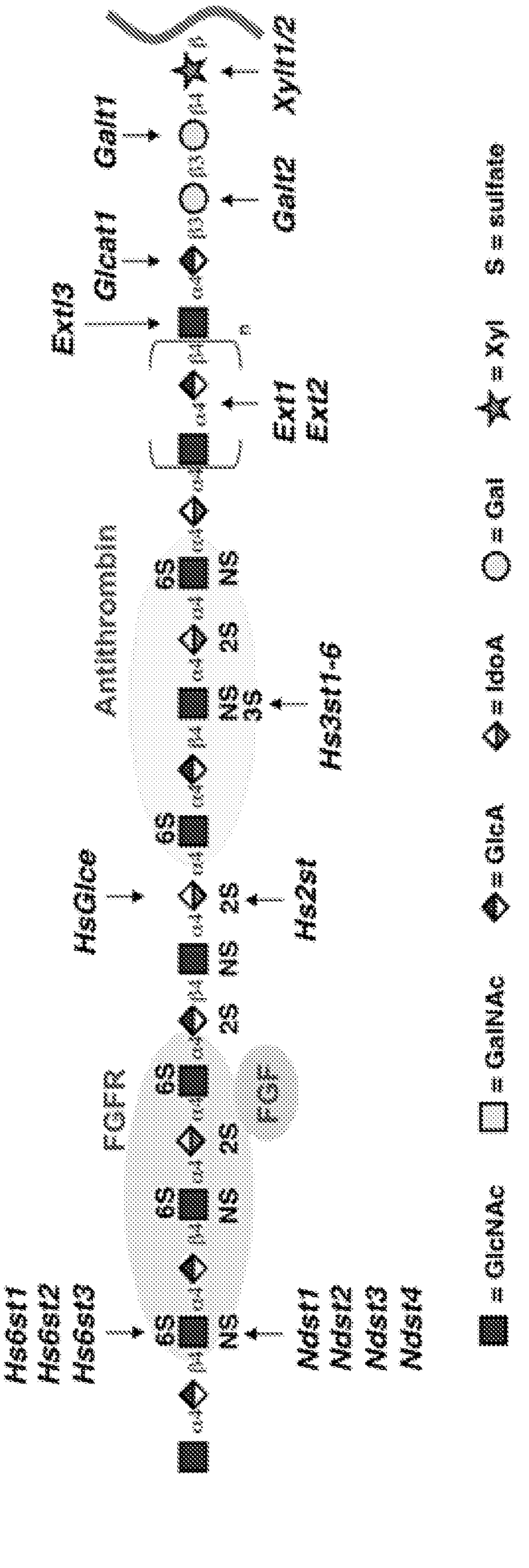
FIG. 1 shows a schematic of a heparin or heparan sulfate (HS) chain illustrating binding sites for antithrombin and FGF/FGFR. The various genes required for heparin or HS biosynthesis are indicated in italics. Xylt, xylosyltransferase; Galt, galactosyltransferase; Ext, exostosins, GlcNAc and GlcA transferases; Ndst, GlcNAc N-deacetylase/N-sulfotransferase; Hs6st, glucosaminyl 6-O-sulfotransferase; Hs3st, glucosaminyl 3-O-sulfotransferae; Hs2st, uronyl 2-O-sulfotransferase; HsGlce, uronyl C5 epimerase.

Glycosaminoglycans (GAGs) display heterogeneity in mass, disaccharide composition and pattern of sulfation which originates in their synthesis by cellular enzymes. GAGs are classified into four groups based on their core disaccharide structure: heparin, heparan sulfate (HS), chondroitin sulfate (CS), keratan sulfate (KS) and hyaluronic acid (HA). Proteins are further modified (i.e., glycosylated) in the cell with various diverse GAGs thereby creating proteoglycans. Purification and isolation of separate groups of glycosaminoglycans has proven challenging due to the heterogeneity of these compounds. Methods, systems and compositions are needed to provide adequate isolated and purified sources of glycosaminoglycans, including heparin and heparan sulfate.

Disclosed herein are GAGs purified from genetically modified cells that comprise uniform compositions of at least one specific GAG that is substantially free from one or more contaminating GAGs. In some embodiments, the composition is a heparin that is substantially free of contamination from one or more GAGs selected from a chondroitin sulfate, a keratan sulfate and a hyaluronic acid. In some embodiments, the composition is a heparan sulfate that is substantially free of contamination from one or more GAGs selected from a chondroitin sulfate, a keratan sulfate and a hyaluronic acid. In some embodiments, the composition is a chondroitin sulfate that is substantially free of contamination from one or more GAGs selected from a heparan sulfate, a keratan sulfate and a hyaluronic acid. In some embodiments, the composition is a keratan sulfate that is substantially free of contamination from one or more GAGs selected from a heparan sulfate, a chondroitin sulfate, and a hyaluronic acid. In some embodiments, the composition is a hyaluronic acid that is substantially free of contamination from one or more GAGs selected from a heparan sulfate, a chondroitin sulfate and a keratan sulfate.

GAGs are modified from their core disaccharide chain to create diversity within each type of GAG. Modifications include sulfation, deacetylation, and epimerization. Also disclosed herein are GAGs that comprise a specific GAG with a defined pattern of sulfation. In some embodiments the GAG comprises one or more of a GAG selected from a heparin, a heparan sulfate, a chondroitin sulfate, a keratan sulfate, and a hyaluronic acid each of which has a defined pattern of sulfation. In some embodiments the GAG comprises one or more of a GAG selected from a heparin, a heparan sulfate, a chondroitin sulfate, a keratan sulfate and a hyaluronic acid each of which has a defined pattern of epimerization. In some embodiments, the GAG is a heparin with a defined pattern of sulfation. In some embodiments the GAG is a heparan sulfate with a defined pattern of sulfation. In some embodiments, the GAG is a heparin with a defined pattern of epimerization. In some embodiments, the GAG is a heparan sulfate with a defined pattern of epimerization.

Heparin Compositions

Heparin is a highly sulfated glycosaminoglycan, occurring in nature as a polymer of varying chain size. Heparin is stored within secretory granules of mast cells and released into vascular sites during tissue injury. It is thought that heparin acts as a defense against invading pathogens in injured tissues. Pharmaceutical heparin includes unfractionated heparin, which has not been fractionated based on molecular weight, and low molecular weight heparin that has been fractionated. Low molecular weight heparin, in some embodiments, has more predictable pharmacodynamics when administered.

Heparin differs from heparan sulfate in several attributes (Table 1) including a higher degree of GlcNAc N-deacetylation and N-sulfation, content of IdoA and enhanced 2-O-sulfation and 6-O-sulfation. In addition it has greater anticoagulant activity due to its enhanced binding to antithrombin mediated by a pentasaccharide sequence rarely found in heparan sulfate (GlcNAc/NS6S-GlcA-GlcNS3S+6S-IdoA2S-GlcNS6S).

TABLE 1

Properties of heparin and heparan sulfate

| Property | Heparan sulfate | Heparin |
|---|---|---|
| Sulfate/hexosamine | 0.8-1.8 | 1.8-2.4 |
| GlcN N-sulfates | 40-60% | ≥85% |
| IdoA content | 30-50% | ≥70% |
| Solubility in 2M KAc at pH 5.7, 4° C. | Yes | No |
| Site of synthesis | Virtually all cells | Mast cells |
| Size | 10-70 kDa | 10-12 kDa |
| Binding to Antithrombin | 0-0.3% | ~30% |

Diversity in heparin compositions or patterns of modification is introduced into short oligomeric regions along the heparin molecule via modifications. In some embodiments, these modifications create specific protein binding sites on heparin. In some embodiments, the modifications include adding sulfate groups to four positions (N, 20, 30, and/or 60) on carbohydrate residues within the disaccharides and epimerization of glucuronic acid residues to create iduronic acid. In yet other embodiments, these modifications do not run to completion, thereby creating heparin that contains a wide variety of oligomeric structures. In some cases, specific protein binding to oligosaccharides on heparin is determined by the degree and pattern of sulfation within the oligosaccharide.

Heparin is composed of linear chains of repeating disaccharides (glucuronic acid beta 1-4 μlinked to N-acetylglucosamine) that are polydisperse ranging from 3 to 30 kDa with an average molecular weight of 12 to 15 kDa. Certain positions in the sugar residues can be modified including N-deacetylation or N-deacetylation and N-sulfation at position C2 of N-acetylglucosamine residues resulting in glucosamine or N-sulfated glucosamine. Glucosamine residues can also be 0-sulfated at positions 3 and 6 although 3-O-sulfation prevalent in pharmaceutical heparin. The C2 position of glucuronic acid can be 0-sulfated although this is much more common upon prior epimerization of glucuronic acid to iduronic acid. Epimerization also changes the linkage between the iduronic acid and the subsequent residue from beta 1-4 to alpha 1-4 and this modification is also prevalent in heparin. Heparin consists of up to 70-80 disaccharide units where the disaccharide units are modified to varying degrees throughout the disaccharide chains. Particular subregions of the chains are highly sulfated where as other regions are moderately sulfated or unsulfated. The rules governing the overall level and pattern of these modifications are not well understood however O-sulfation and epimerization typically follow N-sulfation.

Provided in certain embodiments herein are heparin compositions with patterns of modification derived from cell lines capable of heparin biosynthesis. In various embodiments, heparin biosynthesis, as used herein, includes, by way of non-limiting example, (1) increasing or decreasing in cell lines via genetic modification (a) heparin polymerization; (b) heparin sulfation; (c) epimerization of uronic acid groups in heparin; (d) heparin phosphorylation and/or (e) deacetylation of GlcNAc groups in heparin; and/or (2) promotion of (a) heparin bond cleavage; (b) bond cleavage of the linker region connecting heparin to a core protein; (c) bond cleavage between heparin and the linker region; (d) sulfation (e.g., N-sulfation and/or O-sulfation) of heparin; (e) acetylation of GlcN groups in heparin; (f) deacetylation of GlcNAc groups in heparin; (g) heparin phosphorylation, and/or (h) epimerization of uronic acid groups in heparin. In specific embodiments, the genetic modification of cell lines inhibits sulfation of heparin. In specific embodiments, the genetic modification of cell lines increases sulfation of heparin. In yet other embodiments, the genetic modification of cell lines inhibits epimerization of heparin. In specific embodiments, the genetic modification of cell lines increases epimerization of heparin.

In some embodiments, the heparin composition is derived from a cell line with a genetic modification that modulates (e.g., increases or inhibits) glycosyltransferases. In some embodiments, the heparin composition is derived from a cell line with a genetic modification that inhibits the synthesis of the linkage region suitable for connecting heparin to a core protein, the initiation of heparin synthesis, the synthesis of heparin, or a combination thereof. In some embodiments, the heparin composition is derived from a cell line with a genetic modification that modulates (e.g., increases or inhibits) one or more of a heparin xylosyltransferases, a heparin galactosyltransferase, a heparin glucuronosyltransferase, a heparin N-acetylglucosamine transferase, or combinations thereof. In more specific embodiments, the genetic modification of cell lines modulates (e.g., increases or inhibits) one or more of xylosyltransferase I, xylosyltransferase II, galactosyltransferase I, galactosyltransferase II, glucuronosyltransferase I, glucuronosyltransferase II, N-acetylglucosamine transferase I, N-acetylglucosamine transferase II, or a combination thereof.

In certain embodiments, the heparin composition is derived from a cell line with genetic modifications that modulate sulfation, specifically a cell line that is genetically modified for one or more sulfotransferase. In specific embodiments, the heparin composition is derived from a cell line that is genetically modified, by way of non-limiting example, to modulate (e.g., inhibit or increase) one or more of a heparin O-sulfotransferase, a heparin N-sulfotransferase, or a combination thereof. In more specific embodiments, the genetically modified cell line modulates (e.g., inhibits or increases) a heparin O-sulfotransferase such as, by way of non-limiting example, one or more of a 6-0 sulfotransferase (of a glucosamine group), a 3-0 sulfotransferase (of a glucosamine group), a 2-0 sulfotransferase (of a uronic acid moiety, e.g., glucuronic acid or iduronic acid), a 6-0 sulfotransferase (of a galactose in the linkage tetrasaccharide), or a combination thereof. In some embodiments, genetically modified cell lines modulate 2-0 phosphorylation of the xylose in the linkage tetrasaccharide.

In certain embodiments, the heparin composition is derived from a genetically modified cell line that alters or disrupts the nature (e.g., alters or disrupts the N-acetylation, N-sulfation, the 2-0 sulfation, the 3-0 sulfation, and the 6-0 sulfation content of heparin, epimerization of heparin, chain length of heparin, or a combination thereof) of heparin compared to endogenous heparin in an amount sufficient to create a heparin composition with altered or disrupted heparin binding of protein ligands, heparin-dependent signaling pathways, or a combination thereof. In specific embodiments, the genetically modified cell line alters the nature of the heparin such that it alters heparin signaling. In other specific embodiments, the genetically modified cell line alters the nature of the heparin such that it alters heparin binding to proteins. In more specific embodiments, the genetically modified cell line alters the nature of the heparin such that it alters heparin binding and heparin signaling. In some embodiments, the genetically modified cell line alters the nature of the heparin such that it alters the binding, signaling, or a combination thereof of any protein (including polypeptides) subject to heparin binding, signaling or a combination thereof, in the absence of a heparin inhibitor. In some embodiments, the heparin has altered anti-coagulant activity, such as increased anti-coagulant activity or decreased anti-coagulant activity compared to pharmaceutical preparations of heparin. In some embodiments, the heparin has similar anti-coagulant activity compared to pharmaceutical preparations of heparin. In some embodiments, the heparin has increased batch to batch consistency of anti-coagulant activity compared to pharmaceutical heparin. In some embodiments, the heparin has reduced contamination of pathogens and other proteoglycans than pharmaceutical preparations of heparin.

Although heparin-binding consensus sequences have been identified in some proteins, the mechanisms of binding are variable. From the standpoint of heparin, the degree of sulfation and the sulfation pattern can increase the affinity of short oligomeric regions for certain amino acid sequences (typically involving basic amino acids), both chemically (ionic) and geometrically.

Heparan Sulfate Compositions

Heparan sulfate plays important roles in cellular and tissue specific physiology, pathophysiology and development because heparan sulfate specifically binds to a wide variety of proteins. In some embodiments proteins include enzymes, extracellular signaling molecules, chemokines, lipid- or membrane-binding proteins, adhesion proteins and pathogenic proteins. In some embodiments, the heparan sulfate of the compositions and methods disclosed herein can be used to affect blood clotting, inflammatory processes, stem cell differentiation, normal and cancer cell growth and differentiation, blood cell differentiation, cell-cell and cell-matrix interactions, lipid transport and clearance/metabolism, host defense and viral and bacterial infection.

Diversity in heparan sulfate compositions or patterns of modification is introduced into short oligomeric regions along the heparan sulfate chains via modifications. In some embodiments, these modifications create specific protein binding sites on the heparan sulfate. In some embodiments, the modifications include adding sulfate groups to up to four positions on carbohydrate residues within the disaccharides and epimerization of glucuronic acid residues to create iduronic acid. In yet other embodiments, these modifications do not run to completion, thereby creating heparan sulfate chains that contain a wide variety of oligomeric structures. In some cases, specific protein binding to oligosaccharides on the heparan sulfate chains is determined by the degree and pattern of sulfation within the oligosaccharide.

Heparan sulfate is composed of linear chains of repeating disaccharides (glucuronic acid beta 1-4 µlinked to N-acetylglucosamine) that are polydisperse ranging from 5 to 50 kDa with an average molecular weight of 30 kDa. Certain positions in the sugar residues can be modified including N-deacetylation or N-deacetylation and N-sulfation at position C2 of N-acetylglucosamine residues resulting in glucosamine or N-sulfated glucosamine. Glucosamine residues can also be 0-sulfated at positions 3 and 6 although 3-O-sulfation is rare and much more prevalent in pharmaceutical heparin. The C2 position of glucuronic acid can be 0-sulfated although this is much more common upon prior epimerization of glucuronic acid to iduronic acid. Epimerization also changes the linkage between the iduronic acid and the subsequent residue from beta 1-4 to alpha 1-4 and this modification is also much more prevalent in heparin. Heparan sulfate consists of up to 100 disaccharide units where the disaccharide units are modified to varying degrees throughout the heparan sulfate chains. Particular sub-regions of the chains are highly sulfated where as other regions are moderately sulfated or unsulfated. The rules governing the overall level and pattern of these modifications are not well understood, however O-sulfation and epimerization typically follows N-sulfation.

Provided in certain embodiments herein are heparan sulfate compositions with patterns of modification derived from cell lines capable of heparan sulfate biosynthesis. In various embodiments, heparan sulfate biosynthesis, as used herein, includes, by way of non-limiting example, (1) increasing or decreasing in cell lines via genetic modification (a) heparan sulfate polymerization; (b) heparan sulfate sulfation; (c) epimerization of uronic acid groups in heparan sulfate; (d) heparan sulfate phosphorylation and/or (e) deacetylation of GlcNAc groups in heparan sulfate; and/or (2) promotion of (a) heparan sulfate bond cleavage; (b) bond cleavage of the linker region connecting heparan sulfate to a core protein; (c) bond cleavage between heparan sulfate and the linker region; (d) sulfation (e.g., N-sulfation and/or O-sulfation) of heparan sulfate; (e) acetylation of GlcN groups in heparan sulfate; (f) deacetylation of GlcNAc groups in heparan sulfate; (g) heparan sulfate phosphorylation, and/or (h) epimerization of uronic acid groups in heparan sulfate. In specific embodiments, the genetic modification of cell lines inhibits sulfation of heparan sulfate. In specific embodiments, the genetic modification of cell lines increases sulfation of heparan sulfate. In yet other embodiments, the genetic modification of cell lines inhibits epimerization of heparan sulfate. In specific embodiments, the genetic modification of cell lines increases epimerization of heparan sulfate.

In some embodiments, the heparan sulfate composition is derived from a cell line with a genetic modification that modulates (e.g., increases or inhibits) glycosyltransferases. In some embodiments, the heparan sulfate composition is derived from a cell line with a genetic modification that inhibits the synthesis of the linkage region suitable for connecting heparan sulfate to a core protein, the initiation of heparan sulfate synthesis, the synthesis of heparan sulfate, or a combination thereof. In some embodiments, the heparan sulfate composition is derived from a cell line with a genetic modification that modulates (e.g., increases or inhibits) one or more of a heparan sulfate xylosyltransferases, a heparan sulfate galactosyltransferase, a heparan sulfate glucuronosyltransferase, a heparan sulfate N-acetylglucosamine transferase, or combinations thereof. In more specific embodiments, the genetic modification of cell lines modulates (e.g., increases or inhibits) one or more of xylosyltransferase I, xylosyltransferase II, galactosyltransferase I, galactosyltransferase II, glucuronosyltransferase I, glucuronosyltransferase II, N-acetylglucosamine transferase I, N-acetylglucosamine transferase II, or a combination thereof.

In certain embodiments, the heparan sulfate composition is derived from a cell line with genetic modifications that modulate sulfation, specifically a cell line that is genetically modified for one or more sulfotransferase. In specific embodiments, the heparan sulfate composition is derived from a cell line that is genetically modified, by way of non-limiting example, to modulate (e.g., inhibit or increase) one or more of a heparan sulfate O-sulfotransferase, a heparan sulfate N-sulfotransferase, or a combination thereof. In more specific embodiments, the genetically modified cell line modulates (e.g., inhibits or increases) a heparan sulfate O-sulfotransferase such as, by way of non-limiting example, one or more of a 6-0 sulfotransferase (of a glucosamine group), a 3-0 sulfotransferase (of a glucosamine group), a 2-0 sulfotransferase (of a uronic acid moiety, e.g., glucuronic acid or iduronic acid), a 6-0 sulfotransferase (of a galactose in the linkage tetrasaccharide), or a combination thereof. In some embodiments, genetically modified cell lines modulate 2-0 phosphorylation of the xylose in the linkage tetrasaccharide. In some embodiments, the heparan sulfate composition is derived from a cell line that is genetically modified to increase sulfation of the heparan sulfate resulting in a heparan sulfate composition with hyper-sulfated or over-sulfated heparan sulfate.

In certain embodiments, the heparan sulfate composition is derived from a genetically modified cell line that alters or disrupts the nature (e.g., alters or disrupts the N-acetylation, N-sulfation, the 2-0 sulfation, the 3-0 sulfation, and the 6-0 sulfation content of heparan sulfate, epimerization of heparan sulfate, chain length of heparan sulfate, or a combination thereof) of heparan sulfate compared to endogenous heparan sulfate in an amount sufficient to create a heparan sulfate composition with altered or disrupted heparan sulfate binding of protein ligands, heparan sulfate-dependent signaling pathways, or a combination thereof. In specific embodiments, the genetically modified cell line alters the nature of the heparan sulfate such that it alters heparan sulfate signaling. In some embodiments, the composition comprises heparan sulfate with reduced 2-O-sulfation. In some embodiments, the composition comprises heparan sulfate with reduced 6-O-sulfation. In some embodiments, the composition comprises heparan sulfate with reduced 2-O-sulfation and reduced 6-O-sulfation. In other specific embodiments, the genetically modified cell line alters the nature of the heparan sulfate such that it alters heparan sulfate binding to proteins. In more specific embodiments, the genetically modified cell line alters the nature of the heparan sulfate such that it alters heparan sulfate binding and heparan sulfate signaling. In some embodiments the genetically modified cell line alters the nature of heparan sulfate such that it increases anti-coagulant activity. In some embodiments, the genetically modified cell line alters the nature of the heparan sulfate such that it alters the binding, signaling, or a combination thereof of any protein (including polypeptides) subject to heparan sulfate binding, signaling or a combination thereof, in the absence of a heparan sulfate inhibitor. In some embodiments, the protein is, by way of non-limiting example, a growth factor. In specific embodiments, the growth factor is, by way of non-limiting example, fibroblast growth factor (FGF) or vascular endothelia growth factor (VEGF). In some embodiments, the protein is, by way of non-limiting example, platelet factor 4 (PF4)

Although heparin-binding consensus sequences have been identified in some proteins, the mechanisms of binding are variable. From the standpoint of heparan sulfate, the degree of sulfation and the sulfation pattern can increase the affinity of short oligomeric regions for certain amino acid sequences (typically involving basic amino acids), both chemically (ionic) and geometrically.

Many of the functions ascribed to heparan sulfate have been deduced by binding and competition studies with pharmaceutical heparin, which is available in abundant quantities and can be broken down into fragments or chemically modified. However, heparin is a fractionated highly sulfated form of heparan sulfate derived from porcine or bovine entrails and has high antithrombin binding capacity and anticoagulant activity. The high degree of sulfation endows heparin with strong cation exchange properties and does not mimic naturally occurring heparan sulfate, which in some cases, has a much lower degree of sulfation and generally lacks anticoagulant activity. In some embodiments, heparan sulfate compositions herein comprise hypersulfated heparan sulfate with increased anticoagulant activity.

Cellular Production of Heparin

Although many animal cells make heparin, pharmaceutical heparin is purified from tissues of slaughtered cows and pigs. Sourcing heparin from animals introduces potential impurities, such as viruses, bacterial endotoxins, transmissible spongiform encephalopathy agents, lipids, proteins, and DNA. Further contamination occurs from contaminating proteoglycans, such as dermatan sulfate. Heparin from cultured cells displays the relevant size, disaccharide composition and distribution of sulfated domains similar to what is seen in animal tissues. Cellular expression facilitates the production of heparin in a reproducible manner at a scale appropriate for pharmaceutical production.

Heparin is synthesized and subsequently modified by over 23 enzymes and their isozymes in the heparin biosynthetic pathway. In turn, different heparin compositions in different cell types and tissues are the result of different expression patterns of the enzymes in the heparin biosynthetic pathway. Disclosed herein are methods and resultant compositions by engineering the composition of the cell surface and secreted heparin in cell cultures, for example mast cells or Chinese Hamster Ovary (CHO) cells, by altering the expression pattern of the biosynthetic enzymes by transfection or mutation. Accordingly, disclosed herein are cells engineered to produce heparin with reproducible composition, sulfation patterns and anti-coagulant properties. Further disclosed herein are methods of production of heparin having improved safety compared to heparin produced from animal tissues. Also disclosed herein are methods of production of gram scale of heparin compositions at decreased cost.

Described herein is the use of a cellular expression system to produce heparin in various compositions or defined sulfation patterns in a reproducible manner at a scale for pharmaceutical production. In some embodiments, the cellular expression system comprises a genetically modified cell from which a heparin composition with a defined pattern of sulfation is derived. In some embodiments, the genetically modified cell is deficient in one or more genes that encode an enzyme that modifies a heparin chain. In some embodiments the genetically modified cell is transgenic for one or more genes that encode an enzyme that modifies a heparin chain. In some embodiments, the gene encodes an enzyme that modifies a heparin chain selected from one or more of a sulfatase, an N-deacetylase, a synthase, an acetylgalactosaminyltransferase, a polymerizing factor, a sulphotransferase, an epimerase, an N-deacetylase/sulfotransferase, a sulfatase, a beta-glucuronidase, an iduronidase, a sulfamidase, an N-acetyltransferase, an N-acetylglucosaminidase, a xylosyltransferase, a galactosyltransferase, a glucuronyltransferase, a heparanase. In some embodiments, the gene encodes a proteoglycan core protein, such as any membrane proteoglycan (e.g., a glypican, a syndecan, or any secreted proteoglycan (e.g. serglycin, perlecan, collagen XVIII, or agrin). In some embodiments the gene is selected from DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 glucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)).

Disclosed herein are compositions comprising heparin derived from genetically modified cell lines. The genetically modified cell lines are cell lines comprising a population of cells. In some embodiments, the cells are selected from a 293T cell, a 3T3 cell, a 4T1 cell, a 721 cell, an 9L cell, an A2780 cell, an A2780ADR cell, an A2780cis cell, an A172 cell, an A20 cell, an A253 cell, an A431 cell, an A-549 cell, an ALC cell, a B16 cell, a B35 cell, a BCP-1 cell, a BEAS-2B cell, a bEnd.3 cell, a BHK-21 cell, a BR 293 cell, a BxPC3 cell, a C2C12 cell, a C3H-10T1/2 cell, a C6/36 cell, a C6 cell, a Cal-27 cell, a CGR8 cell, a CHO cell, a COR-L23 cell, a COR-L23/CPR cell, a COR-L23/5010 cell, a COR-L23/R23 cell, a COS-7 cell, a COV-434 cell, a CML T1 cell, a CMT cell, a CT26 cell, a D17 cell, a DH82 cell, a DU145 cell, a DuCaP cell, a E14Tg2a cell, a EL4 cell, a EM2 cell, a EM3 cell, a EMT6/AR1 cell, a EMT6/AR10.0 cell, a FM3 cell, a FMA-3 cell, a H1299 cell, a H69 cell, a HB54 cell, a HB55 cell, a HCA2 cell, a HEK-293 cell, a HeLa cell, a Hepalclc7 cell, a High Five cell, a HL-60 cell, a HMC-1 cell, a HMEpC cell, a HT-29 cell, a HUVEC cell, a Jurkat cell, a J558L cell, a JY cell, a K562 cell, a KBM-7 cell, a Ku812 cell, a KCL22 cell, a KG1 cell, a KYO1 cell, a LAD1 cell, a LAD2 cell, a LNCap cell, a LUVA cell, a Ma-Mel cell, a MC-38 cell, a MC/9 cell, a MCF-7 cell, a MCF-10A cell, a MDA-MB-231 cell, a MDA-MB-157 cell, a MDA-MB-361 cell, a MDCK II cell, a MG63 cell, a MOR/0.2R cell, a MONO-MAC 6 cell, a MRC5 cell, a MTD-1A cell, a MyEnd cell, a NCI-H69/CPR cell, a NCI-H69/LX10 cell, a NCI-H69/LX20 cell, a NCI-H69/LX4 cell, a NIH-3T3 cell, a NALM-1 cell, a NW-145 cell, a OPCN/OPCT cell, a P815 cell, a Peer cell, a PNT-1A/PNT 2 cell, a PTK2 cell, a Raji cell, a RBL cell, a RBL-1 cell, a RBL-2H3 cell, a RenCa cell, a RIN-5F cell, a RMA/RMAS cell, a S2 cell, a Saos-2 cell, a Sf21 cell, a Sf9 cell, a SiHa cell, a SKBR3 cell, a SKOV-3 cell, a T2 cell, a T-47D cell, a T84 cell, a U373 cell, a U87 cell, a U937 cell, a VCaP cell, a Vero cell, a WM39 cell, a WT-49 cell, a X63 cell, a YAC-1 cell, a YAR cell, or other animal cell described in the ATCC catalog. In some cases, the cell is an animal cell. In some cases, the cell is a mammalian cell. In some cases, the cell is a mouse cell, a rat cell, a non-human primate cell, or a human cell. In some cases, the cell is a mast cell. In some cases, the cell is a CHO cell.

The genetically modified cell lines are created by methods including but not limited to RNAi; CRISPR/Cas; transgenic cells; cells from transgenic animals; cells from knockout animals; transfection with plasmid; or infection with retrovirus, adenovirus, adeno-associated virus or lentivirus.

In some cases, the genetically modified cell lines are genetically deficient in one or more genes, or one or more target genes. Cell lines that are genetically deficient are made by multiple techniques known by those of skill in the art. In some cases, the cells are transformed or transfected with a plasmid or virus that expresses an RNAi or shRNA that reduces or eliminates expression of the targeted gene. In some cases, the cells are transfected with a double stranded siRNA that reduces or eliminates expression of the targeted gene. In some cases, the genetically modified cell line is created when the target gene is eliminated from the genome of the cell line using the CRISPR/Cas system. In some cases, the cell line is derived from a genetically modified animal that is deficient for the targeted gene or a knockout animal.

In some cases, the genetically modified cell lines are transgenic for one or more genes, or one or more target genes. Transgenic cell lines are made by multiple techniques known by those of skill in the art. In some cases, the cells are transformed or transfected with a plasmid or virus that expresses the gene. In some cases, the cells are infected with a virus, such as a retrovirus, lentivirus, adenovirus, adeno-associated virus, or other virus that infects animal cell, that expresses the target gene. In some cases, the transgene replaces the endogenous gene in the cell line creating a "knock-in" cell line. In some cases, CRISPR/Cas technology is used to create a "knock-in" cell line. In some cases, the transgenic cells are derived from an animal that is transgenic for the target gene.

Also described herein are research compositions used in biomedical and pharmaceutical research. In some cases, research compositions include but are not limited to extracellular matrix, microarrays, libraries of structures in 96-well plates, ligand-binding assays, ligand binding competition assays, in vitro and in vivo biological experiments. In some cases, extracellular matrix compositions are used for culture of cells.

Cellular Production of Heparan Sulfate

Although all animal cells make heparan sulfate, the size, composition, disaccharide composition and distribution of the sulfated domains vary significantly. The different arrangements of the disaccharide subunits and the sulfated domains are important, because they determine the protein ligand binding characteristics and therefore the biological properties of the chains. Heparan sulfate from cultured cells displays the relevant size, disaccharide composition and distribution of sulfated domains similar to what is seen in animal tissues. Cellular expression facilitates the production of heparan sulfate in a reproducible manner at a scale that will allow investigators to examine the biological properties of heparan sulfate and to fractionate and identify biologically relevant sequences, which can then serve as models for synthesis of biologically relevant oligosaccharides. In some embodiments, methods of heparan sulfate production provided herein produce heparan sulfate with less than 10% batch-to-batch variation.

Cell surface and extracellular matrix heparan sulfate structures vary widely but reproducibly in tissue, development stage, and pathophysiologic specific manners. The heparan sulfate chains are synthesized and subsequently modified by over 25 specific enzymes in the heparan sulfate biosynthetic pathway (FIG. 1). In turn, the different heparan sulfate compositions in different cell types and tissues are the result of different expression patterns of the enzymes in the heparan sulfate biosynthetic pathway. Disclosed herein are methods and resultant compositions by engineering the composition of the cell surface and secreted heparan sulfate chains in cell cultures, for example Chinese Hamster Ovary (CHO) cells, by altering the expression pattern of the biosynthetic enzymes by transfection or mutation. Accordingly, disclosed herein are cells engineered to produce heparan sulfate with reproducible composition, sulfation patterns and ligand binding properties. Also disclosed herein are methods of production of gram scale of heparan sulfate compositions at decreased cost.

Described herein is the use of a cellular expression system to produce heparan sulfate in various compositions or defined sulfation patterns in a reproducible manner at a scale that will allow investigators to examine the biological properties of heparan sulfate. In some embodiments, the cellular expression system comprises a genetically modified cell from which a heparan sulfate composition with a defined pattern of sulfation is derived. In some embodiments, the genetically modified cell is deficient in one or more genes that encode an enzyme that modifies a heparan sulfate chain. In some embodiments the genetically modified cell is transgenic for one or more genes that encode an enzyme that modifies a heparan sulfate chain. In some embodiments, the gene encodes an enzyme that modifies a heparan sulfate chain selected from one or more of a sulfatase, an N-deacetylase, a synthase, an acetylgalactosaminyltransferase, a polymerizing factor, a sulphotransferase, an epimerase, an N-deacetylase/sulfotransferase, a sulfatase, a beta-glucuronidase, an iduronidase, a sulfamidase, an N-acetyltransferase, an N-acetylglucosaminidase, a xylosyltransferase, a galactosyltransferase, a glucuronyltransferase, a heparanase. In some embodiments, the gene encodes a proteoglycan core protein, such as any membrane proteoglycan (e.g., a glypican, a syndecan, or any secreted proteoglycan (e.g. serglycin, perlecan, collagen XVIII, or agrin). In some embodiments the gene is selected from chondroitin sulfate synthase 1 or 3, (ChSy), chondroitin sulfate N-acetylgalactosaminyltransferase 2 (CSGalNAcT2), chondroitin polymerizing factor (ChPF), heparan sulfate 2-O-sulfotransferase (Hs2st), glucuronic acid epimerase (Glce), heparan sulfate N-deacetylase/sulfotransferase-1, 2, 3, or 4 (Ndst1-4), 6-O-sufotransferase 1,2,3 (Hs6st1-3), 3-O-sulfotransferasel, 2, 3, 4, 5, 6 (Hs3st1-6), sulfatase 1 (Sulf1), sulfatase 2 (Sulf2), beta-glucuronidase (Gusb), galactosamine-6 sulfatase (GalNs), alpha-L-iduronidase (Idua), sulfamidase (Sgsh), glucosamine N-acetyltransferase (HGSNAT,), uronate-2-sulfatase (Ids), alpha-N-acetylglucosaminidase (Naglu), PAPS synthase (PAPSS1, PAPSS2), xylosyltransferase 1 (Xylt1), xylosyltransferase 2 (Xylt2), galactosyltransferase 1 (B4galt1), galactosyltransferase 2 (B4galt2), glucuronyltransferase 1

(Glcatl), exostosin-like glycosyltransferase 3 (Ext13), exostosin glycosyltransferase 1 (Ext1), exostosin glycosyltransferase 2 (Ext2), heparanase (Hpse), glypican 1 (Gpc1), glypican 2 (Gpc2), lypican 3 (Gpc3), glypican 4 (Gpc4), glypican 5 (Gpc5), glypican 6 (Gpc6), syndecan 1 (Sdc1), syndecan 2 (Sdc2), syndecan 3 (Sdc3), syndecan 4 (Sdc4), betaglycan (Ggcan/Tgfbr3), cd44v3 (Cd44v3), neuropillin 1 (Nrpl), CD47 (Cd47), serglycin (Srgn), perlecan (plc), agrin (Agrn), and collagen 18 (Col18a1).

Disclosed herein are compositions comprising heparan sulfate derived from genetically modified cell lines. The genetically modified cell lines are cell lines comprising a population of cells. In some embodiments, the cells are selected from a 293T cell, a 3T3 cell, a 4T1 cell, a 721 cell, an 9L cell, an A2780 cell, an A2780ADR cell, an A2780cis cell, an A172 cell, an A20 cell, an A253 cell, an A431 cell, an A-549 cell, an ALC cell, a B16 cell, a B35 cell, a BCP-1 cell, a BEAS-2B cell, a bEnd.3 cell, a BHK-21 cell, a BR 293 cell, a BxPC3 cell, a C2C12 cell, a C3H-10T1/2 cell, a C6/36 cell, a C6 cell, a Cal-27 cell, a CGR8 cell, a CHO cell, a COR-L23 cell, a COR-L23/CPR cell, a COR-L23/5010 cell, a COR-L23/R23 cell, a COS-7 cell, a COV-434 cell, a CML T1 cell, a CMT cell, a CT26 cell, a D17 cell, a DH82 cell, a DU145 cell, a DuCaP cell, a E14Tg2a cell, a EL4 cell, a EM2 cell, a EM3 cell, a EMT6/AR1 cell, a EMT6/AR10.0 cell, a FM3 cell, a H1299 cell, a H69 cell, a HB54 cell, a HB55 cell, a HCA2 cell, a HEK-293 cell, a HeLa cell, a Hepalclc7 cell, a High Five cell, a HL-60 cell, a HMEpC cell, a HT-29 cell, a HUVEC cell, a Jurkat cell, a J558L cell, a JY cell, a K562 cell, a KBM-7 cell, a Ku812 cell, a KCL22 cell, a KG1 cell, a KYO1 cell, a LNCap cell, a Ma-Mel cell, a MC-38 cell, a MCF-7 cell, a MCF-10A cell, a MDA-MB-231 cell, a MDA-MB-157 cell, a MDA-MB-361 cell, a MDCK II cell, a MG63 cell, a MOR/0.2R cell, a MONO-MAC 6 cell, a MRC5 cell, a MTD-1A cell, a MyEnd cell, a NCI-H69/CPR cell, a NCI-H69/LX10 cell, a NCI-H69/LX20 cell, a NCI-H69/LX4 cell, a NIH-3T3 cell, a NALM-1 cell, a NW-145 cell, a OPCN/OPCT cell, a Peer cell, a PNT-1A/PNT 2 cell, a PTK2 cell, a Raji cell, a RBL cell, a RenCa cell, a RIN-5F cell, a RMA/RMAS cell, a S2 cell, a Saos-2 cell, a Sf21 cell, a Sf9 cell, a SiHa cell, a SKBR3 cell, a SKOV-3 cell, a T2 cell, a T-47D cell, a T84 cell, a U373 cell, a U87 cell, a U937 cell, a VCaP cell, a Vero cell, a WM39 cell, a WT-49 cell, a X63 cell, a YAC-1 cell, a YAR cell, or other animal cell described in the ATCC catalog. In some cases, the cell is an animal cell. In some cases, the cell is a mammalian cell. In some cases, the cell is a mouse cell, a rat cell, a non-human primate cell, or a human cell. In some cases, the cell is a mast cell.

The genetically modified cell lines are created by methods including but not limited to RNAi; CRISPR/Cas; transgenic cells; cells from transgenic animals; cells from knockout animals; transfection with plasmid; or infection with retrovirus, adenovirus, adeno-associated virus or lentivirus.

In some cases, the genetically modified cell lines are genetically deficient in one or more genes, or one or more target genes. Cell lines that are genetically deficient are made by multiple techniques known by those of skill in the art. In some cases, the cells are transformed or transfected with a plasmid or virus that expresses an RNAi or shRNA that reduces or eliminates expression of the targeted gene. In some cases, the cells are transfected with a double stranded siRNA that reduces or eliminates expression of the targeted gene. In some cases, the genetically modified cell line is created when the target gene is eliminated from the genome of the cell line using the CRISPR/Cas system. In some cases, the cell line is derived from a genetically modified animal that is deficient for the targeted gene or a knockout animal.

In some cases, the genetically modified cell lines are transgenic for one or more genes, or one or more target genes. Transgenic cell lines are made by multiple techniques known by those of skill in the art. In some cases, the cells are transformed or transfected with a plasmid or virus that expresses the gene. In some cases, the cells are infected with a virus, such as a retrovirus, lentivirus, adenovirus, adeno-associated virus, or other virus that infects animal cell, that expresses the target gene. In some cases, the transgene replaces the endogenous gene in the cell line creating a "knock-in" cell line. In some cases, CRISPR/Cas technology is used to create a "knock-in" cell line. In some cases, the transgenic cells are derived from an animal that is transgenic for the target gene.

Also described herein are research compositions used in biomedical and pharmaceutical research. In some cases, research compositions include but are not limited to extracellular matrix, microarrays, libraries of structures in 96-well plates, ligand-binding assays, ligand binding competition assays, intro and in vivo biological experiments. In some cases, extracellular matrix compositions are used for culture of cells.

Methods of Producing Heparin and Heparan Sulfate Compositions

Disclosed herein are heparin, and heparan sulfate compositions comprising defined patterns of sulfation derived from genetically modified cell lines described herein. Methods of purification of heparin, and heparan sulfate compositions from cultured cells are known by those of skill in the art. In some embodiments, the compositions are purified from the cell culture media. In some embodiments, the compositions are purified from lysed cells. In some embodiments, the compositions are purified using a chromatography column. In some embodiments, the compositions are purified using an ion exchange column such as an anion exchange column. In some embodiments, the compositions are purified using an affinity column. In some embodiments, the compositions are purified using a size exclusion column. In some embodiments, the compositions are purified from contaminating proteins and/or nucleic acids using enzymes such as a protease and/or a nuclease or enzymes that digest CS, HS or hyaluronic acid (HA). In some embodiments, the compositions are purified from contaminating salt using a size exclusion column. Cell lines can be grown under standard cell culture conditions with or without serum (preferably without). To increase production, different growth medias and additives can be used. To increase production, the cells can be grown in bioreactors of which there are different sizes and a number of different types including but not limited to vats, hollow fibers, and plastic disposable. Production in bioreactors can be increased by using different growth medias and additives as well as by adjusting growth condition parameters such as oxygen levels and pH. Purification methods for small and large scale production are similar but increased for larger scale with larger reagent volumes and/or column resin volumes.

In some embodiments, the processes described herein comprise further treatment steps to purify the heparin and/or heparan sulfate compositions. For example, in some embodiments, the heparin and/or heparan sulfate compositions are purified from a sample that is homogenized. In specific embodiments homogenization is achieved in any suitable manner including, by way of non-limiting example, with a basic solution (e.g., 0.1 N NaOH), sonication, tissue grinding, or other chemical agents.

In some embodiments, heparin and/or heparan sulfate compositions, described herein are purified using any suitable purification technique. In certain embodiments, purification techniques include electrophoresis, chromatography, column chromatography, gas chromatography, high performance liquid chromatography, thin layer chromatography, ion exchange chromatography, gel chromatography, molecular sieve chromatography, affinity chromatography, exclusion, filtration, precipitation, osmosis, recrystallization, fluorous phase purification, distillation, extraction, chromatofocusing, or the like.

In a non-limiting example, the cells or conditioned media comprising the heparin and/or heparan sulfate compositions are homogenized and solubilized in a basic or acidic composition, such as aqueous (e.g., 0.1-1.0 N, 0.1 N, 0.2 N, 0.3 N, 0.4 N, 0.5 N, 0.6 N, 0.7 N, 0.8 N, 0.9 N, or 1 N NaOH or acetic acid). The heparin and/or heparan sulfate is then optionally neutralized (e.g., with acetic acid or NaOH).

Next a small sample is taken to measure protein content of the heparin and/or heparan sulfate composition using standard methods. Optionally protease (e.g., 0.01-0.5 mg/mL, 0.01 mg/mL, 0.02 mg/mL, 0.03 mg/mL, 0.04 mg/mL, 0.05 mg/mL, 0.1 mg/mL, 0.14 mg/mL, 0.17 mg/mL, 0.2 mg/mL, 0.23 mg/mL, 0.25 mg/mL, 0.27 mg/mL, 0.3 mg/mL, 0.4 mg/mL, 0.5 mg/mL) (exemplary protease include, by way of non-limiting example, trypsin, chymotrypsin, pepsin, pronase, papain, or elastase) is added and the sample is treated in 0.1-0.5 M (e.g., e.g., 0.1 M, 0.16 M, 0.23 M, 0.32 M, 0.39 M, 0.44 M, or 0.5 M) NaCl, 0.01-0.1 M (e.g., 0.01 M, 0.02 M, 0.04 M, 0.06 M, 0.08 M, 0.1 M) NaOAc, at pH 5.5-7.5 (e.g., 5.5, 6.0, 6.5, 7.0, or 7.5) and 25-40 C (e.g., 25 C, 30 C, 35 C, or 40 C) for 1-24 hours (e.g., 1 h, 2 h, 4 h, 6 h, 8 h, 12 h, 18 h, 24 h). In some embodiments, the heparin and/or heparan sulfate is diluted (e.g., to reduce the ionic strength). In certain embodiments, the heparin and/or heparan sulfate is then loaded onto an ion exchange column (e.g., in 5-100 mM NaOAc (e.g., 5 mM, 10 mM, 20 mM, 30 mM, 40 mM, 50 mM, 60 mM, 70 mM, 75 mM, 80 mM, 90 mM, 95 mM, 100 mM) pH 5-7 (e.g., 5.5, 6.0, 6.5, 7.0) with 0-300 mM NaCl (e.g., 5 mM, 10 mM, 20 mM, 30 mM, 40 mM, 50 mM, 60 mM, 70 mM, 75 mM, 80 mM, 90 mM, 95 mM, 100 mM, 150 mM, 200 mM, 250 mM, 300 mM)). In some embodiments, after washing, the bound heparin and/or heparan sulfate is eluted with a suitable solvent or solvent system (e.g., with 5-100 mM (e.g., 5 mM, 10 mM, 20 mM, 30 mM, 40 mM, 50 mM, 60 mM, 70 mM, 75 mM, 80 mM, 90 mM, 95 mM, 100 mM) NaOAc pH 5-7 (e.g., 5.5, 6.0, 6.5, 7.0) with 0.8-3 M NaCl (e.g., 0.8 M, 1 M, 1.2 M, 1.4 M, 1.6 M, 1.8 M, 2 M, 2.5 M, or 3 M)). In certain embodiments, the eluted heparin and/or heparan sulfate is then concentrated and/or desalted (e.g., by ethanol precipitation, size exclusion, or other methods). In some embodiments, the eluted heparin and/or heparan sulfate is concentrated and/or desalted by cetylpyridinium chloride/ethanol precipitation. The purified heparin and/or heparan sulfate is optionally dried or lyophilized.

In another non-limiting example, the cells or conditioned media comprising the heparin and/or heparan sulfate compositions are extracted using chilled guanidine HCl/Zwittergent extraction buffer with 10 mM EDTA, protease inhibitors (10 mM NEM, 1 mM PMSF, 1 μg/ml pepstatin A, and 0.5 μg/ml leupeptin). Extracted samples are centrifuged to remove insoluble residue. The pellet is optionally re-extracted and centrifuged. Heparin and/or heparan sulfate is purified from the extract by anion-exchange chromatography on a DEAE-Sephacel™ column in a bind and elute procedure. Eluted heparin and/or heparan sulfate compositions are desalted using a Sephadex® G-25 gel filtration and subsequently lyophilized and rehydrated in a physiologically acceptable buffer. Additional details and alternative purification procedures are found in Esko, J. Special Considerations for Proteoglycans and Glycosaminoglycans and Their Purification. 2000. Curr. Protoc. Mol. Biol. 22:17.2.1-17.2.9, which is hereby incorporated by reference in its entirety.

In some embodiments, heparin and/or heparan sulfate compositions, are naturally found attached to a core protein (together forming a proteoglycan). In certain embodiments, a purification process used herein is a process that includes a protocol that cleaves a core protein from a heparin and/or heparan sulfate (e.g., treatment with a protease, such as a non-specific protease (e.g., Pronase) to cleave the proteins; or by chemical means (beta-elimination chemistry)). In other embodiments, a purification process described herein does not include a protocol that cleaves a heparin and/or heparan sulfate from a core protein. In some embodiments, heparin and/or heparan sulfate compositions are further purified using enzymes including but not limited to DNase, RNase, chondroitinase ABC, hyaluronidase, and combinations thereof.

Pharmaceutical Compositions

Disclosed herein are pharmaceutical compositions comprising one or more heparin, and/or heparan sulfate compositions with a defined pattern of modification derived from genetically modified cell lines as described herein and one or more pharmaceutically acceptable carriers or excipients. In certain embodiments, pharmaceutical compositions are formulated in a conventional manner using one or more physiologically acceptable carriers including, e.g., excipients and auxiliaries which facilitate processing of the active compounds into preparations which are suitable for pharmaceutical use. In certain embodiments, proper formulation is dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., Pharmaceutical Dosage Forms, *Marcel Decker*, New York, N.Y., 1980; and Pharmaceutical Dosage Forms and Drug Delivery Systems, Seventh Ed. (Lippincott Williams & Wilkins1999).

A pharmaceutical composition, as used herein, refers to a mixture of one or more heparin, and/or heparan sulfate compositions with defined patterns of modification described herein, with other chemical components, such as carriers, stabilizers, diluents, dispersing agents, suspending agents, thickening agents, and/or excipients. In certain instances, the pharmaceutical composition facilitates administration of the heparin, and/or heparan sulfate compositions with a defined pattern of modification to an individual or cell. In certain embodiments of practicing the methods of treatment or use provided herein, therapeutically effective amounts of heparin, and/or heparan sulfate compositions with a defined pattern of modification described herein are administered in a pharmaceutical composition to an individual having a disease, disorder, or condition to be treated. In specific embodiments, the individual is a human. As discussed herein, the heparin, and/or heparan sulfate compositions with a defined pattern of modification described herein are either utilized singly or in combination with one or more additional therapeutic agents.

In certain embodiments, one or more heparin, and/or heparan sulfate compositions with defined patterns of modification described herein are combined with one or more other active pharmaceutical ingredients. In some cases, one or more heparin, and/or heparan sulfate compositions with defined patterns of modification described herein act as an excipient in the pharmaceutical composition with the other active pharmaceutical ingredients. In some cases, one or more heparin, and/or heparan sulfate compositions with defined patterns of modification described herein act as an adjuvant in the pharmaceutical composition. In some cases, one or more heparin, and/or heparan sulfate compositions with defined patterns of modification described herein enhance the activity of the other components of the pharmaceutical composition. In some embodiments, the other component is a protein, a nucleic acid, a lipid, or a small molecule.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein are optionally manufactured in a conventional manner, such as, by way of example only, by means of conventional mixing, dissolving, granulating, dragee-making, levigating, emulsifying, encapsulating, entrapping or compression processes.

In certain embodiments, a pharmaceutical compositions described herein includes one or more heparin, and/or heparan sulfate compositions with a defined pattern of modification described herein, as an active ingredient in free-acid or free-base form, or in a pharmaceutically acceptable salt form. In some embodiments, the compounds described herein are utilized in a crystalline or lyophilized form. In certain embodiments, an active metabolite or prodrug of a compound described herein is utilized. In some situations, a compound described herein exists as different stereoisomers. All stereoisomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the heparin, and/or heparan sulfate compositions with a defined pattern of modification presented herein are also considered to be disclosed herein.

A "carrier" includes, in some embodiments, a pharmaceutically acceptable excipient and is selected on the basis of compatibility with heparin, and/or heparan sulfate compositions with a defined pattern of modification disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., Pharmaceutical Dosage Forms, *Marcel Decker*, New York, N.Y., 1980; and Pharmaceutical Dosage Forms and Drug Delivery Systems, Seventh Ed. (Lippincott Williams & Wilkins1999).

Moreover, in certain embodiments, the pharmaceutical compositions described herein are formulated as a dosage form. As such, in some embodiments, provided herein is a dosage form comprising heparin, and/or heparan sulfate compositions with a defined pattern of modification described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using coating procedures, such as those described in Remington's Pharmaceutical Sciences, 20th Edition (2000), a film coating is provided around the formulation of the heparin, and/or heparan sulfate compositions with a defined pattern of modification. In one embodiment, a heparin, and/or heparan sulfate compositions with a defined pattern of modification described herein is in the form of a particle and some or all of the particles of the compound are coated. In certain embodiments, some or all of the particles of a glycosaminoglycan and/or heparan sulfate compositions with a defined pattern of modification described herein are microencapsulated. In some embodiment, the particles of the heparin, and/or heparan sulfate compositions with a defined pattern of modification described herein are not microencapsulated and are uncoated.

In certain embodiments, the pharmaceutical composition described herein is in unit dosage forms suitable for single administration of precise dosages. In unit dosage form, the formulation is divided into unit doses containing appropriate quantities of one or more therapeutic compound. In some embodiments, the unit dosage is in the form of a package containing discrete quantities of the formulation. Non-limiting examples are packaged tablets or capsules, and powders in vials or ampoules. Aqueous suspension compositions are optionally packaged in single-dose non-reclosable containers. In some embodiments, multiple-dose re-closeable containers are used. In certain instances, multiple dose containers comprise a preservative in the composition. By way of example only, formulations for parenteral injection are presented in unit dosage form, which include, but are not limited to ampoules, or in multi dose containers, with an added preservative.

Methods of Treatment

In addition to applications in research, heparin, heparan sulfate, and other glycosaminoglycans and proteoglycans have potential applications as functional ingredients in pharmaceutical or nutraceutical preparations across a range of medical treatments including thrombosis, inflammation, cancer, microbial infections, neurodegenerative disorders and wound healing among others. Pharmaceutical heparin is a widely used, commercially prepared fraction therapeutically used for its anticoagulant properties in treatments and for prevention of thrombotic disorders. Heparin has a number of negative attributes however, including a propensity to cause thrombocytopenia and hemorrhagic bleeding. This may be reduced by engineering cells to produce a heparan sulfate/heparin composition that retains significant antithrombin binding but with reduced platelet factor 4 (PF4) binding. Heparin also has a natural high structural diversity, which can result in significant oscillations in the therapeutic dosage window. A defined heparin or heparan sulfate composition produced by genetically modified cell lines would provide a clear advantage and improvement over the currently available treatments.

A number of novel heparan sulfate/heparin structures have been prepared from marine invertebrate organisms. Initial characterizations have identified unique anticoagulant properties that appear to be associated with significantly reduced bleeding effects and other advantages compared to heparin. One unique invertebrate structure that resembles heparan sulfate and heparin termed acharan sulfate (AS) has been isolated from the pulmonate gastropod (snail) *A. fulica*, (see for example, Wieira T C et al., Eur J Biochem. 2004. 271(4): 845-54, which is hereby incorporated by reference in its entirety). Despite a lower sulfation content and simple structure, AS presents a multitude of medicinal properties including bFGF mitogenicity, anticoagulation, anti-angiogenesis in models of inflammation, immunostimulant, hypoglycemic, hypolipidemic, tumor suppression, antibacterial, and an aid to wound healing, among others. Some of these novel compositions may entail new enzymes and other factors, however, once understood, cells may be engineered to produce adequate quantities of either these or similar structures to take advantage of the medical applications on a commercial basis.

Therefore, disclosed herein are methods of treating disease in subjects in need thereof by administering an effective amount of one or more heparin, and/or heparan sulfate compositions with defined modification patterns described herein. In some embodiments, the disease comprises one or more of thrombosis, inflammation, cancer, microbial infections, neurodegenerative disorders, wound healing, and other diseases with known association with heparin, and/or heparan sulfate that would be known by one of skill in the art.

In some embodiments, the compositions or pharmaceutical compositions disclosed herein are administered to the subject by any route known in the art, found to be effective in treating thrombosis, inflammation, cancer, microbial infections, neurodegenerative disorders and wound healing among others. In some embodiments, the compositions or pharmaceutical compositions disclosed herein are administered orally, rectally, sublingually, sublabially, buccally, epidurally, entracerebrally, intracerebroventricalarly, topically, transdermally, nasally, intraarterially, intraarticularly, intracardiacally, intradermally, subcutaneously, intralesionally, intramuscular, intraocularly, intraosseously, intraperitoneally, intrathecally, intravenously, transmucosally, or any other route of administration known by one of skill in the art.

Treatment of Thrombosis

In some embodiments, there is provided a method of treating thrombosis in a subject in need thereof comprising administering to the subject an effective amount of one or more heparin, and/or heparan sulfate compositions with defined modification patterns described herein. In some embodiments, the thrombosis comprises, venous thrombosis, deep vein thrombosis, portal vein thrombosis, renal vein thrombosis, jugular vein thrombosis, Budd-Chiari syndrome, Paget-Schroetter disease, Cerebral venous sinus thrombosis, Cavernous sinus thrombosis, arterial thrombosis, stroke, myocardial infarction, Hepatic artery thrombosis, acute coronary syndrome atrial fibrillation, or pulmonary embolism. In some embodiments, treatment of the thrombosis reduces swelling, pain, tenderness, skin discoloration, shortness of breath, chest pain, rapid heart rate, cough, or other symptom of thrombosis. In some embodiments, the method prevents or eliminates a blood clot. In some embodiments, the method prevents or eliminates a blood clot without causing heparin-induced thrombocytopenia.

Treatment of Inflammation

In some embodiments, there is provided a method of treating inflammation in a subject in need thereof comprising administering to the subject an effective amount of one or more heparan sulfate compositions with defined modification patterns described herein. In some embodiments, the inflammation comprises rheumatoid arthritis, juvenile rheumatoid arthritis, osteoarthritis, psoriatic arthritis, multiple sclerosis (MS), encephalomyelitis, myasthenia gravis, systemic lupus erythematosus (SLE), asthma, allergic asthma, autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis (UC), inflammatory bowel disease (IBD), cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type 2 diabetes), immune-mediated infertility, autoimmune Addison's disease, pemphigus vulgaris, pemphigus *foliaceus*, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome or an allergy, Behcet's disease, X-linked lymphoproliferative syndrome (SH2D1A/SAP deficiency), hyper IgE syndrome or Graft vs. Host Disease (GVHD). In some embodiments, treatment of the inflammation reduces pain, redness, swelling, loss of joint function, fever, chills, fatigue, headache, loss of appetite, muscle stiffness, or other symptom associated with inflammation or inflammatory disease.

Treatment of Cancer

In some embodiments, there is provided a method of treating cancer in a subject in need thereof comprising administering to the subject an effective amount of one or more heparan sulfate compositions with defined modification patterns described herein. In some embodiments, the cancer comprises Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or other type of cancer. In some embodiments, the cancer comprises a metastasis of one or more of the above cancers.

Efficacy in treating cancer in particular may be measured by any suitable metric. In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, and/or a reduction in the size of at least one tumor such that a human is treated for the proliferative disorder. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. In some embodiments, the primary efficacy parameter used to evaluate the treatment of cancer preferably is a reduction in the size of a tumor. Tumor size can be determined using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

Desirably, the growth of a tumor is stabilized (i.e., one or more tumors do not increase more than 1%, 5%, 10%, 15%, or 20% in size, and/or do not metastasize) as a result of treatment. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. In some embodiments, the size of a tumor is reduced at least about 5% (e.g., at least about 10%, 15%, 20%, or 25%). In some embodiments, tumor size is reduced at least about 30% (e.g., at least about 35%, 40%, 45%, 50%, 55%, 60%, or 65%). In some embodiments, tumor size is reduced at least about 70% (e.g., at least about 75%, 80%, 85%, 90%, or 95%). In some embodiments, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

When a tumor is subject to surgical resection following completion of the therapeutic period, the efficacy of the inventive method in reducing tumor size can be determined by measuring the percentage of resected tissue that is necrotic (i.e., dead). In some embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is about 100%, that is, no tumor tissue is present or detectable.

A number of secondary parameters can be employed to determine the efficacy of the inventive method. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA) prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also efficiently distinguishes small tumors from surrounding tissue.

In some embodiments, the treatment of cancer in a human patient is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 μlevel before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The Karnofsky Performance Scale allows patients to be classified according to their functional impairment. The Karnofsky Performance Scale is scored from 0-100. In general, a lower Karnofsky score is predictive of a poor prognosis for survival. Thus, the treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. The NCI toxicity scale (published April 1999) and Common Toxicity Criteria Manual (updated August 1999) is available through the NCI, e.g., or in the Investigator's Handbook for participants in clinical trials of investigational agents sponsored by the Division of Cancer Treatment and Diagnosis, NCI (updated March 1998). Desirably, methods described herein are associated with minimal adverse events, e.g. Grade 0, Grade 1, or Grade 2 adverse events, as graded by the CTEP/NCI. However, reduction of tumor size, although preferred, is not required in that the actual size of tumor may not shrink despite the eradication (such as in necrosis) of tumor cells. Eradication of cancerous cells is sufficient to realize a therapeutic effect. Likewise, any reduction in tumor size is sufficient to realize a therapeutic effect.

Detection, monitoring, and rating of various cancers in a human are further described in Cancer Facts and FIGS. 2001, *American Cancer Society*, New York, N.Y. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

Treatment of Microbial Infection

In some embodiments, there is provided a method of treating a microbial infection in a subject in need thereof comprising administering to the subject an effective amount of one or more heparin, and/or heparan sulfate compositions with defined modification patterns described herein. In some embodiments the microbial infection comprises a bacterial infection. In some embodiments, the bacterial infection is a *Bacillus* such as a *Bacillus anthracis* or a *Bacillus cereus*; a *Bartonella* such as a *Bartonella henselae* or a *Bartonella quintana*; a *Bordetella* such as a *Bordetella pertussis*; a *Borrelia* such as a *Borrelia burgdorferi*, a *Borrelia garinii*, a *Borrelia afzelii*, a *Borrelia recurrentis*; a *Brucella* such as a *Brucella abortus*, a *Brucella canis*, a *Brucella melitensis* or a *Brucella suis*; a *Campylobacter* such as a *Campylobacter jejuni*; a *Chlamydia* or *Chlamydophila* such as *Chlamydia pneumoniae, Chlamydia trachomatis, Chlamydophila psittaci*; a *Clostridium* such as a *Clostridium botulinum*, a *Clostridium difficile*, a *Clostridium perfringens*, a *Clostridium tetani*; a *Corynebacterium* such as a *Corynebacterium diphtheriae*; an *Enterococcus* such as a *Enterococcus faecalis* or a *Enterococcus faecium*; a *Escherichia* such as a *Escherichia coli*; a *Francisella* such as a *Francisella tularensis*; a *Haemophilus* such as a *Haemophilus influenzae*; a *Helicobacter* such as a *Helicobacter pylori*; a *Legionella* such as a *Legionella pneumophila*; a Leptospira such as a Leptospira interrogans, a Leptospira santarosai, a Leptospira weilii or a Leptospira noguchii; a *Listeria* such as a *Listeria monocytogenes*; a *Mycobacterium* such as a *Mycobacterium leprae*, a *Mycobacterium tuberculosis* or a *Mycobacterium ulcerans*; a *Mycoplasma* such as a *Mycoplasma pneumoniae*; a *Neisseria* such as a *Neisseria gonorrhoeae* or a *Neisseria meningitidis*; a *Pseudomonas* such as a *Pseudomonas aeruginosa*; a *Rickettsia* such as a *Rickettsia rickettsii*; a *Salmonella* such as a *Salmonella typhi* or a *Salmonella typhimurium*; a *Shigella* such as a *Shigella sonnei*; a *Staphylococcus* such as a *Staphylococcus aureus*, a *Staphylococcus epidermidis*, a *Staphylococcus saprophyticus*; a *Streptococcus* such as a *Streptococcus agalactiae*, a *Streptococcus pneumoniae*, a *Streptococcus pyogenes*; a *Treponema* such as a *Treponema pallidum*; a *Vibrio* such as a *Vibrio cholerae*; a *Yersinia* such as a *Yersinia pestis*, a *Yersinia enterocolitica* or a *Yersinia pseudotuberculosis*. In some embodiments, the microbial infection comprises a viral infection. In some embodiments, the viral infection comprises a Adenoviridae such as, an Adenovirus; a Herpesviridae such as a Herpes simplex, type 1, a Herpes simplex, type 2, a Varicella-zoster virus, an Epstein-barr virus, a Human cytomegalovirus, a Human herpesvirus, type 8; a Papillomaviridae such as a Human papillomavirus; a Polyomaviridae such as a BK virus or a JC virus; a Poxviridae such as a Smallpox; a Hepadnaviridae such as a Hepatitis B virus; a Parvoviridae such as a Human bocavirus or a Parvovirus; a Astroviridae such as a Human astrovirus; a Caliciviridae such as a Norwalk virus; a Picornaviridae such as a coxsackievirus, a hepatitis A virus, a poliovirus, a rhinovirus; a Coronaviridae such as a Severe acute respiratory syndrome virus; a Flaviviridae such as a Hepatitis C virus, a yellow fever virus, a dengue virus, a West Nile virus; a Togaviridae such as a Rubella virus; a Hepeviridae such as a Hepatitis E virus; a Retroviridae such as a Human immunodeficiency virus (HIV); a Orthomyxoviridae such as an Influenza virus; a Arenaviridae such as a Guanarito virus, a Junin virus, a Lassa virus, a Machupo virus, a Sabiá virus; a Bunyaviridae such as a Crimean-Congo hemorrhagic fever virus; a Filoviridae such as a Ebola virus, a Marburg virus; a Paramyxoviridae such as a Measles virus, a Mumps virus, a Parainfluenza virus, a Respiratory syncytial virus, a Human metapneumovirus, a Hendra virus, a Nipah virus; a Rhabdoviridae such as a Rabies virus; a Hepatitis D virus; or a Reoviridae such as a Rotavirus, a Orbivirus, a Coltivirus, a Banna virus infection. In some embodiments, the microbial infection comprises a fungal infection. In some embodiments, the microbial infection comprises a fungal infection. In some embodiments, the fungal infection comprises actinomycosis, allergic bronchopulmonary aspergillosis, aspergilloma, aspergillosis, athlete's foot, basidiobolomycosis, basidiobolus ranarum, black *piedra*, blastomycosis, *candida krusei*, candidiasis, chronic pulmonary aspergillosis, *chrysosporium*, chytridiomycosis, coccidioidomycosis, conidiobolomycosis, cryptococcosis, *cryptococcus gattii*, deep dermatophytosis, dermatophyte, dermatophytid, dermatophytosis, endothrix, entomopathogenic fungus, epizootic lymphangitis, esophageal candidiasis, exothrix, fungal meningitis, fungemia, *geotrichum, geotrichum candidum*, histoplasmosis, lobomycosis, massospora cicadina, *microsporum gypseum*, muscardine, mycosis, myringomycosis, neozygites remaudierei, neozygites slavi, ochroconis gallopava, ophiocordyceps *arborescens*, ophiocordyceps coenomyia, ophiocordyceps macroacicularis, ophiocordyceps *nutans*, oral candidiasis, paracoccidioidomycosis, pathogenic dimorphic fungi, penicilliosis, *piedra*, piedraia, *pneumocystis* pneumonia, pseudallescheriasis, scedosporiosis, sporotrichosis, tinea, tinea barbae, tinea capitis, tinea corporis, tinea cruris, tinea faciei, tinea incognito, tinea nigra, tinea pedis, tinea *versicolor*, vomocytosis, white nose syndrome, zeaspora, or zygomycosis. In some embodiments, treatment of the microbial infection reduces one or more symptoms such as fever, diarrhea, fatigue, or pain.

Treatment of Genetic Disorders

In some embodiments, there is provided a method of treating a genetic disorder in a subject in need thereof comprising administering to the subject an effective amount of one or more heparan sulfate compositions with defined modification patterns described herein. In some embodiments, the genetic disorder comprises Achondrogenesis type IB; Atelosteogenesis type II; Diastrophic dysplasia; Multiple epiphyseal dysplasia, AR type; Spondyloepimetaphyseal dysplasia, Pakistani type (PAPSS2 type); Hyperandrogenism; Brachyolmia, AR type; Schneckenbecken dysplasia; EDS, progeroid form; Larsen-like syndrome, B3GAT3 type; Hereditary motor and sensory neuropathy, unknown type; Bell palsy; Temtamy pre-axial brachydactyly syndrome; Syndromic recessive pre-axial brachydactyly; Spondyloepiphyseal dysplasia, Omani type; Chondrodysplasia with multiple dislocations; Humerospinal dysostosis; Larsen syndrome, AR type; Desbuquois syndrome; Bipolar disorder; Depressive disorder; Diaphragmatic hernia; Microphthalmia; EDS, Kosho type; EDS, musculocontractural type; EDS, type VIB; ATCS; or other genetic disorder. In some embodiments, the method reduces symptoms of the disorder. In some embodiments, the method completely eliminates symptoms of the disorder. In some embodiments, the method cures the disorder. In some embodiments, the method eliminates the need for alternative therapies for the disorder. In some embodiments, the method delays onset of more severe symptoms of the disorder.

Treatment of Neurodegenerative Disorders

In some embodiments, there is provided a method of treating a neurodegenerative disorder in a subject in need thereof comprising administering to the subject an effective amount of one or more heparan sulfate compositions with defined modification patterns described herein. In some embodiments, the neurodegenerative disorder comprises Alzheimer's disease, Parkinson's disease, Huntington's disease, Amyotrophic lateral sclerosis, Dementia, Transmissible spongiform encephalopathy, Dentatorubropallidoluysian atrophy, Spinal and bulbar muscular atrophy, Spinocerebellar ataxia Type 1, Spinocerebellar ataxia Type 2, Spinocerebellar ataxia Type 3, Spinocerebellar ataxia Type 6, Spinocerebellar ataxia Type 7, or Spinocerebellar ataxia Type 17. In some embodiments, the method reduces symptoms of a neurodegenerative disorder such as memory loss, disorientation, confusion, mood and/or personality disorder, tremor, bradykinesia, muscle rigidity, balance impairment, speech disorder, choria, dystonia, ataxia, swallowing disorder, irritability, sadness, apathy, social withdrawal, insomnia, fatigue, suicidal thoughts, weakness, speech disorder, muscle cramping, impaired coordination, stumbling, unsteady gait, uncontrolled movements, slurred speech, vocal changes, or headache. In some embodiments, the method delays onset of more severe symptoms. In some embodiments, the delay is 1, 2, 3, 4, 5, 6 or more weeks, 1, 2, 3, 4, 5, 6, 7, 8, 9, 10, 11, 12, or more months, 1, 2, 3, 4, 5, 6, 7, 8, 9, 10, 11, 12, 13, 14, 15, 20, 25, 30, or more years.

Treatment of Wounds

In some embodiments, there is provided a method of treating a wound in a subject in need thereof comprising administering to the subject an effective amount of one or more heparan sulfate compositions with defined modification patterns described herein. In some embodiments, the wound comprises an incision, a laceration, an abrasion, an avulsion, a puncture wound, a penetration wound, a gunshot wound, a hematoma, or a crush injury. In some embodiments, the method reduces symptoms or complications related to a wound, such as drainage, pus, fever, or lymph node swelling. In some embodiments, the method speeds the healing time of a wound. In some embodiments, the method treats diabetic wounds. In some embodiments, the method treats a nerve injury. In some embodiments, the method treats a spinal cord injury.

Definitions

The term "glycosaminoglycan" or "GAG" as used herein refers to long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) or galactose.

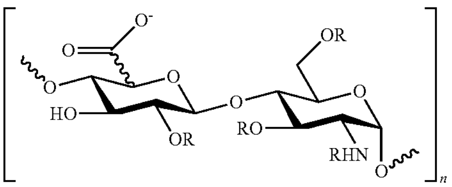

Heparin/Heparan Sulfate

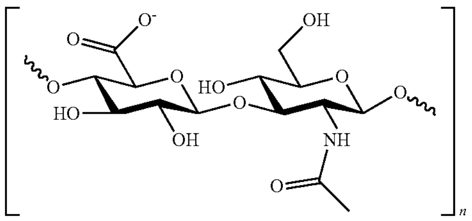

Hyaluronic Acid

-continued

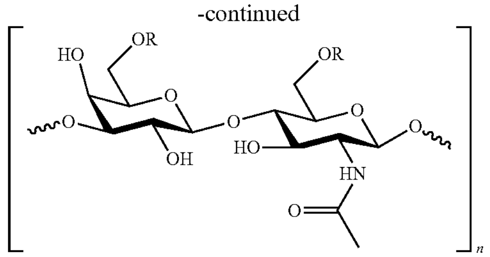

Keratan Sulfate

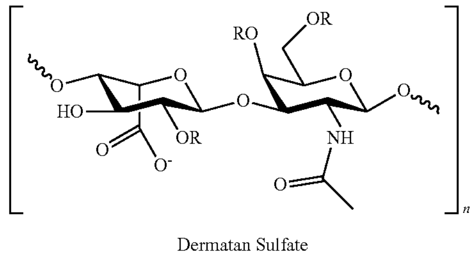

Dermatan Sulfate

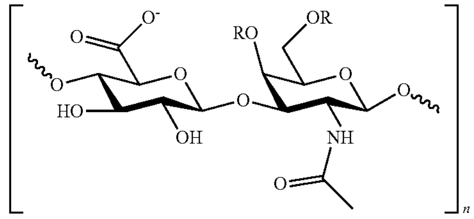

Chondroitin Sulfate

The term "proteoglycan" as used herein refers to proteins that are heavily glycosylated. The basic proteoglycan unit comprises a core protein with one or more covalently attached glycosaminoglycan or GAG chains.

The term "core protein" as used herein refers to a protein component of a proteoglycan.

The term "heparin" as used herein refers to a glycosaminoglycan made of repeating disaccharide units comprising one or more of β-D-glucuronic acid (GlcA), 2-deoxy-2-acetamido-α-D-glucopyranosyl (GlcNAc), α-L-iduronic acid (IdoA), 2-O-sulfo-α-L-iduronic acid (IdoA2S), 2-deoxy-2-sulfamido-α-D-glucopyranosyl (GlcNS), 2-deoxy-2-sulfamido-α-D-glucopyranosyl-6-O-sulfate (GlcNS6S) or 2-deoxy-2-sulfamido-α-D-glucopyranosyl-3,6-O-disulfate (GlcNS3S6S) or 2-deoxy-2-sulfamido-α-D-glucopyranosyl-3-O-sulfate (GlcNS3S).

The term "heparan sulfate" as used herein refers to a linear polysaccharide with the structure. Heparan sulfate is made of repeating disaccharide units. The repeating disaccharide units can comprise one or more of β-D-glucuronic acid (GlcA), 2-deoxy-2-acetamido-α-D-glucopyranosyl (GlcNAc), α-L-iduronic acid (IdoA), 2-O-sulfo-α-L-iduronic acid (IdoA2S), 2-deoxy-2-sulfamido-α-D-glucopyranosyl (GlcNS), 2-deoxy-2-sulfamido-α-D-glucopyranosyl-6-O-sulfate (GlcNS6S) or 2-deoxy-2-sulfamido-α-D-glucopyranosyl-3,6-O-disulfate (GlcNS3S6S) or 2-deoxy-2-sulfamido-α-D-glucopyranosyl-3-O-sulfate (GlcNS3S).

The term "chondroitin sulfate" as used herein refers to a linear polysaccharide with the structure. Chondroitin sulfate is made of repeating dissacharide units. The repeating disaccharide units can comprise one or more of N-acetylgalactosamine (GalNAc), N-acetylgalactosamine-4-sulfate (GalNAc4S), N-acetylgalactosamine-6-sulfate (GalNAc6S), N-acetylgalactosamine-4,6-disulfate (GalNAc4S6S) and β-D-glucuronic acid (GlcA), D-glucuronic acid-2-sulfate (GlcA2S), D-glucuronic acid-3-sulfate (GlcA3S), L-iduronic acid (IdoA), L-iduronic acid-2-sulfate (IdoA2S).

The terms "sulfation pattern", "defined pattern of sulfation", and "defined modification pattern" as used herein refer to enzymatic modifications made to the glycosaminoglycan including but not limited to include sulfation, deacetylation, and epimerization. This also includes heparin and heparan sulfate compositions having a defined disaccharide composition.

The term "genetically modified cell line" as used herein refers to a cell line with specific modifications made to the genome of the cell line. In some embodiments, the cell line is mammalian. In some embodiments, the cell line is human or murine. In some embodiments, the modifications comprise genetic knockouts, whereby the cell line becomes genetically deficient for one or more genes. In some embodiments, the modifications comprise making transgenic cell lines, whereby the cell line obtains genetic material not present in the wildtype cell line or genetic material under the control of active promoter.

The term "genetically deficient" as used herein refers to a genome that is modified to be missing one or more genes of interest. In some embodiments, the modification is made using a cre/lox system, CRISPR, siRNA, shRNA, antisense oligonucleotide, miRNA, or other genetic modification or mutagenesis method known in the art.

The term "transgenic" as used herein refers to a genome that is modified to include additional genetic material encoding one or more genes of interest. In some embodiments, the modification is made using transfection, infection with a virus, cre/lox knock-in, CRISPR/cas mediated knock-in, or other method of introducing genetic material to a cell that is known in the art.

The terms "subject", "individual", "recipient", "host", and "patient", are used interchangeably herein and refer to any mammalian subject for whom diagnosis, treatment or therapy is desired, particularly humans. "Mammal" for purposes of treatment refers to any animal classified as a mammal, including humans, domestic and farm animals, and laboratory, zoo, spots, or pet animals, such as dogs, horses, cats, cows, sheep, goats, pigs, mice rats, rabbits, guinea pigs, monkeys, etc. In some embodiments, the mammal is human.

As used herein, the terms "treatment", "treating" and the like, refer to administering an agent or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment", as used herein, may include treatment of a disease in a mammal, particularly in a human and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a disease, including any objective or subjective parameter such as abatement; remission; diminishing of symptoms or making the disease more tolerable to the patient; slowing in the rate of degeneration or decline; or making the final point of degeneration with less debilitation. The treatment or amelioration of symptoms can be based on objective or subjective parameters; including the results of an examination by a physician. Accordingly, the term "treating" includes the administration of the compounds or agents disclosed hereinto prevent or delay, to alleviate, or to arrest or inhibit development of the symptoms of conditions associated with the disease. The term "therapeutic effect refers to the reduction, elimination, or prevention of the disease, symptoms of the disease, or side effects of the disease in the subject.

"In combination with", "combination therapy" and "combination products" refer, in certain embodiments, to concurrent administration to a patient of a first therapeutic and the compounds used herein. When administered in combination, each component can be administered at the same time or sequentially in any order at different points in time. Thus, each component can be administered separately but sufficiently closely in time as to provide the desired therapeutic effect.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means that the amount that, when administered to a subject for treating a disease, is sufficient to effect treatment for that disease.

The term "substantially free" as used herein means most or all of one or more of a contaminant, such as the materials with which it typically associates with in nature, is absent from the composition. Thus a heparin or heparan sulfate composition with defined modification patterns described herein that is "substantially free" from one or more contaminating glycosaminoglycans that do not have the desired defined modification pattern and/or biological and/or therapeutic effect has no or little of the contaminant. For example, a heparan sulfate composition is "substantially free" from a contaminant such as other glycosaminoglycans such as: chondroitin sulfate, keratan sulfate and/or hyaluronic acid; nucleic acids; and/or proteins, found with the heparan sulfate composition in nature, has very little or none of the contaminant, for example less than 5%, less than 4%, less than 3%, less than 2%, less than 1%, or less than 0.5% of the composition is made up by the contaminant. In some embodiments, the composition is 60%, 70%, 80%, 85%, 90%, 95%, 96%, 97%, 98%, 99%, or 100% free from one or more of a contaminating glycosaminoglycan, nucleic acids, and or proteins. In some embodiments, the composition is at least 95% free from contaminating glycosaminoglycans, nucleic acids, and or proteins. In some embodiments, the composition is at least 99% free from contaminating glycosaminoglycans, nucleic acids, and or proteins.

The term "substantially pure" as used herein means that the composition is free of most or all of the materials with which it typically associates with in nature. Thus a "substantially pure" glycosaminoglycan and/or heparan sulfate composition with defined modification patterns described herein does not include other contaminating glycosaminoglycan and/or heparan sulfate compositions that do not have the desired defined modification pattern and/or biological and/or therapeutic effect. For example, a "substantially pure" heparan sulfate composition is free from most other glycosaminoglycans such as: chondroitin sulfate, keratan sulfate and/or hyaluronic acid; nucleic acids; and/or proteins, found with the heparan sulfate composition in nature. In some embodiments, the composition is 60%, 70%, 80%, 85%, 90%, 95%, 96%, 97%, 98%, 99%, or 100% free from contaminating glycosaminoglycans, chondroitin sulfate, dermatan sulfate, keratan sulfate, nucleic acids, and or proteins. In some embodiments, the composition is 95% free from contaminating glycosaminoglycans, chondroitin sulfate, dermatan sulfate, keratan sulfate, nucleic acids, and or proteins. In some embodiments, the composition is 99% free from contaminating glycosaminoglycans, chondroitin sulfate, dermatan sulfate, keratan sulfate, nucleic acids, and or proteins. In some embodiments, the composition is greater than 99% free from contaminating glycosaminoglycans, chondroitin sulfate, dermatan sulfate, keratan sulfate, nucleic acids, and or proteins.

The disclosure herein is further clarified in reference to a partial list of numbered embodiments as follows. 1. A composition comprising a heparin derived from a genetically modified cell line. 2. The composition of embodiment 1, wherein the composition is derived from a cell line genetically modified to be deficient for one or more genes recited in Table 6. 3. The composition of any one of embodiment 1 or embodiment 2, wherein the composition is derived from a cell line genetically modified to be deficient for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 glucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2

(NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). 4. The composition of any one of embodiments 1 to 3, wherein the composition is derived from a cell line genetically modified to be deficient for chondroitin sulfate synthase 1 (ChSy). 5. The composition of any one of embodiments 1 to 4, wherein the composition is derived from cells that do not produce chondroitin sulfate. 6. The composition of any one of embodiments 1 to 5, wherein the composition is derived from a cell line genetically modified to be transgenic for one or more genes recited in Table 6. 7. The composition of any one of embodiments 1 to 6, wherein the composition is derived from a cell line genetically modified to be transgenic for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 glucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). 8. The composition of any one of embodiments 1 to 7, wherein the composition is derived from a cell line genetically modified to be deficient for chondroitin sulfate synthesis (ChA27) and transgenic for Hs3st1. 9. The composition of any one of embodiments 1 to 8, wherein the composition comprises a heparin with a defined pattern of sulfation. 10. The composition of any one of embodiments 1 to 9, wherein the heparin is at least 95% free of protein and nucleic acid contamination. 11. The composition of any one of embodiments 1 to 10, wherein the heparin is at least 95% free of chondroitin sulfate. 12. The composition of any one of embodiments 1 to 11, wherein the cell line comprises a cell line in Table 4. 13. A pharmaceutical composition comprising the composition of any one of embodiments 1 to 12 and a pharmaceutically acceptable carrier or excipient. 14. A composition comprising a hyper-sulfated heparan sulfate derived from a genetically modified cell line. 15. The composition of embodiment 14, wherein the composition is derived from a cell line genetically modified to be deficient for one or more genes recited in Table 6. 16. The composition of any one of embodiment 14 or embodiment 15, wherein the composition is derived from a cell line genetically modified to be deficient for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 glucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). 17. The composition of any one of embodiments 14 to 16, wherein the composition is derived from a cell line genetically modified to be deficient for chondroitin sulfate synthase 1 (ChSy). 18. The composition of any one of embodiments 14 to 17, wherein the composition is derived from cells that do not produce chondroitin sulfate. 19. The composition of any one of embodiments 14 to 18, wherein the composition is derived from a cell line genetically modified to be transgenic for one or more genes recited in Table 6. 20. The composition of any one of embodiments 14 to 19, wherein the composition is derived from a cell line genetically modified to be transgenic for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 glucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). 21. The composition of any one of embodiments 14 to 20, wherein the composition is derived from a cell line genetically modified to be deficient for chondroitin sulfate synthesis (ChA27) and transgenic for Hs3st1. 22. The composition of any one of embodiments 14 to 21, wherein the composition comprises a hyper-sulfated heparan sulfate with a defined pattern of sulfation. 23. The composition of any one of embodiments 14 to 22, wherein the hyper-sulfated heparan sulfate is at least 95% free of protein and nucleic acid contamination. 24. The composition of any one of embodiments 14 to 23, wherein the hyper-sulfated heparan sulfate is at least 95% free of chondroitin sulfate. 25. The composition of any one of embodiments 14 to 24, wherein the cell line comprises a cell line in Table 3. 26. A pharmaceutical composition comprising the composition of any one of embodiments 14 to 25 and a pharmaceutically acceptable carrier or excipient. 27. A composition comprising a cell deficient in one or more genes recited in Table 6. 28. The composition of embodiment 27, wherein the cell is deficient in one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (S79639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 μlucuronyl epimerase (CSEPI (XM_035390)), Heparan sulfate 2-O-sulfotransferase (HS2ST (AB024568)), Heparan sulfate glucosamine 6-O- sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). 29. The composition of embodiment 27 or embodiment 28, wherein the cell is deficient in chondroitin sulfate synthase 1 (ChSy 1). 30. The composition of any one of embodiments 27 to 29, wherein the cell is deficient in chondroitin sulfate. 31. The composition of any one of embodiments 27 to 30, wherein the cell is transgenic for one or more genes recited in Table 6. 32. The composition of any one of embodiments 27 to 31, wherein the cell is transgenic for one or more of DTDST sulfate anion transporter 1 (SLC26A2 (NP_000103)), PAPS synthetase-1 (ATP sulfurylase/APS kinase 1) (PAPSS1 (Y10387)), PAPS synthetase-2 (ATP sulfurylase/APS kinase 2) (PAPSS2 (AF074331)), PAPS transporter (AB107958), PAPS transporter 1 (SLC35B2 (Q8TB61.1)), PAPS transporter 2 (SLC35B3 (Q9H1N7.1)), UDP-GlcA transporter (SLC35D1 (NP_055954)), UDP-GlcNAc transporter (SLC35A3 (NP_036375)), UDP-Gal transporter (SLC35A2 (P78381)), UDP glucose dehydrogenase (UGDH (AAC36095)), UDP-glucose decarboxylase (UXS (AAK85410)), Xylosyltransferase I (XTI (AJ277441)), Xylosyltransferase II (XTII (AJ277442)), Galactosyltransferase I (34GalT7) (XGALT-1 (AB028600)), Galactosyltransferase II (β3GalT6) (GALT-2 (AY050570)), Glucuronosyltransferase I (GLCAT-1 (AB009598)), α-N-acetylglucosaminyltransferase I (EXTL1 (AH007206)), α-N-acetylglucosaminyltransferase I (EXTL2 (AF000416)), α-N-acetylglucosaminyltransferase I (EXTL3 (AF001690)), Exostosin glycosyltransferase 1 (EXT1 (579639)), Exostosin glycosyltransferase 2 (EXT2 (NM_000401)), N-deacetylase N-sulfotransferase 1 (NDST1 (U18918)), N-deacetylase N-sulfotransferase 2 (NDST2 (NM_003635)), N-deacetylase N-sulfotransferase 3 (NDST3 (AF074924)), N-deacetylase N-sulfotransferase 4 (NDST4 (AB036429)), C5 glucuronyl epimerase (C5EPI (XM_035390)), Heparan sulfate 2-O-sulfotransferase (HS2ST (AB024568)), Heparan sulfate glucosamine 6-O-sulfotransferase 1 (HS6ST1 (AB006179)), Heparan sulfate glucosamine 6-O-sulfotransferase 2 (HS6ST2 (NM_147174)), Heparan sulfate glucosamine 6-O-sulfotransferase 2 short (HS6ST2 (NM_147175)), Heparan sulfate glucosamine 6-O-sulfotransferase 3 (HS6ST3 (AF539426)), Heparan sulfate glucosamine 3-O-sulfotransferase 1 (HS3ST1 (AF019386)), Heparan sulfate glucosamine 3-O-sulfotransferase 2 (HS3ST2 (AF105375)), Heparan sulfate glucosamine 3-O-sulfotransferase 3A (HS3ST3A1 (AF105376)), Heparan sulfate glucosamine 3-O-sulfotransferase 3B (HS3ST3B1 (AF105377)), Heparan sulfate glucosamine 3-O-sulfotransferase 4 (HS3ST4 (AF105378)), Heparan sulfate glucosamine 3-O-sulfotransferase 5 (HS3ST5 (AF503292)), Heparan sulfate glucosamine 3-O-sulfotransferase 6 (HS3ST6 (AE00640)), Syndecan-1 (Sdc-1 (Hs.82109)), Syndecan-2 (fibroglycan) (Sdc-2 (Hs.1501)), Syndecan-3 (N-syndecan) (Sdc-3 (Hs.158287)), Syndecan-4 (ryudocan, amphiglycan) (Sdc-4 (Hs.252189)), Glypican-1 (Gpc-1 (Hs.328232)), Glypican-2 (cerebroglycan) (Gpc-2 (Hs.211701)), Glypican-3 (Gpc-3 (Hs.119651)), Glypican-4 (Gpc-4 (Hs.58367)), Glypican-5 (Gpc-5 (Hs.76828)), Glypican-6 (Gpc-6 (Hs.118407)), CD44 (epican) (CD44 (Hs.502328)), Perlecan (HSPG2) (Prl (Hs.211573)), Agrin (Agrn (Hs.273330)), and Serglycin (Sgc (Hs.451015)). 33. The composition of any one of embodiments 27 to 32, wherein the cell is genetically modified to be deficient for chondroitin sulfate synthesis (ChA27) and transgenic for Hs3st1. 34. The composition of any one of embodiments 27 to 33, wherein the cell comprises a cell line in Table 4. 35. The composition of any one of embodiments 27 to 34, wherein the cell produces a heparin composition substantially free from chondroitin sulfate. 36. The composition of any one of embodiments 27 to 35, wherein the cell produces a heparin with a defined pattern of sulfation. 37. The composition of any one of embodiments 27 to 36, wherein the cell produces a heparin that is at least 95% free from protein and nucleic acid contamination. 38. The composition of any one of embodiments 27 to 37, wherein the cell produces a hyper-sulfated heparan sulfate composition substantially free from chondroitin sulfate. 39. The composition of any one of embodiments 27 to 38, wherein the cell produces a hyper-sulfated heparan sulfate with a defined pattern of sulfation. 40. The composition of any one of embodiments 27 to 39, wherein the cell produces a hyper-sulfated heparan sulfate that is at least 95% free from protein and nucleic acid contamination. 41. The composition of any one of embodiments 27 to 40, wherein the cell is a mast cell, a CHO cell, a mouse embryonic fibroblast, a 293 cell, a HeLa cell, a human fibroblast, a human embryonic stem cell, a stem cell, a an F9 cell, a human cardiac-derived progenitor cell (hCMPC), a tumor cell, or other animal cell. 42. The composition of any one of embodiments 27 to 41, wherein the cell is from a mammal. 43. The composition of any one of embodiments 27 to 42, wherein the cell is from a human. 44. A method of preparation of a substantially pure heparin or hyper-sulfated heparan sulfate comprising use of the composition of any one of embodiments 27 to 43, wherein the method comprises the steps: (a) growing the cells of any one of embodiments 27 to 43, using an appropriate growth media, (b) isolating the growth media from the cells by centrifugation. 45. The method of embodiment 44, wherein the method comprises fractionating the mixture by ion exchange column. 46. The method of embodiment 44 or embodiment 45, wherein the method comprises removing contaminating nucleic acids by nuclease digestion. 47. The method of any one of embodiments 44 to 46, wherein the method comprises removing contaminating proteins by protease digestion. 48. The method of any one of embodiments 44 to 47, wherein the method comprises fractionating the resulting product by ion exchange. 49. The method of any one of embodiments 44 to 48, wherein the method comprises affinity chromatography. 50. The method of any one of embodiments 44 to 49 wherein the method comprises desalting. 51. The method of any one of embodiments 44 to 50, wherein the heparin or hypersulfated heparan sulfate is substantially free from chondroitin sulfate. 52. The method of any one of embodiments 44 to 51, wherein the method does not require the use of a chondroitinase. 53. The method of any one of embodiments 44 to 52, wherein the heparin or hyper-sulfated heparan sulfate is at least 95% free from protein and nucleic acid contamination. 54. A method of making a cell line capable of producing a heparin or a hyper-sulfated heparan sulfate comprising genetically modifying a cell line to be transgenic or deficient for a gene of Table 6. 55. The method of embodiment 54, wherein the cell line does not produce chondroitin sulfate. 56. A kit comprising the cell of any one of embodiments 27 to 43 and instructions for use in preparing a cell-line produced heparin. 57. The kit of embodiment 56, wherein the kit comprises instructions for the method of any one of embodiments 44 to 53. 58. A method of treating a thrombosis in an individual in need thereof comprising administering an effective amount of the composition of any one of embodiments 1 to 12 or embodiments 14 to 25 or the pharmaceutical composition of embodiment 13 or embodiment 26. 59. The method of embodiment 58, wherein the thrombosis comprises, venous thrombosis, deep vein thrombosis, portal vein thrombosis, renal vein thrombosis, jugular vein thrombosis, Budd-Chiari syndrome, Paget-Schroetter disease, Cerebral venous sinus thrombosis, Cavernous sinus thrombosis, arterial thrombosis, stroke, myocardial infarction or Hepatic artery thrombosis. 60. The composition of any one of embodiments 1 to 12 or embodiments 14 to 25 or the pharmaceutical composition of embodiment 13 or embodiment 26 for use in treating a thrombosis.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Genetically Altered Cell Lines and Hypersulfated Heparan Sulfate Compositions

Cell Culture

CHO—S cells (Life Technologies) were routinely cultured in 30 ml of CD CHO Expression Medium (Life Technologies) with 8 mM GlutaMAX™ (Life Technologies) in 125 ml shaker culture flasks (VWR) on a rotating platform (130 rpm) at 37° C. and 5% $CO_2$. For GAG production, the cells were cultured as described. Briefly, cells were seeded at $0.2\times10^6$ cells/ml in CD CHO Expression medium plus 8 mM GlutaMAX™. On days 3, 5 and 7 three milliliters of CD CHO EfficientFeed™ B were added to the flaks. The conditioned medium was harvested on day 10. The cells were spun out of the medium (5000 rpm, 10 minutes performed twice) and the supernatant was stored at −20° C. until further processing. This has been scaled up to multiple 1 μliter flasks (300 ml each) to produce large batches.

CRISPR Cas Modification of CHO—S Cells

Mutation of GAG biosynthetic genes in CHO—S cells was accomplished by transient coexpression of Cas9 with a guide RNA sequence. Guide RNA (sgRNA) sequences were designed using "CRISPy" described in the reference Rhonda C, Pedersen L E, et al. *Biotechnol Bioeng*. 2014 August; 111(8):1604-16. Oligonucleotides for each sgRNA were purchased (ValueGene) and ligated into pSpCas9(BB)-2A-puro (Addgene). CHO—S cells were transfected with the ligated plasmid using FreeStyle™ MAX Transfection Reagent (Life Technologies). After 48 hours of transfection, the medium was changed to regular growth medium and the cells were allowed to recover for 24 hours. DNA was extracted from the cells using QuickExtract™ DNA extraction solution (Epicentre). The targeted genomic regions were amplified by PCR using Herculase II (Aglient Technologies) and PCR primers. Genetic mutations were detected using the SURVEYOR™ nuclease assay (Integrated DNA Technologies).

Clonal cell lines were created by limiting dilution cloning of the transfected population. Cells were diluted to 10 cells/ml into CD FortiCHO™ medium (Life Technologies) with 6 mM GlutaMAX™ (Life Technologies) and 200 μl were plated into each well of 96-well plates. The plates were incubated at 37° C., 5% $CO_2$ in a humidified chamber. After 12 days, the plates were checked for colony formation. Colonies were transferred sequentially to 24-well plates and 6-well plates before screening by flow cytometry for cell surface chondroitin sulfate using antibody 2B6 or alteration of heparan sulfate by FGF2 binding. Colonies that were deficient in chondroitin sulfate or having altered FGF2 binding were transferred to 20 ml of CD CHO Expression medium (Life Technologies) with 8 mM GlutaMAX™ for further growth and analysis.

To determine the specific mutation in a clonal cell line, the targeted genomic region was PCR amplified. The purified PCR product was cloned into pUC19, which was subsequently transformed into *E. coli* and isolated from plated colonies for sequencing (Genewiz).

Detection of Cell Surface Chondroitin Sulfate

Cell surface chondroitin sulfate was detected by flow cytometry using the antibody 2B6 (Amsbio). This antibody is specific to the 4-O-sulfated chondroitin sulfate stub epitope revealed by chondroitinase ABC digestion. $0.2\times10^6$ cells were placed in each well of a V-bottom 96-well plate (Corning). For screening colonies in 6-well plates, 200 μl of culture medium was transferred to the 96-well plate. The cells were washed into fresh culture medium with 10 mU/ml chondroitinase ABC (Amsbio) and incubated for 30 minutes at 37° C. A second well was incubated with fresh culture medium alone as a control. Following digestion, the cells were washed twice with 200 μl of chilled dPBS (Lonza) and incubated with a 1:200 dilution of 2B6 in dPBS plus 0.1% BSA (Sigma) for 1 hour at 4° C. The cells were then washed again and incubated with 1:100 dilution of goat anti-mouse IgG-Cy3 (Jackson ImmunoResearch) for 1 hour at 4° C. The cells were washed again and analyzed by flow cytometry on a Guava® PCA-96.

Detection of FGF2 Bound to the Cell Surface

Recombinant human FGF2 (Shenandoah Biotechnology) was bound to a heparin-Sepharose® column in dPBS and biotinylated using 0.6 mg/ml sulfo-NHS-LC-biotin (Thermo) in dPBS. After 1 hour incubation at room temperature, the column was washed with dPBS and then bound biotin-FGF2 was eluted in dPBS plus 2 M NaCl. This material was subsequently used to measure FGF2 binding to the cell surface.

$0.2\times10^6$ cells (or 200 μl of culture medium when screening colonies) were transferred to a 96-well V-bottom plate (Corning) and washed into dPBS. The cells were incubated with a 1:500 dilution of biotin-FGF2 in PBS with 0.1% BSA for 1 hour at 4° C. The cells were washed and incubated with a 1:1000 dilution of streptavidin-phycoerythrin (eBioscience) in PBS with 0.1% BSA for 30 minutes at 4° C. After a final wash in dPBS, the cells were analyzed by flow cytometry on a Guava® PCA-96.

Glycosaminoglycan Purification

Glycosaminoglycan (GAG) was purified from CHO—S conditioned medium. First, the conditioned medium was fractionated on DEAE-Sephacel™, equilibrated and washed with 50 mM NaAcO, 250 mM NaCl, pH 6.0, and eluted with 50 mM NaAcO, 1 M NaCl, pH 6.0. For GAG preparation from cells with Ndst1 and Ndst2 targeted, the concentration of NaCl was lowered to 150 mM in the equilibration/wash buffer. The resulting eluate was diluted 6-fold in MilliQ® water. Then, $CaCl_2$ was added to 5 mM. 60 Kunitz DNase I (Sigma) was added and allowed to incubate overnight at 37° C. The following day, Pronase (Sigma) was added to 0.5 mg/ml and allowed to incubate for 3 hours at 37° C. The preparation was again purified over DEAE as before and desalted on a PD-10 column equilibrated in 10% ethanol. The desalted GAG was dried on a SpeedVac™ and stored at −20° C. In some cases, the GAG was beta-eliminated by resuspending dried GAG in 0.4 M NaOH and incubating overnight at 4° C. The solution was neutralized with addition of acetic acid, desalted on PD-10 and dried on a SpeedVac™

GAG Quantification

GAG was quantified by carbazole assay as previously described. Briefly, up to 100 μl of purified GAG was incubated with 10 μl of 4 M ammonium sulfamate and 500 μl of 25 mM sodium tetraborate in $H_2SO_4$ at 950 C for 5 minutes. After cooling to room temperature, 20 μl of 0.1% carbazole in ethanol was added and the samples were heated to 950 C for 15 minutes. Glucuronic acid in the samples was measured by absorbance at 520 nM. Samples prepared in parallel using 0-10 g of glucuronic acid served as the standard curve.

To measure chondroitin sulfate or heparan sulfate production specifically, purified GAG was digested exhaustively with heparin lyases or chondroitinase ABC (Amsbio) and remaining GAG was repurified and quantified by carbazole assay. Heparin lyases were produced as described previously. For chondroitin sulfate quantification, digestion was performed in 50 mM NaAcO, 5 mM CaAcO, pH 7.0 with 2.5 mU/ml each heparin lyases I, II and III, overnight at 37° C. For heparan sulfate quantification, digestion was performed in 50 mM Tris, 50 mM NaAcO, pH 8.0 with 5 mU/ml chondroitinase ABC, overnight at 37° C.

Alternatively, heparan sulfate and chondroitin sulfate in the samples were detected by lyase digestion UV absorbance. 40 μl of purified GAG was diluted 5 fold with water and transferred to a 96-well UV transparent plate. 22 μl of 10× heparin lyase (500 mM NaAcO, 5 mM CaAcO, pH 7.0) or 10× chondroitinase buffer (500 mM Tris, 500 mM NaAcO, pH 8.0) were added to the well. A baseline absorbance measurement was made at 250 nm before addition of either 1 mU each heparin lyases I, II, III or 1 mU chondroitinase ABC. The wells were sealed with parafilm and incubated at 37° C. for 30 minutes before taking another measurement at 250 nm. The measurement was repeated after 5 minutes to verify that the reaction had gone to completion.

Heparan Sulfate Disaccharide Analysis

Disaccharide composition of heparan sulfate was determined by GRIL-LC/MS as previously described. Briefly, for each analysis, 5 g of purified heparan sulfate was dried down and resuspended in 100 μl heparin lyase buffer (50 mM NaAcO, 5 mM CaAcO, pH 7.0) with 2 mU/ml each heparin lyases I, II and III. Samples were digested overnight at 37° C. and then dried on a SpeedVac™. Each sample was aniline tagged by incubation with aniline and reductant. Reductant consisted of 150 mg $NaCNBH_4$ (Sigma) dissolved in 1.4 ml of DMSO (Sigma) and 0.6 ml of glacial acetic acid (Fisher). 17 μl of aniline (Sigma) was added to each sample followed immediately by 17 μl of reductant. The sample was vortexed to bring the dried heparan sulfate into solution and then incubated overnight at 37° C. The tagged sample was then dried to completion on a SpeedVac™ and stored at −20° C. until analysis by LC/MS by the Glycotechnology Core Resource at the University of California, San Diego.

Preparation of Extracellular Matrix (ECM)

To prepare gelatin-coated substrates, tissue culture plates were incubated with 0.1% gelatin for 30 minutes. Established procedures were used for preparing the cell-free decellularized matrix. Briefly, ChA27 derived cell lines were cultured in wells of a 24-well plate until highly confluent. Cells were washed twice with 1 ml PBS followed by two washes with 1 ml of wash buffer I (100 mM Na2HPO4, pH 9.6, 2 mM MgCl2, 2 mM EGTA). 1 ml lysis buffer (8 mM Na2HPO4, pH 9.6, 1% NP-40) was added to each well and incubated at 37° C. for 15 minutes; this was then removed and replaced with 1 ml fresh lysis buffer and incubation was continued for 40-60 minutes. Matrices were washed twice with 1 ml wash buffer II (300 mM KCl, 10 mM Na2HPO4, pH 7.5) and four times with 1 ml dH2O. Matrix could be stored in PBS at 4° C. for a few weeks.

Example 2: Genes for Overexpression or Deletion for Heparin Production

Gene expression profiles are determined in cells and tissues producing large amounts of heparin. Cells and tissues include mast cells, lung tissue, gastrointestinal tissue, and connective tissue. Cells known to not produce heparin are used as a control.

Mast cells are collected and rinsed with PBS once. Total RNA of mast cell samples is prepared by using TRIZOL™ reagent according to the instruction provided by the manufacturer (Life Technology, Carlsbad, Calif., USA). Poly(A) mRNA is purified by oligo(dT) beads (Life Technology, Carlsbad, Calif., USA).

The purified mRNA samples are fragmented to 200 bp-500 bp and reverse-transcribed using random hexamers. Short cDNA fragments are purified with QiaQuick® PCR extraction kit (Qiagene, Hilden, Germany) and followed by end repair and poly (A) addition. Sequencing adaptors are then added to the ends of the 3' A-tailed cDNA fragments. After size selection and PCR amplification of the sequencing fragment libraries, 51 bp or 91 bp pair-end reads are generated using an Illumina HiSeq™ 2000 (Illumina, San Diego, Calif., USA). Gene expression profiles are generated from RNAseq data.

Genes overexpressed in heparin producing cells and tissues are chosen for overexpression in genetically altered cell lines. Genes underexpressed, or not expressed in heparin producing cells and tissues are chosen for knockout in genetically altered cell lines.

Example 3: Genetically Altered Cell Lines for Heparin Production

Cell Culture

CHO—S cells (Life Technologies) are routinely cultured in 30 ml of CD CHO Expression Medium (Life Technologies) with 8 mM GlutaMAX™ (Life Technologies) in 125 ml shaker culture flasks (VWR) on a rotating platform (130 rpm) at 37° C. and 5% $CO_2$. For heparin production, the cells are cultured as described. Briefly, cells are seeded at $0.2\times10^6$ cells/ml in CD CHO Expression medium plus 8 mM GlutaMAX™. On days 3, 5 and 7 three milliliters of CD CHO EfficientFeed™ B are added to the flasks. The conditioned medium is harvested on day 10. The cells are spun out of the medium (5000 rpm, 10 minutes performed twice) and the supernatant is stored at −20° C. until further processing. This is been scaled up to multiple 1 μliter flasks (300 ml each) to produce large batches.

CRISPR/Cas Modification of CHO—S Cells

Mutation of GAG biosynthetic genes in CHO—S cells is accomplished by transient coexpression of Cas9 with a guide RNA sequence. Guide RNA (sgRNA) sequences are designed using "CRISPy" described in the reference Rhonda C, Pedersen L E, et al. *Biotechnol Bioeng*. 2014 August; 111(8):1604-16. Oligonucleotides for each sgRNA are purchased (ValueGene) and ligated into pSpCas9(BB)-2A-puro (Addgene). CHO—S cells are transfected with the ligated plasmid using FreeStyle™ MAX Transfection Reagent (Life Technologies). After 48 hours of transfection, the medium is changed to regular growth medium and the cells are allowed to recover for 24 hours. DNA is extracted from the cells using QuickExtract™ DNA extraction solution (Epicentre). The targeted genomic regions are amplified by PCR using Herculase II (Aglient Technologies) and PCR primers. Genetic mutations are detected using the SURVEYOR™ nuclease assay (Integrated DNA Technologies).

Clonal cell lines are created by limiting dilution cloning of the transfected population. Cells are diluted to 10 cells/ml into CD FortiCHO™ medium (Life Technologies) with 6 mM GlutaMAX™ (Life Technologies) and 200 μl are plated into each well of 96-well plates. The plates are incubated at 37° C., 5% $CO_2$ in a humidified chamber. After 12 days, the plates are checked for colony formation. Colonies are transferred sequentially to 24-well plates and 6-well plates before screening by flow cytometry for heparin production by analyzing binding of cells to Antithrombin III (AT3). Colonies that produce heparin are transferred to 20 ml of CD CHO Expression medium (Life Technologies) with 8 mM GlutaMAX™ for further growth and analysis.

To determine the specific mutation in a clonal cell line, the targeted genomic region is PCR amplified. The purified PCR product is cloned into pUC19, which is subsequently transformed into *E. coli* and isolated from plated colonies for sequencing (Genewiz).

Detection of Heparin

Heparin expression is detected by Antithrombin III (AT3) binding by flow cytometry. Increased AT3 binding activity is detectable by anti-AT3 antibody binding to the surfaces of transfected cells.

Heparin Purification

Heparin is purified from CHO—S conditioned medium. First, the conditioned medium is fractionated on DEAE-Sephacel™, equilibrated and washed with 50 mM NaAcO, 250 mM NaCl, pH 6.0, and eluted with 50 mM NaAcO, 1 M NaCl, pH 6.0. For heparin preparation from cells with Ndst1 and Ndst2 targeted, the concentration of NaCl is lowered to 150 mM in the equilibration/wash buffer. The resulting eluate is diluted 6-fold in MilliQ® water. Then, $CaCl_2$ is added to 5 mM. 60 Kunitz DNase I (Sigma) is added and allowed to incubate overnight at 37° C. The following day, Pronase (Sigma) is added to 0.5 mg/ml and allowed to incubate for 3 hours at 37° C. The preparation is again purified over DEAE as before and desalted on a PD-10 column equilibrated in 10% ethanol. The desalted heparin is dried on a SpeedVac™ and stored at −20° C. In some cases, the heparin is beta-eliminated by resuspending dried GAG in 0.4 M NaOH and incubating overnight at 4° C. The solution is neutralized with addition of acetic acid, desalted on PD-10 and dried on a SpeedVac™ Heparin Quantification Heparin is quantified by carbazole assay as previously described. Briefly, up to 100 μl of purified heparin is incubated with 10 μl of 4 M ammonium sulfamate and 500 μl of 25 mM sodium tetraborate in $H_2SO_4$ at 950 C for 5 minutes. After cooling to room temperature, 20 μl of 0.1% carbazole in ethanol is added and the samples are heated to 950 C for 15 minutes. Glucuronic acid in the samples is measured by absorbance at 520 nM. Samples prepared in parallel using 0-10 g of glucuronic acid serve as the standard curve.

To measure heparin production specifically, purified heparin is digested exhaustively with heparin lyases remaining GAG is repurified and quantified by carbazole assay. Heparin lyases are produced as described previously. For heparin quantification, digestion is performed in 50 mM Tris, 50 mM NaAcO, pH 8.0 with 5 mU/ml chondroitinase ABC, overnight at 37° C.

Alternatively, heparin in the samples is detected by lyase digestion UV absorbance. 40 μl of purified heparin is diluted 5 fold with water and transferred to a 96-well UV transparent plate. 22 μl of 10× heparin lyase (500 mM NaAcO, 5 mM CaAcO, pH 7.0) is added to the well. A baseline absorbance measurement is made at 250 nm before addition of either 1 mU each heparin lyases I, II, and III. The wells are sealed with parafilm and incubated at 37° C. for 30 minutes before taking another measurement at 250 nm. The measurement is repeated after 5 minutes to verify that the reaction has gone to completion.

Heparin Disaccharide Analysis

Disaccharide composition of heparin is determined by GRIL-LC/MS as previously described. Briefly, for each analysis, 5 g of purified heparan sulfate is dried down and resuspended in 100 μl heparin lyase buffer (50 mM NaAcO, 5 mM CaAcO, pH 7.0) with 2 mU/ml each heparin lyases I, II and III. Samples are digested overnight at 37° C. and then dried on a SpeedVac™. Each sample is aniline tagged by incubation with aniline and reductant. Reductant consists of 150 mg $NaCNBH_4$ (Sigma) dissolved in 1.4 ml of DMSO (Sigma) and 0.6 ml of glacial acetic acid (Fisher). 17 μl of aniline (Sigma) is added to each sample followed immediately by 17 μl of reductant. The sample is vortexed to bring the dried heparin into solution and then incubated overnight at 37° C. The tagged sample is then dried to completion on a SpeedVac™ and stored at −20° C. until analysis by LC/MS by the Glycotechnology Core Resource at the University of California, San Diego.

Example 4: Measurin2 ATIII Bindin2 in Genetically Modified Cell Lines

CHO—S cells lacking chondroitin sulfate synthesis (ChA27) were transfected with an Hs3st1 expression plasmid. The cells were selected with an antibiotic and then limiting dilution cloning was performed to obtain single cell colonies. Since Hs3st1 is required to create the antithrombin (ATIII) binding site on heparan sulfate, the untransfected cells, selected population and a single colony were tested for expression of Hs3st1 by challenging the cells to bind ATIII and then analyzing by flow cytometry.

Cells were incubated with 0 or 100 nM of ATIII (1 hour, 4 deg). Then, washed and incubated with a goat IgG antibody against human ATIII (1 ug/ml, 1 hour, 4 deg).

Finally, the cells were washed and incubated with an anti-goat IgG-Cy3 conjugate (1:200 dilution, 30 minutes, 4 deg).

Figure 2:
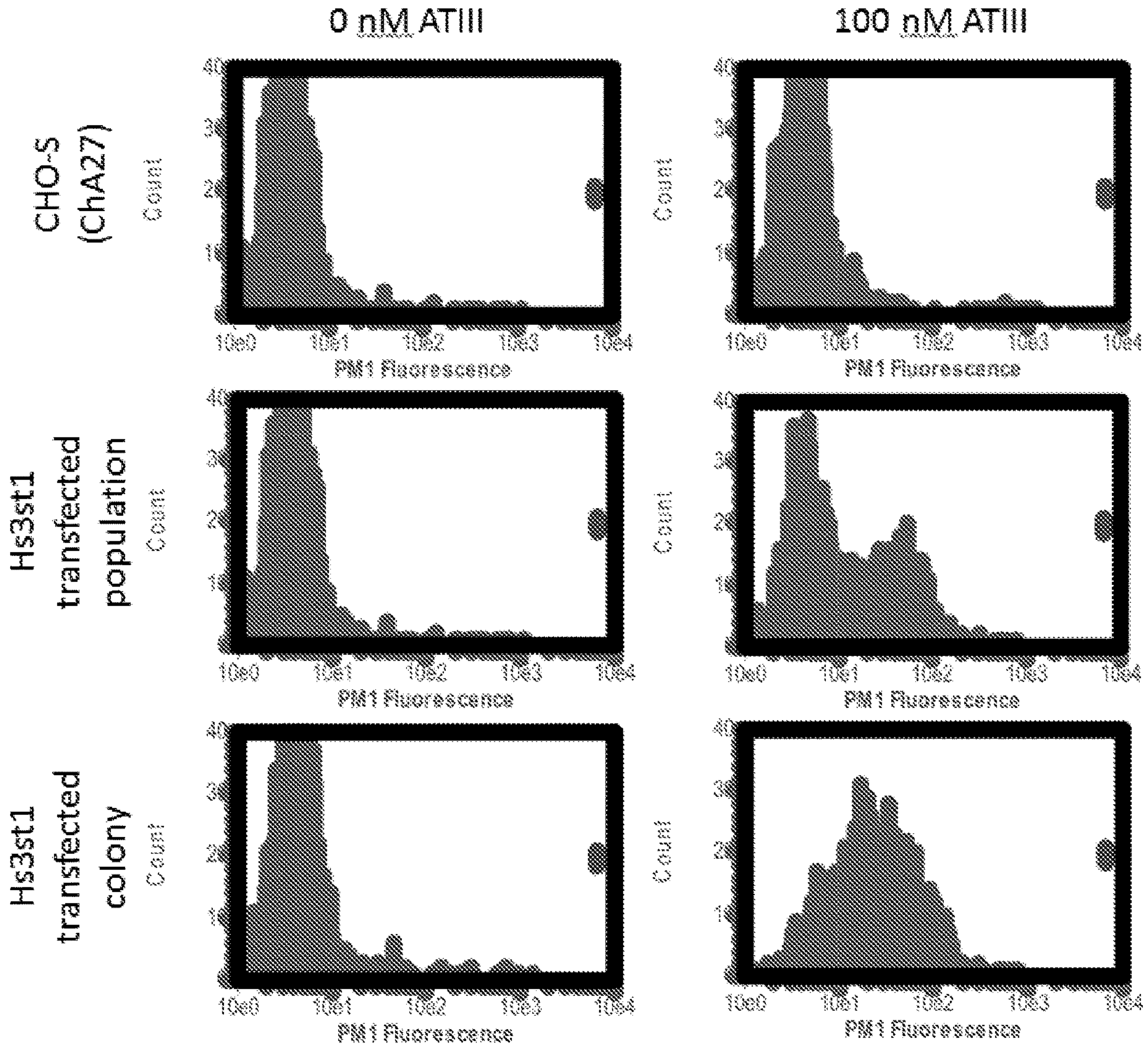
FIG. 2 shows elevated ATIII binding in cells expressing Hs3st1.
Figure 3A:
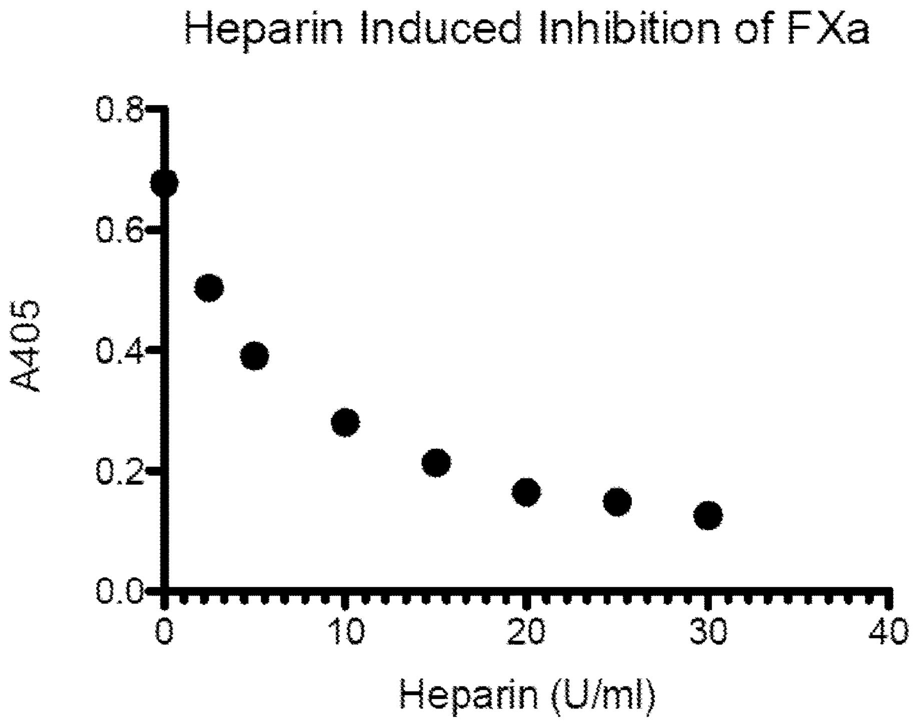
FIG. 3A shows the heparin standard curve in a Factor Xa assay.
Figure 3B:
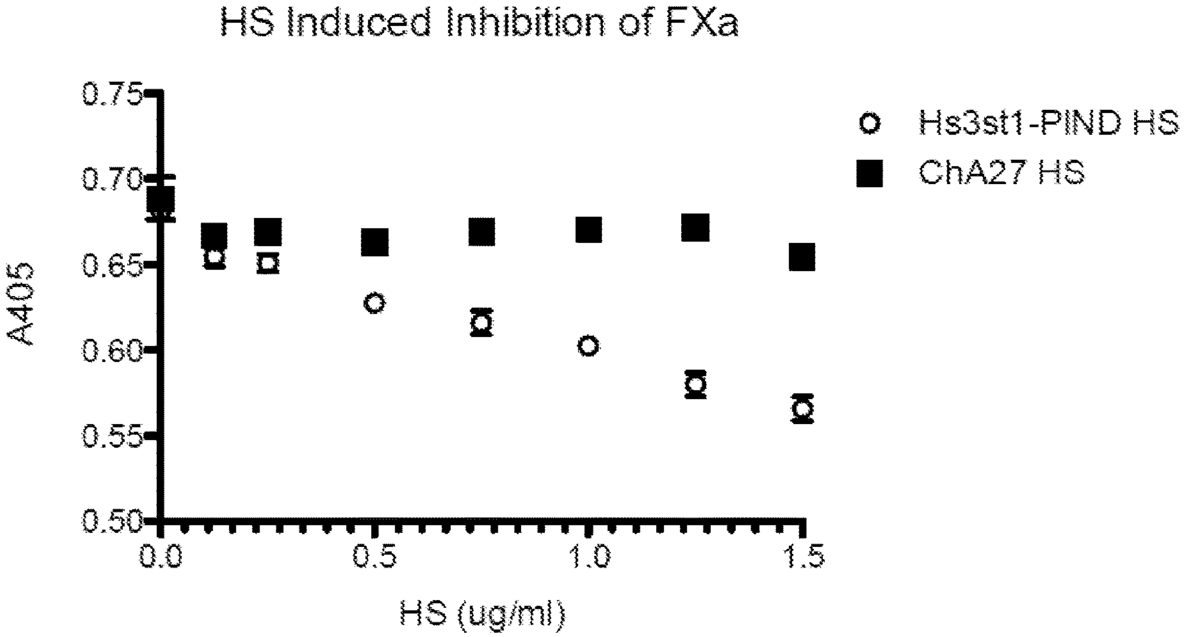
FIG. 3B shows the cell sample results of a Factor Xa assay.

FIG. 2 shows the selected population having two peaks indicating that a subset of the cells express Hs3st1. The colony is a single peak with elevated ATIII binding demonstrating Hs3st1 expression.

Example 5: Measuring Factor Xa Inhibition in Genetically Modified Cell Lines

A specific pentasaccharide sequence found in heparin binds to antithrombin. Binding causes a conformational change in antithrombin which increases its ability to inactivate FactorXa. Heparan sulfate produced by CHO cells lacks the critical 3-O-sulfate group found in the pentasaccharide sequence. CHO cells were engineered to lack chondroitin sulfate synthesis (ChA27) and were transfected with Hs3st1. The activity of heparan sulfate produced by the engineered cell line was compared to heparan sulfate from the parental CHO cells and pharmaceutical grade heparin using a Factor Xa inactivation assay.

Various concentrations of heparin/heparan sulfate from the cells were mixed with antithrombin. Then, Factor Xa was added and the samples were incubated at room temperature. A chromogenic substrate for Factor Xa was added and incubated at room temperature. Absorbance at 405 nm was measured.

Heparan sulfate from CHO cells showed no inhibitory activity toward Factor Xa. Heparan sulfate from the engineered cell line was able to inactivate Factor Xa. The potency of heparan sulfate from the engineered cell line is much lower than pharmaceutical heparin.

Example 6: Liquid Chromatography/Mass Spectrometry of Heparan and Heparan Sulfate Compositions Digestion with heparin lyases I, II and III reduces heparan sulfate to its component disaccharides except for a few 3-O-sulfate containing structures that are resistant giving a tetrasaccharide product. The tetrasaccharides are also found in heparin and are characteristic of anticoagulant heparin/heparan sulfate. The disaccharide composition of the glycosaminoglycan as well as the presence of the resistant tetrasaccharides can be determined by LCMS.

To verify the presence of heparin lyase structures that are indicative of anticoagulant heparan sulfate, heparan sulfate is purified from medium conditioned by CHO cells or CHO cells expressing the heparan sulfate 3-O-sulfotransferase. The heparan sulfate is exhaustively digested with a mixture of heparin lyase I, II and III then dried and resuspended in LCMS buffer. The samples are then run on a reverse phase column and detected by mass spectrometry.

The cell line expressing the 3-O-sulfotransferase produces heparan sulfate containing resistant tetrasaccharides, which indicates that the heparan sulfate contains anticoagulant structures. These structures are absent in the heparan sulfate produced by the parental CHO cell line but are abundant in heparin. These results are consistent with the enhanced binding of antithrombin to the surface of the engineered cell line and the anti-Factor Xa activity of heparan sulfate produced by the engineered cell line.

Example 7: Treatment of Venous Thrombosis

A subject suffering from venous thrombosis due to atrial fibrillation is given continuous intravenous administration of cell-line produced heparin to treat the venous thrombosis. Coagulation tests are performed before and during treatment to determine activated partial thromboplastin time (APTT) and sufficient heparin has been administered when APTT is 1.5 to 2 times the untreated value. A dose of 20,000 to 40,000 units is administered in 1,000 ml of isotonic sodium chloride solution per day.

A clinical trial is conducted to determine the efficacy of cell-line produced heparin compared to pharmaceutical heparin preparations. Fifty subjects suffering from venous thrombosis are treated with either cell-line produced heparin or pharmaceutical heparin in a randomized trial. Patients treated with either form of heparin are administered 20,000 to 40,000 units in 1,000 ml of isotonic sodium chloride per day until desired APTT is reached. Primary outcome measures are improvement of blood flow in lower extremity experiencing venous thrombosis (time frame: hospital admission through three months post discharge). Secondary outcome measures are adverse events associated with use of cell-line produced heparin and pharmaceutical heparin (time frame: hospital admission through discharge).

Inclusion criteria include: age >18 years, admission to the hospital with venous thrombosis. Exclusion criteria include age <18 years, inability to obtain informed consent, patient has history of a bleeding disorder, and patient currently on anticoagulant medication.

Individuals given cell-line produced heparin have as good or better outcomes than individuals given pharmaceutical heparin. No adverse events are observed in either group.

Example 8: Disaccharide Composition of Engineered Cell Lines

CHO cells were genetically engineered to knock out chondroitin sulfate production (ChA27). The ChA27 CHO cell line was further modified using Cas9 targeted to knock out Ndst1, Ndst2, Hs2st or Glce. Alternatively, Ndst1 or Ndst2 were overexpressed in the cell line by transfection with a mammalian expression plasmid followed by antibiotic selection. Heparan sulfate was purified from the conditioned medium from each cell type. The disaccharide composition of the heparan sulfate was determined by LCMS after complete digestion by heparin lyases and aniline tagging. Isotopically labeled mass standards were used to quantify the abundance of each type of disaccharide.

Figure 4A:
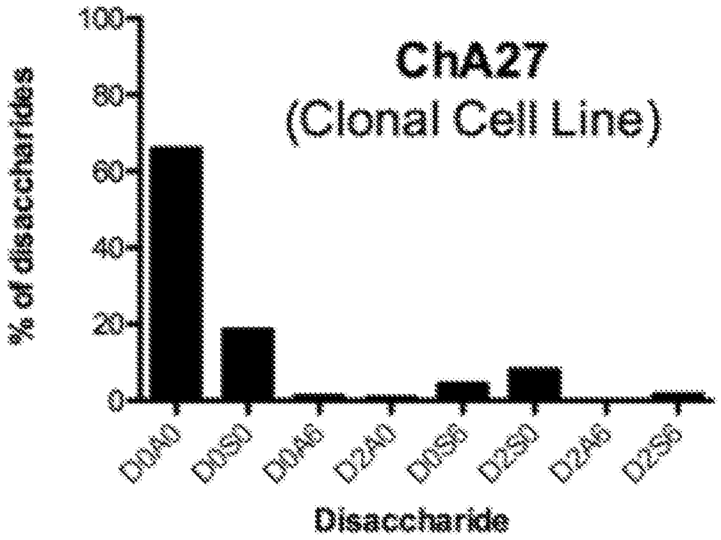
FIG. 4A shows disaccharide composition for ChA27 knockout cells.
Figure 4B:
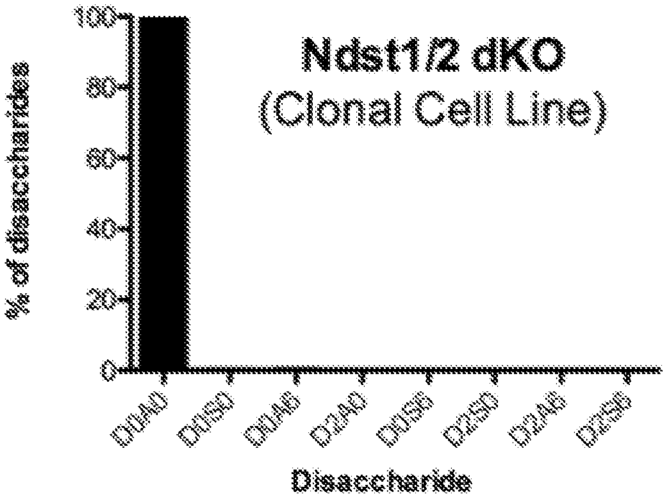
FIG. 4B shows disaccharide composition for Ndst1/Ndst2 double knockout cells.
Figure 4C:
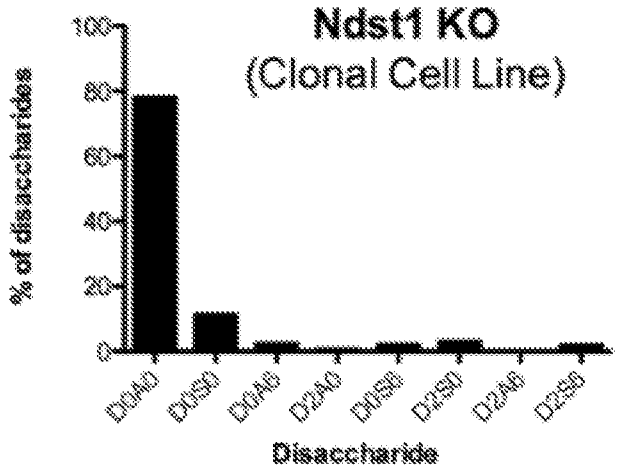
FIG. 4C shows disaccharide composition for Ndst1 knockout cells.
Figure 4D:
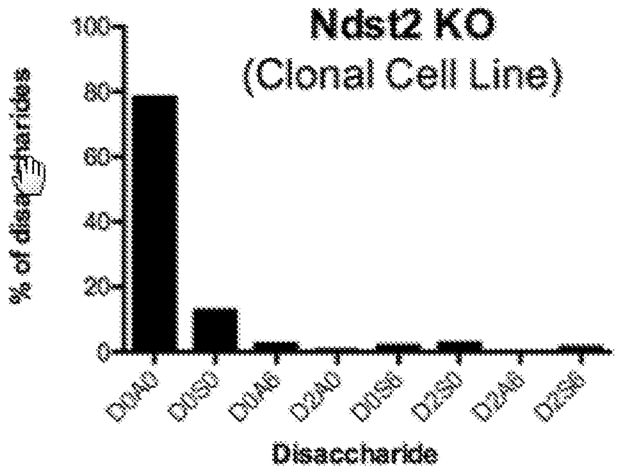
FIG. 4D shows disaccharide composition for Ndst2 knockout cells.
Figure 4E:
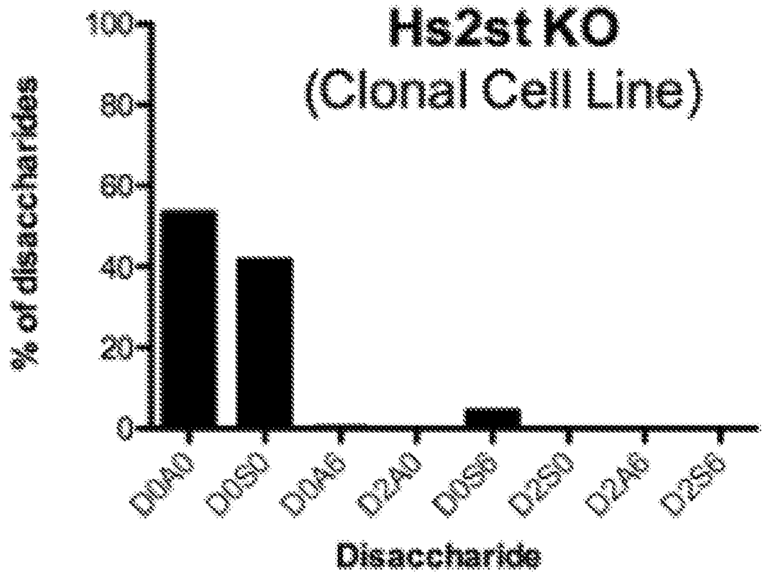
FIG. 4E shows disaccharide composition for Hs2st knockout cells.
Figure 4F:
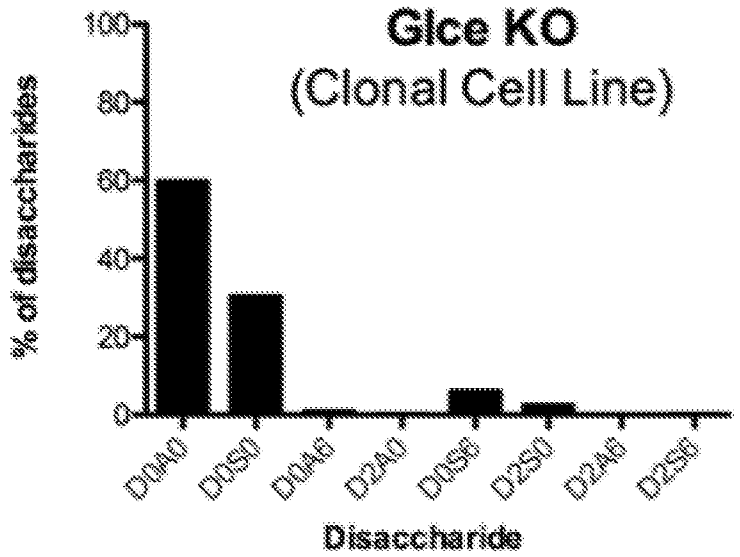
FIG. 4F shows disaccharide composition for Glce knockout cells.
Figure 4G:
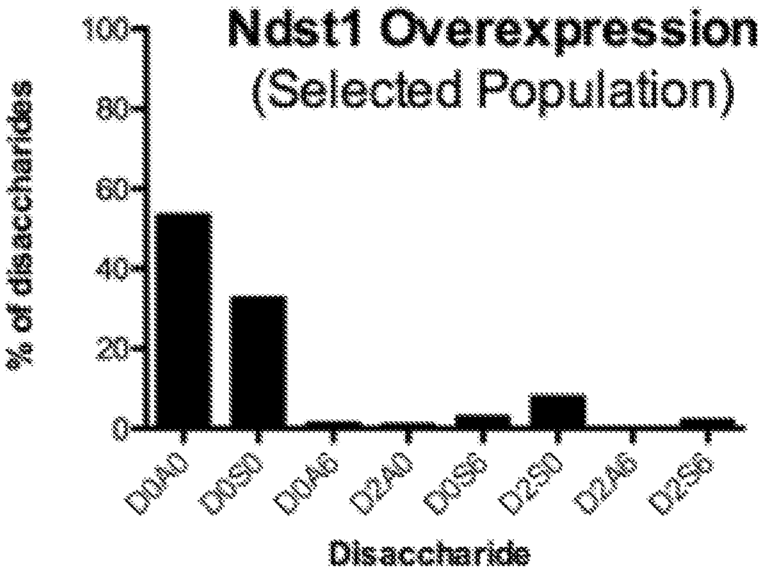
FIG. 4G shows disaccharide composition for Ndst1 overexpression cells.
Figure 4H:
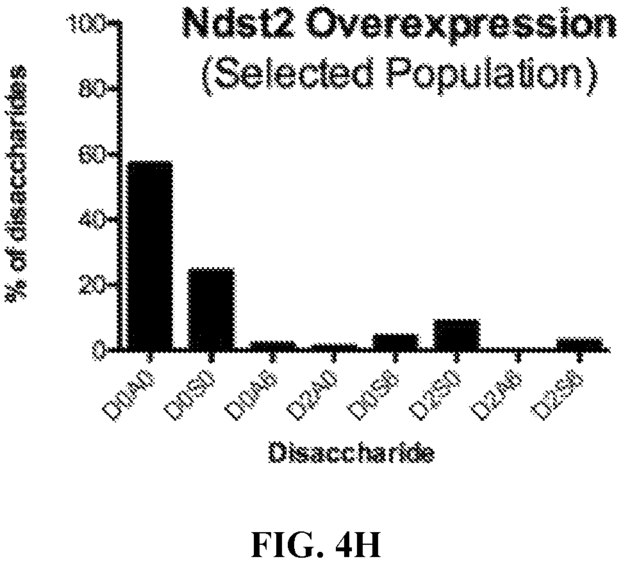
FIG. 4H shows disaccharide composition for Ndst2 overexpression cells.

Data for the ChA27 CHO cell line is shown in FIG. 4A. Knock out of Ndst1 and/or Ndst2 (FIG. 4B, FIG. 4C, FIG. 4D) resulted in reduction of all types of sulfate. Knock out of Hs2st (FIG. 4E) and Glce (FIG. 4F) resulted in reduction of α-sulfation and increase of N-sulfation. Overexpression of Ndst2 (FIG. 4H) resulted in increased N-sulfation and O-sulfation while overexpression of Ndst1 (FIG. 4G) resulted in increased N-sulfation and decreased 6-O-sulfation.

In FIGS. 4A-4F, to simplify the representation of constituent disaccharides, a disaccharide structure code (DSC) is used. In DSC, D designates a delta 4,5-unsaturated uronic acid. The N substituent is either A or S for acetate or sulfate, respectively. The presence and location of ester-linked sulfate groups are depicted by the number of the carbon atom on which the sulfate group is located or by 0 if absent. For example, D2S6 refers to a disaccharide composed of 2-sulfo-uronic acid-N-sulfoglucosamine-6-sulfate that has a delta 4,5-double bond in the uronic acid.

Example 9: Heparan Sulfate Competition Assay

Figure 5:
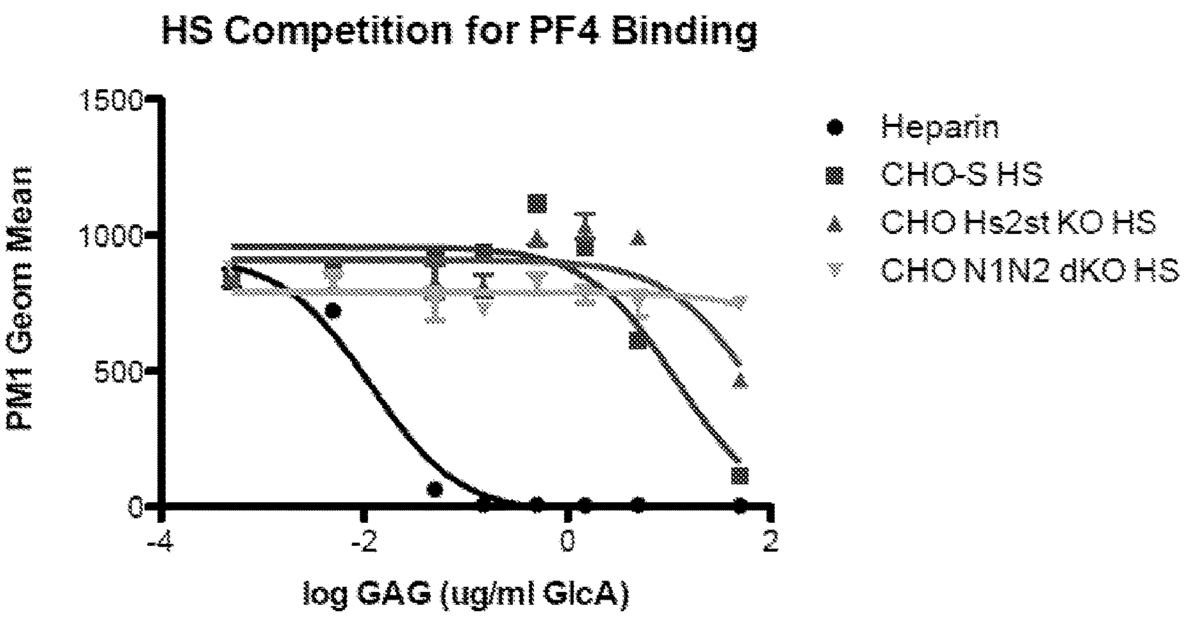
FIG. 5 shows binding of CHO cell heparan sulfate to platelet factor 4.

CHO cells were incubated with platelet factor 4 in the presence of various concentrations of heparin or heparan sulfates derived from engineered CHO cells. The heparan sulfates used were purified from ChA27, ChA27 Hs2st knockout and ChA27 Ndst1/Ndst2 double knockout cell lines. Competition of platelet factor 4 away from the cell surface was determined by a loss of signal measured by flow cytometry. EC50s were calculated by fitting a curve to the binding data. Data shown in FIG. 5 and

TABLE 2

Table 2 EC50 values for heparan sulfate competition assay

| Protein | Heparin | ChA27 | Hs2st KO | Glce KO | Ndst1 KO | Ndst2 KO |
|---|---|---|---|---|---|---|
| | EC50s (μg/ml GlcA) | | | | | |
| ATIII | 3.9 | N.D. | N.D. | N.D. | N.D. | N.D. |
| FGF2 | 0.09 | 0.7 | 36.9 | 5.2 | 7.3 | 19.6 |
| PF4 | 0.08 | 10.8 | 102.3 | 16.0 | 89.0 | 35.4 |
| VEGF | 0.10 | 6.6 | 130.6 | 166.3 | 37.7 | 58.4 |

Fibroblast growth factor 2 (FGF2), antithrombin III (ATIII), platelet factor 4 (PF4) and vascular endothelial growth factor (VEGF) were incubated with CHO cells in the presence of heparin or CHO cell derived heparan sulfates. EC50 values were calculated from competition curves.

FGF2 and PF4 affinity were especially reduced with loss of 2-O-sulfation while VEGF was most sensitive to loss of epimerase.

Example 10: Reproducibility of Heparan Sulfate Production

Figure 6:
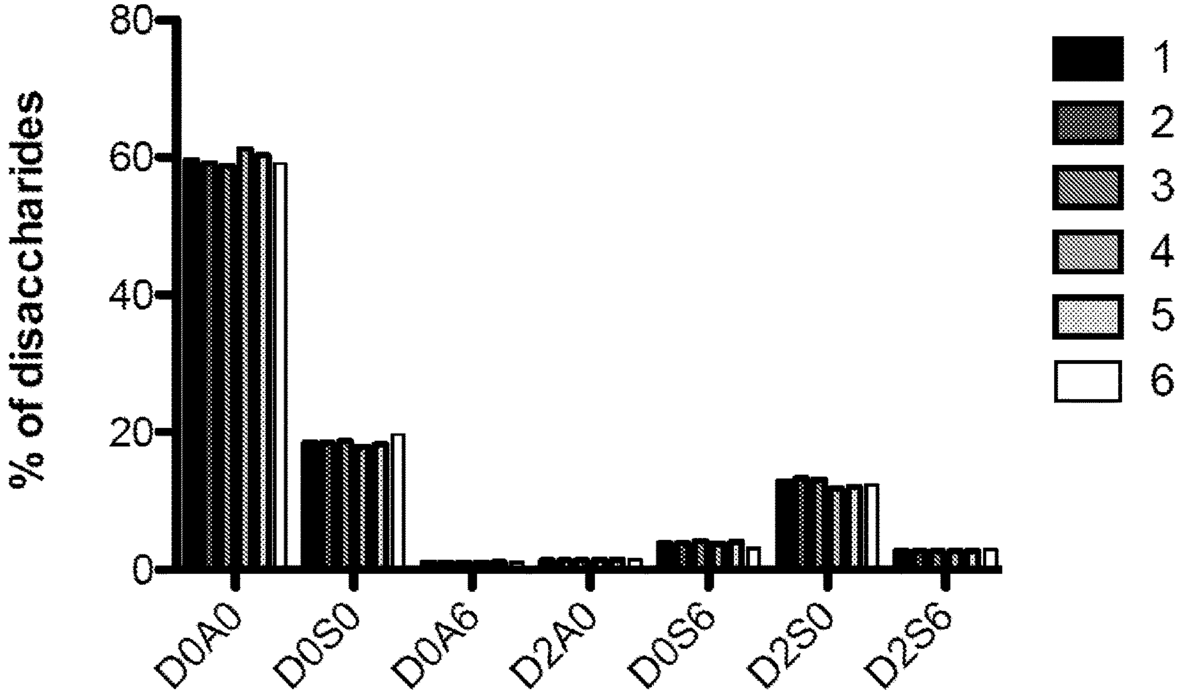
FIG. 6 shows reproducibility of disaccharide composition in CHO cell produced heparan sulfate.

Heparan sulfate was separately purified from ChA27 grown in six flasks. The disaccharide composition of the heparan sulfate was determined by digesting the heparan sulfate with heparin lyases, tagging the disaccharides with aniline and analyzing the composition by LCMS. Multiple preparations showed consistency in composition (FIG. 6).

Example 11: Size of Heparan Sulfate Chains

Figure 7:
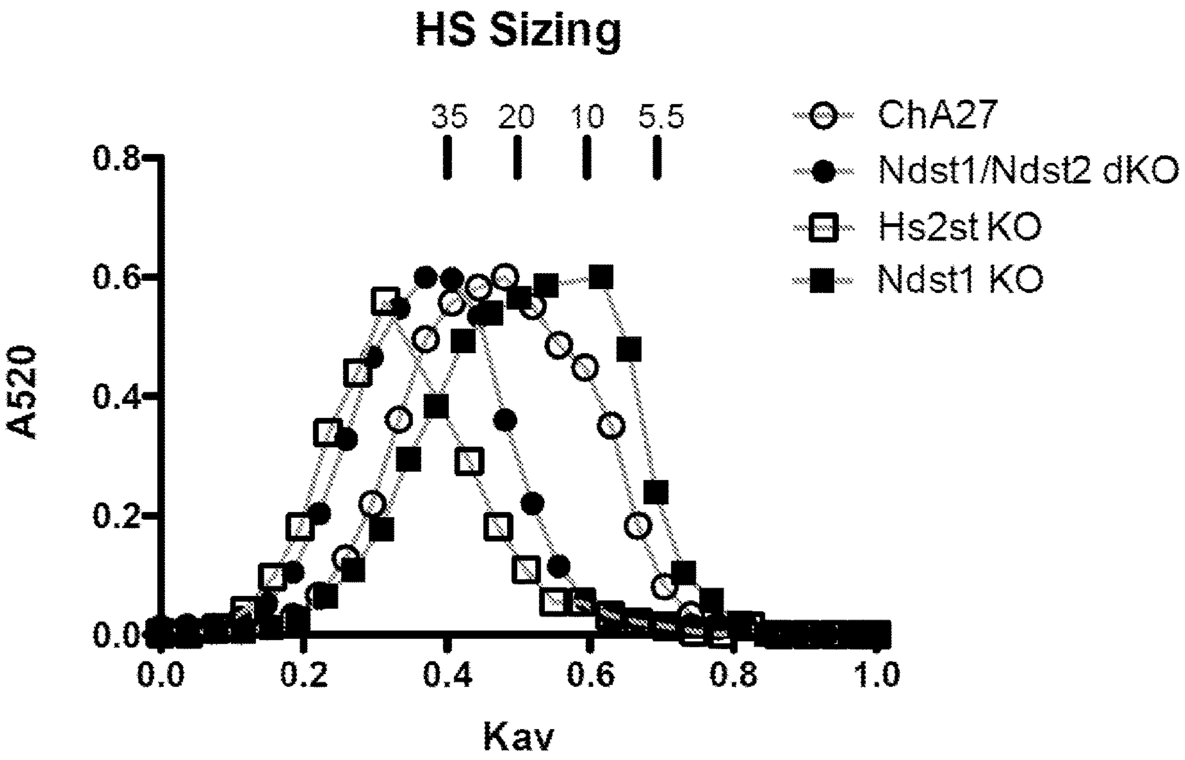
FIG. 7 shows the effect of genetic background of CHO cells on length of heparan sulfate chain.

Purified heparan sulfate chains from engineered cell lines were loaded onto a Sepharose® CL-6B column and eluted over 24 hours. The fractions were collected and heparan sulfate content in each fraction was determined by carbazole assay. The size of heparan sulfate chains was calculated using a published calibration curve in comparison to dextran blue and phenol red standards. Knock out of Hs2st, Glce and Ndst1/Ndst2 resulted in longer chain lengths while knock out of Ndst1 or Ndst2 independently had little to no effect (FIG. 7).

TABLE 3

Cell lines producing modified heparan sulfate

| Cell Line ID | Gene KO | Gene KI | Enzymes |
|---|---|---|---|
| CHA27 | Chsy1 | | CS deficient |
| CHA27 − 2S | Chsy1 | | CS deficient |
| | Hs2st | | HS 2O-sulfation deficient |
| CHA27 − GLCE | ChSy1 | | CS deficient |
| | Glce | | HS epimerization deficient |
| CHA27 − NS1 | Chsy1 | | CS deficient |
| | Hsndst1 | | HS NDST1-sulfation deficient |
| CHA27 − NS2 | Chsy1 | | CS deficient |
| | Hsndst2 | | HS NDST2-sulfation deficient |
| CHA27 − NS1/2 | Chsy1 | | CS deficient |
| | HsndstT1 | | HS NDST1-sulfation deficient |
| | Hsndst2 | | HS NDST2-sulfation deficient |
| CHA27 − NS3 | Chsy1 | | CS deficient |
| | Hsndst3 | | HS NDST3-sulfation deficient |
| CHA27 − NS4 | Chsy1 | | CS deficient |
| | Hsndst4 | | HS NDST4-sulfation deficient |
| CHA27 − Sulf1 | Chsy1 | | CS deficient |
| | Sulf1 | | Sulfatase 1 deficient |
| CHA27 − Sulf2 | Chsy1 | | CS deficient |
| | Sulf2 | | Sulfatase 2 deficient |
| CHA27 − Sulf1/2 | Chsy1 | | CS deficient |
| | Sulf1/2 | | Sulfatase 1 deficient |
| | | | Sulfatase 2 deficient |
| CHA27 − N1/2 + NS3 | | | CS deficient |
| | Chsy1 | | HS NDST1-sulfation deficient |
| | Hsndst1 | Hsndst3 | HS NDST2-sulfation deficient |
| | Hsndst2 | | HS NDST3-sulfation Added |
| CHA27 − NS1/2 + N4 | | | CS deficient |
| | Chsy1 | | HS NDST1-sulfation deficient |
| | Hsndst1 | Hsndst4 | HS NDST2-sulfation deficient |
| | Hsndst2 | | HS NDST4-sulfation Added |
| CHA27 + 6S1 | | | CS deficient |
| | Chsy1 | Hs6stβ1 | HS 6OST1-sulfation Added |
| CHA27 + 6S2 | | | CS deficient |
| | Chsy1 | Hs6st2 | HS 6OST2-sulfation Added |
| CHA27 + 6S3 | | | CS deficient |
| | Chsy1 | Hs6st3 | HS 6OST3-sulfation Added |
| CHA27 + 6S1/2 | | | CS deficient |
| | Chsy1 | Hs6st1 | HS 6OST1-sulfation Added |
| | | Hs6st2 | HS 6OST2-sulfation Added |
| CHA27 + 3S1 | | | CS deficient |
| | Chsy1 | Hs3st1 | HS 3OST1-sulfation Added |
| CHA27 + 3S2 | | | CS deficient |
| | Chsy1 | Hs3st2 | HS 3OST-2sulfation Added |

TABLE 3-continued

Cell lines producing modified heparan sulfate

| Cell Line ID | Gene KO | Gene KI | Enzymes |
|---|---|---|---|
| CHA27 + 3S3a | Chsy1 | Hs3st3a | CS deficient<br>HS 3OST3a-sulfation Added |
| CHA27 + 3S3b | Chsy1 | Hs3st3b | CS deficient<br>HS 3OST3b-sulfation Added |
| CHA27 + 3S4 | Chsy1 | Hs3st4 | CS deficient<br>HS 3OST4-sulfation Added |
| CHA27 + 3S5 | Chsy1 | Hs3st5 | CS deficient<br>HS 3OST5-sulfation Added |
| CHA27 + 3S6 | Chsy1 | Hs3st6 | CS deficient<br>HS 3OST6-sulfation Added |
| CHA27 + 6S1/2 + 3S1 | Chsy1 | Hs6st1<br>Hs6st2<br>Hs3st1 | CS deficient<br>HS 6OST1-sulfation Added<br>HS 6OST2-sulfation Added<br>HS 3OST1-sulfation Added |
| CHA27 + 6S1/2 + 3S2 | Chsy1 | Hs6st1<br>Hs6st2<br>Hs3st2 | CS deficient<br>HS 6OST1-sulfation Added<br>HS 6OST2-sulfation Added<br>HS 3OST2-sulfation Added |
| CHA27 + 6S1/2 + 3S3a or 3b | Chsy1 | Hs6st1<br>Hs6st2<br>Hs3st3a or 3b | CS deficient<br>HS 6OST1-sulfation Added<br>HS 6OST2-sulfation Added<br>HS 3OST3-sulfation Added |
| CHA27 + 6S1/2 + 3S4 | Chsy1 | Hs6st1<br>Hs6st2<br>Hs3st4 | CS deficient<br>HS 6OST1-sulfation Added<br>HS 6OST2-sulfation Added<br>HS 3OST4-sulfation Added |
| CHA27 + 6S1/2 + 3S5 | Chsy1 | Hs6st1<br>Hs6st2<br>Hs3st5 | CS deficient<br>HS 6OST1-sulfation Added<br>HS 6OST2-sulfation Added<br>HS 3OST5-sulfation Added |
| CHA27 + 6S1/2 + 3S6 | Chsy1 | Hs6st1<br>Hs6st2<br>Hs3st6 | CS deficient<br>HS 6OST1-sulfation Added<br>HS 6OST2-sulfation Added<br>HS 3OST6-sulfation Added |
| CHA27 − N1/2 + NS3 + 6S1 | Chsy1<br>Hsndst1<br>Hsndst2 | Hsndst3<br>Hs6st1 | CS deficient<br>HS NDST1-sulfation deficient<br>HS NDST2-sulfation deficient<br>HS NDST3-sulfation Added<br>HS 6OST1-sulfation Added |
| CHA27 − N1/2 + NS3 + 6S2 | Chsy1<br>Hsndst1<br>Hsndst2 | Hsndst3<br>Hs6st2 | CS deficient<br>HS NDST1-sulfation deficient<br>HS NDST2-sulfation deficient<br>HS NDST3-sulfation Added<br>HS 6OST2-sulfation Added |
| CHA27 − N1/2 + NS3 + 6S3 | Chsy1<br>Hsndst1<br>Hsndst2 | Hsndst3<br>Hs6st3 | CS deficient<br>HS NDST1-sulfation deficient<br>HS NDST2-sulfation deficient<br>HS NDST3-sulfation Added<br>HS 6OST3-sulfation Added |
| CHA27 − N1/2 + NS4 + 6S1 | Chsy1<br>Hsndst1<br>Hsndst2 | Hsndst4<br>Hs6st1 | CS deficient<br>HS NDST1-sulfation deficient<br>HS NDST2-sulfation deficient<br>HS NDST4-sulfation Added<br>HS 6OST1-sulfation Added |
| CHA27 − N1/2 + NS4 + 6S2 | Chsy1<br>Hsndst1<br>Hsndst2 | Hsndst4<br>Hs6st2 | CS deficient<br>HS NDST1-sulfation deficient<br>HS NDST2-sulfation deficient<br>HS NDST4-sulfation Added<br>HS 6OST2-sulfation Added |
| CHA27 − N1/2 + NS4 + 6S3 | Chsy1<br>Hsndst1<br>Hsndst2 | Hsndst4<br>Hs6st3 | CS deficient<br>HS NDST1-sulfation deficient<br>HS NDST2-sulfation deficient<br>HS NDST4-sulfation Added<br>HS 6OST3-sulfation Added |
| CHA27 − N1/2 + NS3 + 3S1 | Chsy1<br>Hsndst1<br>Hsndst2 | Hsndst3<br>Hs3st1 | CS deficient<br>HS NDST1-sulfation deficient<br>HS NDST2-sulfation deficient<br>HS NDST3-sulfation Added<br>HS 3OST1-sulfation Added |
| CHA27 − N1/2 + NS3 + 3S2 | Chsy1<br>Hsndst1<br>Hsndst2 | Hsndst3<br>Hs3st2 | CS deficient<br>HS NDST1-sulfation deficient<br>HS NDST2-sulfation deficient<br>HS NDST3-sulfation Added<br>HS 3OST2-sulfation Added |

TABLE 3-continued

| Cell lines producing modified heparan sulfate | | | |
|---|---|---|---|
| Cell Line ID | Gene KO | Gene KI | Enzymes |
| CHA27 − N1/2 + NS3 + 3S3a | | | CS deficient |
| or b | Chsy1 | | HS NDST1-sulfation deficient |
| | Hsndst1 | Hsndst3 | HS NDST2-sulfation deficient |
| | Hsndst2 | 3a or 3b | HS NDST3-sulfation Added |
| | | | HS 3OST3-sulfation Added |
| CHA27 − N1/2 + NS3 + 3S4 | | | CS deficient |
| | Chsy1 | | HS NDST1-sulfation deficient |
| | Hsndst1 | Hsndst3 | HS NDST2-sulfation deficient |
| | Hsndst2 | Hs3st4 | HS NDST3-sulfation Added |
| | | | HS 3OST4-sulfation Added |
| CHA27 − N1/2 + NS3 + 3S5 | | | CS deficient |
| | Chsy1 | | HS NDST1-sulfation deficient |
| | Hsndst1 | Hsndst3 | HS NDST2-sulfation deficient |
| | Hsndst2 | Hs3st5 | HS NDST3-sulfation Added |
| | | | HS 3OST5-sulfation Added |
| CHA27 − N1/2 + NS3 + 3S6 | | | CS deficient |
| | Chsy1 | | HS NDST1-sulfation deficient |
| | Hsndst1 | Hsndst3 | HS NDST2-sulfation deficient |
| | Hsndst2 | Hs3st6 | HS NDST3-sulfation Added |
| | | | HS 3OST6-sulfation Added |
| CHA27 − N1/2 + NS4 + 3S1 | | | CS deficient |
| | Chsy1 | | HS NDST1-sulfation deficient |
| | Hsndst1 | Hsndst4 | HS NDST2-sulfation deficient |
| | Hsndst2 | Hs3st1 | HS NDST4-sulfation Added |
| | | | HS 3OST1-sulfation Added |
| CHA27 − N1/2 + NS4 + 3S2 | | | CS deficient |
| | Chsy1 | | HS NDST1-sulfation deficient |
| | Hsndst1 | Hsndst4 | HS NDST2-sulfation deficient |
| | Hsndst2 | Hs3st2 | HS NDST4-sulfation Added |
| | | | HS 3OST2-sulfation Added |
| CHA27 − N1/2 + NS4 + 3S3a | | | CS deficient |
| or 3b | Chsy1 | | HS NDST1-sulfation deficient |
| | Hsndst1 | Hsndst4 | HS NDST2-sulfation deficient |
| | Hsndst2 | Hs3st3a or 3b | HS NDST4-sulfation Added |
| | | | HS 3OST3-sulfation Added |
| CHA27 − N1/2 + NS4 + 3S4 | | | CS deficient |
| | Chsy1 | | HS NDST1-sulfation deficient |
| | Hsndst1 | Hsndst4 | HS NDST2-sulfation deficient |
| | Hsndst2 | Hs3st4 | HS NDST4-sulfation Added |
| | | | HS 3OST4-sulfation Added |
| CHA27 − N1/2 + NS4 + 3S5 | | | CS deficient |
| | Chsy1 | | HS NDST1-sulfation deficient |
| | Hsndst1 | Hsndst4 | HS NDST2-sulfation deficient |
| | Hsndst2 | Hs3st5 | HS NDST4-sulfation Added |
| | | | HS 3OST5-sulfation Added |
| CHA27 − N1/2 + NS4 + 3S6 | | | CS deficient |
| | Chsy1 | | HS NDST1-sulfation deficient |
| | Hsndst1 | Hsndst4 | HS NDST2-sulfation deficient |
| | Hsndst2 | Hs3st6 | HS NDST4-sulfation Added |
| | | | HS 3OST6-sulfation Added |
| CHA27 − | | | CS deficient |
| N1/2 + NS3 + 6ST1/2 + 3S1 | | | HS NDST1-sulfation deficient |
| | Chsy1 | Hsndst3 | HS NDST2-sulfation deficient |
| | Hsndst1 | Hs6st1/2 | HS NDST3-sulfation Added |
| | Hsndst2 | Hs3st1 | HS 6OST1/2-sulfation Added |
| | | | HS 3OST1-sulfation Added |
| CHA27 − | | | CS deficient |
| N1/2 + NS3 + 6ST1/2 + 3S2 | | | HS NDST1-sulfation deficient |
| | Chsy1 | Hsndst3 | HS NDST2-sulfation deficient |
| | Hsndst1 | Hs6st1/2 | HS NDST3-sulfation Added |
| | Hsndst2 | Hs3st2 | HS 6OST1/2-sulfation Added |
| | | | HS 3OST2-sulfation Added |
| CHA27 − | | | CS deficient |
| N1/2 + NS3 + 6ST1/2 + 3S3a | | | HS NDST1-sulfation deficient |
| or 3b | Chsy1 | Hsndst3 | HS NDST2-sulfation deficient |
| | Hsndst1 | Hs6st1/2 | HS NDST3-sulfation Added |
| | Hsndst2 | Hs3st3a or 3b | HS 6OST1/2-sulfation Added |
| | | | HS 3OST3-sulfation Added |
| CHA27 − | | | CS deficient |
| N1/2 + NS3 + 6ST1/2 + 3S4 | | | HS NDST1-sulfation deficient |
| | Chsy1 | Hsndst3 | HS NDST2-sulfation deficient |
| | Hsndst1 | Hs6st1/2 | HS NDST3-sulfation Added |
| | Hsndst2 | Hs3stT4 | HS 6OST1/2-sulfation Added |
| | | | HS 3OST4-sulfation Added |

TABLE 3-continued

| Cell lines producing modified heparan sulfate | | | |
|---|---|---|---|
| Cell Line ID | Gene KO | Gene KI | Enzymes |
| CHA27 –<br>N1/2 + NS3 + 6ST1/2 + 3S5 | Chsy1<br>Hsndst1<br>Hsndst2 | Hsndst3<br>Hs6st1/2<br>Hs3st5 | CS deficient<br>HS NDST1-sulfation deficient<br>HS NDST2-sulfation deficient<br>HS NDST3-sulfation Added<br>HS 6OST1/2-sulfation Added<br>HS 3OST5-sulfation Added |
| CHA27 –<br>N1/2 + NS3 + 6ST1/2 + 3S6 | Chsy1<br>Hsndst1<br>Hsndst2 | Hsndst3<br>Hs6st1/2<br>Hs3st6 | CS deficient<br>HS NDST1-sulfation deficient<br>HS NDST2-sulfation deficient<br>HS NDST3-sulfation Added<br>HS 6OST1/2-sulfation Added<br>HS 3OST6-sulfation Added |
| CHA27 –<br>N1/2 + NS4 + 6ST1/2 + 3S1 | Chsy1<br>Hsndst1<br>Hsndst2 | Hsndst4<br>Hs6stT1/2<br>Hs3st1 | CS deficient<br>HS NDST1-sulfation deficient<br>HS NDST2-sulfation deficient<br>HS NDST4-sulfation Added<br>HS 6OST1/2-sulfation Added<br>HS 3OST1-sulfation Added |
| CHA27 –<br>N1/2 + NS4 + 6ST1/2 + 3S2 | Chsy1<br>Hsndst1<br>Hsndst2 | Hsndst3<br>Hs6st1/2<br>Hs3st2 | CS deficient<br>HS NDST1-sulfation deficient<br>HS NDST2-sulfation deficient<br>HS NDST4-sulfation Added<br>HS 6OST1/2-sulfation Added<br>HS 3OST2-sulfation Added |
| CHA27 –<br>N1/2 + NS4 + 6ST1/2 + 3S3a<br>or 3b | Chsy1<br>Hsndst1<br>Hsndst2 | Hsndst3<br>Hs6st1/2<br>Hs3st3a or 3b | CS deficient<br>HS NDST1-sulfation deficient<br>HS NDST2-sulfation deficient<br>HS NDST4-sulfation Added<br>HS 6OST1/2-sulfation Added<br>HS 3OST3-sulfation Added |
| CHA27 –<br>N1/2 + NS4 + 6ST1/2 + 3S4 | Chsy1<br>Hsndst1<br>Hsndst2 | Hsndst3<br>Hs6st1/2<br>HSs3st4 | CS deficient<br>HS NDST1-sulfation deficient<br>HS NDST2-sulfation deficient<br>HS NDST4-sulfation Added<br>HS 6OST1/2-sulfation Added<br>HS 3OST4-sulfation Added |
| CHA27 –<br>N1/2 + NS4 + 6ST1/2 + 3S5 | Chsy1<br>Hsndst1<br>Hsndst2 | Hsndst3<br>Hs6st1/2<br>Hs3st5 | CS deficient<br>HS NDST1-sulfation deficient<br>HS NDST2-sulfation deficient<br>HS NDST4-sulfation Added<br>HS 6OST1/2-sulfation Added<br>HS 3OST5-sulfation Added |
| CHA27 –<br>N1/2 + NS4 + 6ST1/2 + 3S6 | Chsy1<br>Hsndst1<br>Hsndst2 | Hsndst3<br>Hs6st1/2<br>Hs3st6 | CS deficient<br>HS NDST1-sulfation deficient<br>HS NDST2-sulfation deficient<br>HS NDST4-sulfation Added<br>HS 6OST1/2-sulfation Added<br>HS 3OST6-sulfation Added |

TABLE 4

| Cell lines producing modified heparin | | | |
|---|---|---|---|
| Cell Line ID | Gene KO | Gene KI | Enzymes |
| CHA27 + NS1 | Chsy1 | Hsndst 1 | CS deficient<br>HS NDST 1 over-sulfation |
| CHA27 + NS2 | Chsy1 | Hsndst 2 | CS deficient<br>HS NDST 2 over-sulfation |
| CHA27 + NS1 + NS2 | Chsy1 | Hsndst 1 & 2 | CS deficient<br>HS NDST 1 & 2 over-sulfation |
| CHA27 + NS1 + 2S | Chsy1 | Hsndst 1<br>Hs2st | CS deficient<br>HS NDST over-sulfation<br>HS 2OST over-sulfation |
| CHA27 + NS2 + 2S | Chsy1 | Hsndst 2<br>Hs2st | CS deficient<br>Hsndst2 over-sulfation<br>HS 2OST over-sulfation |
| CHA27 + NS1 + NS2 + 2S | Chsy1 | Hsndst 1 & 2<br>Hs2st | CS deficient<br>Hsndst 1 & 2 over-sulfation<br>HS 2OST over-sulfation |
| CHA27 + NS1 + Ep | Chsy1 | Hsndst 1<br>epimerase | CS deficient<br>HS NDST 1 over-sulfation<br>Epimerase over-epimerization |

TABLE 4-continued

| Cell lines producing modified heparin | | | |
|---|---|---|---|
| Cell Line ID | Gene KO | Gene KI | Enzymes |
| CHA27 + NS2 + Ep | Chsy1 | Hsndst 2<br>epimerase | CS deficient<br>HS NDST 2 over-sulfation<br>Epimerase over-epimerization |
| CHA27 + NS1 + NS2 + Ep | Chsy1 | Hsndst 1 & 2<br>epimerase | CS deficient<br>HS NDST 1 & 2 over-sulfation<br>Epimerase over-epimerization |
| CHA27 + NS1 + 2S + Ep | Chsy1 | Hsndst 1<br>Hs2st<br>epimerase | CS deficient<br>HS NDST over-sulfation<br>HS 2OST over-sulfation<br>Epimerase over-epimerization |
| CHA27 + NS2 + 2S + Ep | Chsy1 | Hsndst 2<br>Hs2st<br>epimerase | CS deficient<br>Hsndst2 over-sulfation<br>HS 2OST over-sulfation<br>Epimerase over-epimerization |
| CHA27 + NS1 + NS2 + 2S + Ep | Chsy1 | Hsndst 1 & 2<br>Hs2st<br>epimerase | CS deficient<br>Hsndst 1 & 2 over-sulfation<br>HS 2OST over-sulfation<br>Epimerase over-epimerization |
| CHA27 + NS1 + 6S | Chsy1 | Hsndst 1<br>HS6st 1, 2 or 1 & 2 | CS deficient<br>HS NDST 1 over-sulfation<br>HS 6OST over-sulfation |
| CHA27 + NS2 + 6S | Chsy1 | Hsndst 2<br>HS6st 1, 2 or 1 & 2 | CS deficient<br>HS NDST 2 over-sulfation |
| CHA27 + NS1 + NS2 + 6S | Chsy1 | Hsndst 1 & 2<br>HS6st 1, 2 or 1 & 2 | CS deficient<br>HS NDST 1 & 2 over-sulfation |
| CHA27 + NS1 + 2S + 6S | Chsy1 | Hsndst 1<br>HS2st<br>HS6st 1, 2 or 1 & 2 | CS deficient<br>HS NDST over-sulfation<br>HS 2OST over-sulfation<br>HS 6OST over-sulfation |
| CHA27 + NS2 + 2S + 6S | Chsy1 | Hsndst 2<br>Hs2st<br>HS6st 1, 2 or 1 & 2 | CS deficient<br>Hsndst2 over-sulfation<br>HS 2OST over-sulfation |
| CHA27 + NS1 + NS2 + 2S + 6S | Chsy1 | Hsndst 1 & 2<br>Hs2st<br>HS6st 1, 2 or 1 & 2 | CS deficient<br>Hsndst 1 & 2 over-sulfation<br>HS 2OST over-sulfation |
| CHA27 + NS1 + Ep | Chsy1 | Hsndst 1<br>Epimerase<br>HS6st 1, 2 or 1 & 2 | CS deficient<br>HS NDST 1 over-sulfation<br>Epimerase over-epimerization |
| CHA27 + NS2 + Ep + 6S | Chsy1 | Hsndst 2<br>Epimerase<br>HS6st 1, 2 or 1 & 2 | CS deficient<br>HS NDST 2 over-sulfation<br>Epimerase over-epimerization |
| CHA27 + NS1 + NS2 + Ep + 6S | Chsy1 | Hsndst 1 & 2<br>Epimerase<br>HS6st 1, 2 or 1 & 2 | CS deficient<br>HS NDST 1 & 2 over-sulfation<br>Epimerase over-epimerization |
| CHA27 + NS1 + 2S + Ep + 6S | Chsy1 | Hsndst 1<br>Hs2st<br>Epimerase<br>HS6st 1, 2 or 1 & 2 | CS deficient<br>HS NDST over-sulfation<br>HS 2OST over-sulfation<br>Epimerase over-epimerization |
| CHA27 + NS2 + 2S + Ep + 6S | Chsy1 | Hsndst 2<br>Hs2st<br>Epimerase<br>HS6st 1, 2 or 1 & 2 | CS deficient<br>Hsndst2 over-sulfation<br>HS 2OST over-sulfation<br>Epimerase over-epimerization |
| CHA27 + NS1 + NS2 + 2S + Ep + 6S | Chsy1 | Hsndst 1 & 2<br>Hs2st<br>Epimerase<br>HS6st 1, 2 or 1 & 2 | CS deficient<br>Hsndst 1 & 2 over-sulfation<br>HS 2OST over-sulfation<br>Epimerase over-epimerization<br>HS 6OST over-sulfation |
| CHA27 + NS1 + 3S | Chsy1 | Hsndst 1<br>Hs3st | CS deficient<br>HS NDST 1 over-sulfation<br>HS 3OST over-sulfation |
| CHA27 + NS2 + 3S | Chsy1 | Hsndst 2<br>Hs3st | CS deficient<br>HS NDST 2 over-sulfation<br>HS 3OST over-sulfation |
| CHA27 + NS1 + NS2 + 3S | Chsy1 | Hsndst 1 & 2<br>Hs3st | CS deficient<br>HS NDST 1 & 2 over-sulfation<br>HS 3OST over-sulfation |

TABLE 4-continued

Cell lines producing modified heparin

| Cell Line ID | Gene KO | Gene KI | Enzymes |
|---|---|---|---|
| CHA27 + NS1 + 2S + 3S | Chsy1 | Hsndst 1<br>Hs2st<br>Hs3st | CS deficient<br>HS NDST over-sulfation<br>HS 2OST over-sulfation<br>HS 3OST over-sulfation |
| CHA27 + NS2 + 2S + 3S | Chsy1 | Hsndst 2<br>Hs2st<br>Hs3st | CS deficient<br>Hsndst2 over-sulfation<br>HS 2OST over-sulfation<br>HS 3OST over-sulfation |
| CHA27 + NS1 + NS2 + 2S + 3S | Chsy1 | Hsndst 1 & 2<br>Hs2st<br>Hs3st | CS deficient<br>Hsndst 1 & 2 over-sulfation<br>HS 2OST over-sulfation<br>HS 3OST over-sulfation |
| CHA27 + NS1 + Ep + 3S | Chsy1 | Hsndst 1<br>Epimerase<br>Hs3st | CS deficient<br>HS NDST 1 over-sulfation<br>Epimerase over-epimerization<br>HS 3OST over-sulfation |
| CHA27 + NS2 + Ep + 3S | Chsy1 | Hsndst 2<br>Epimerase<br>Hs3st | CS deficient<br>HS NDST 2 over-sulfation<br>Epimerase over-epimerization<br>HS 3OST over-sulfation |
| CHA27 + NS1 + NS2 + Ep + 3S | Chsy1 | Hsndst 1 & 2<br>Epimerase<br>Hs3st | CS deficient<br>HS NDST 1 & 2 over-sulfation<br>Epimerase over-epimerization<br>HS 3OST over-sulfation |
| CHA27 + NS1 + 2S + Ep + 3S | Chsy1 | Hsndst 1<br>Hs2st<br>Epimerase<br>Hs3st | CS deficient<br>HS NDST over-sulfation<br>HS 2OST over-sulfation<br>Epimerase over-epimerization<br>HS 3OST over-sulfation |
| CHA27 + NS2 + 2S + Ep + 3S | Chsy1 | Hsndst 2<br>Hs2st<br>Epimerase<br>Hs3st | CS deficient<br>Hsndst2 over-sulfation<br>HS 2OST over-sulfation<br>Epimerase over-epimerization<br>HS 3OST over-sulfation |
| CHA27 + NS1 + NS2 + 2S + Ep + 3S | Chsy1 | Hsndst 1 & 2<br>Hs2st<br>Epimerase<br>Hs3st | CS deficient<br>Hsndst 1 & 2 over-sulfation<br>HS 2OST over-sulfation<br>Epimerase over-epimerization<br>HS 3OST over-sulfation |
| CHA27 + NS1 + 6S + 3S | Chsy1 | Hsndst 1<br>HS6st 1, 2 or 1 & 2<br>Hs3st | CS deficient<br>HS NDST 1 over-sulfation<br>HS 6OST over-sulfation<br>HS 3OST over-sulfation |
| CHA27 + NS2 + 6S + 3S | Chsy1 | Hsndst 2<br>HS6st 1, 2 or 1 & 2<br>Hs3st | CS deficient<br>HS NDST 2 over-sulfation<br>HS 3OST over-sulfation<br>HS 3OST over-sulfation |
| CHA27 + NS1 + NS2 + 6S + 3S | Chsy1 | Hsndst 1 & 2<br>HS6st 1, 2 or 1 & 2<br>Hs3st | CS deficient<br>HS NDST 1 & 2 over-sulfation<br>HS 3OST over-sulfation |
| CHA27 + NS1 + 2S + 6S + 3S | Chsy1 | Hsndst 1<br>HS2st<br>HS6st 1, 2 or 1 & 2<br>Hs3st | CS deficient<br>HS NDST over-sulfation<br>HS 2OST over-sulfation<br>HS 6OST over-sulfation<br>HS 3OST over-sulfation |
| CHA27 + NS2 + 2S + 6S + 3S | Chsy1 | Hsndst 2<br>Hs2st<br>HS6st 1, 2 or 1 & 2<br>Hs3st | CS deficient<br>Hsndst2 over-sulfation<br>HS 2OST over-sulfation<br>HS 3OST over-sulfation |
| CHA27 + NS1 + NS2 + 2S + 6S + 3S | Chsy1 | Hsndst 1 & 2<br>Hs2st<br>HS6st 1, 2 or 1 & 2<br>Hs3st | CS deficient<br>Hsndst 1 & 2 over-sulfation<br>HS 2OST over-sulfation<br>HS 3OST over-sulfation |
| CHA27 + NS1 + Ep + 3S | Chsy1 | Hsndst 1<br>Epimerase<br>HS6st 1, 2 or 1 & 2<br>Hs3st | CS deficient<br>HS NDST 1 over-sulfation<br>Epimerase over-epimerization<br>HS 3OST over-sulfation |
| CHA27 + NS2 + Ep + 6S + 3S | Chsy1 | Hsndst 2<br>Epimerase<br>HS6st 1, 2 or 1 & 2<br>Hs3st | CS deficient<br>HS NDST 2 over-sulfation<br>Epimerase over-epimerization<br>HS 3OST over-sulfation |

TABLE 4-continued

| Cell lines producing modified heparin | | | |
|---|---|---|---|
| Cell Line ID | Gene KO | Gene KI | Enzymes |
| CHA27 + NS1 + NS2 + Ep + 6S + 3S | Chsy1 | Hsndst 1 & 2<br>Epimerase<br>HS6st 1, 2 or 1 & 2<br>Hs3st | CS deficient<br>HS NDST 1 & 2 over-sulfation<br>Epimerase over-epimerization<br>HS 3OST over-sulfation |
| CHA27 + NS1 + 2S + Ep + 6S + 3S | Chsy1 | Hsndst 1<br>Hs2st<br>Epimerase<br>HS6st 1, 2 or 1 & 2<br>Hs3st | CS deficient<br>HS NDST over-sulfation<br>HS 2OST over-sulfation<br>Epimerase over-epimerization<br>HS 3OST over-sulfation |
| CHA27 + NS2 + 2S + Ep + 6S + 3S | Chsy1 | Hsndst 2<br>Hs2st<br>Epimerase<br>HS6st 1, 2 or 1 & 2<br>Hs3st | CS deficient<br>Hsndst2 over-sulfation<br>HS 2OST over-sulfation<br>Epimerase over-epimerization<br>HS 3OST over-sulfation |
| CHA27 + NS1 + NS2 + 2S + Ep + 6S + 3S | Chsy1 | Hsndst 1 & 2<br>Hs2st<br>Epimerase<br>HS6st 1, 2 or 1 & 2<br>Hs3st | CS deficient<br>Hsndst 1 & 2 over-sulfation<br>HS 2OST over-sulfation<br>Epimerase over-epimerization<br>HS 6OST over-sulfation<br>HS 3OST over-sulfation |
| CHA27 + NS1 + serglycin | Chsy1 | Hsndst 1<br>serglycin | CS deficient<br>HS NDST 1 over-sulfation |
| CHA27 + NS2 + serglycin | Chsy1 | Hsndst 2<br>serglycin | CS deficient<br>HS NDST 2 over-sulfation |
| CHA27 + NS1 + NS2 + serglycin | Chsy1 | Hsndst 1 & 2<br>serglycin | CS deficient<br>HS NDST 1 & 2 over-sulfation |
| CHA27 + NS1 + 2S + serglycin | Chsy1 | Hsndst 1<br>Hs2st<br>serglycin | CS deficient<br>HS NDST over-sulfation<br>HS 2OST over-sulfation |
| CHA27 + NS2 + 2S + serglycin | Chsy1 | Hsndst 2<br>Hs2st<br>serglycin | CS deficient<br>Hsndst2 over-sulfation<br>HS 2OST over-sulfation |
| CHA27 + NS1 + NS2 + 2S + serglycin | Chsy1 | Hsndst 1 & 2<br>Hs2st<br>serglycin | CS deficient<br>Hsndst 1 & 2 over-sulfation<br>HS 2OST over-sulfation |
| CHA27 + NS1 + Ep + serglycin | Chsy1 | Hsndst 1<br>Epimerase<br>serglycin | CS deficient<br>HS NDST 1 over-sulfation<br>Epimerase over-epimerization |
| CHA27 + NS2 + Ep + serglycin | Chsy1 | Hsndst 2<br>Epimerase<br>serglycin | CS deficient<br>HS NDST 2 over-sulfation<br>Epimerase over-epimerization |
| CHA27 + NS1 + NS2 + Ep + serglycin | Chsy1 | Hsndst 1 & 2<br>Epimerase<br>serglycin | CS deficient<br>HS NDST 1 & 2 over-sulfation<br>Epimerase over-epimerization |
| CHA27 + NS1 + 2S + Ep + serglycin | Chsy1 | Hsndst 1<br>Hs2st<br>Epimerase<br>serglycin | CS deficient<br>HS NDST over-sulfation<br>HS 2OST over-sulfation<br>Epimerase over-epimerization |
| CHA27 + NS2 + 2S + Ep + serglycin | Chsy1 | Hsndst 2<br>Hs2st<br>Epimerase<br>serglycin | CS deficient<br>Hsndst2 over-sulfation<br>HS 2OST over-sulfation<br>Epimerase over-epimerization |
| CHA27 + NS1 + NS2 + 2S + Ep + serglycin | Chsy1 | Hsndst 1 & 2<br>Hs2st<br>Epimerase<br>serglycin | CS deficient<br>Hsndst 1 & 2 over-sulfation<br>HS 2OST over-sulfation<br>Epimerase over-epimerization |
| CHA27 + NS1 + 6S + serglycin | Chsy1 | Hsndst 1<br>HS6st 1, 2 or 1 & 2<br>serglycin | CS deficient<br>HS NDST 1 over-sulfation<br>HS 6OST over-sulfation |
| CHA27 + NS2 + 6S + serglycin | Chsy1 | Hsndst 2<br>HS6st 1, 2 or 1 & 2<br>serglycin | CS deficient<br>HS NDST 2 over-sulfation |
| CHA27 + NS1 + NS2 + 6S + serglycin | Chsy1 | Hsndst 1 & 2<br>HS6st 1, 2 or 1 & 2<br>serglycin | CS deficient<br>HS NDST 1 & 2 over-sulfation |
| CHA27 + NS1 + 2S + 6S + serglycin | Chsy1 | Hsndst 1<br>HS2st<br>HS6st 1, 2 or 1 & 2<br>serglycin | CS deficient<br>HS NDST over-sulfation<br>HS 2OST over-sulfation<br>HS 6OST over-sulfation |

TABLE 4-continued

Cell lines producing modified heparin

| Cell Line ID | Gene KO | Gene KI | Enzymes |
| --- | --- | --- | --- |
| CHA27 + NS2 + 2S + 6S + serglycin | Chsy1 | Hsndst 2<br>Hs2st<br>HS6st 1, 2 or 1 & 2<br>serglycin | CS deficient<br>Hsndst2 over-sulfation<br>HS 2OST over-sulfation |
| CHA27 + NS1 + NS2 + 2S + 6S + serglycin | Chsy1 | Hsndst 1 & 2<br>Hs2st<br>HS6st 1, 2 or 1 & 2<br>serglycin | CS deficient<br>Hsndst 1 & 2 over-sulfation<br>HS 2OST over-sulfation |
| CHA27 + NS1 + Ep + serglycin | Chsy1 | Hsndst 1<br>Epimerase<br>HS6st 1, 2 or 1 & 2<br>serglycin | CS deficient<br>HS NDST 1 over-sulfation<br>Epimerase over-epimerization |
| CHA27 + NS2 + Ep + 6S + serglycin | Chsy1 | Hsndst 2<br>Epimerase<br>HS6st 1, 2 or 1 & 2<br>serglycin | CS deficient<br>HS NDST 2 over-sulfation<br>Epimerase over-epimerization |
| CHA27 + NS1 + NS2 + Ep + 6S + serglycin | Chsy1 | Hsndst 1 & 2<br>Epimerase<br>HS6st 1, 2 or 1 & 2<br>serglycin | CS deficient<br>HS NDST 1 & 2 over-sulfation<br>Epimerase over-epimerization |
| CHA27 + NS1 + 2S + Ep + 6S + serglycin | Chsy1 | Hsndst 1<br>Hs2st<br>Epimerase<br>HS6st 1, 2 or 1 & 2<br>serglycin | CS deficient<br>HS NDST over-sulfation<br>HS 2OST over-sulfation<br>Epimerase over-epimerization |
| CHA27 + NS2 + 2S + Ep + 6S + serglycin | Chsy1 | Hsndst 2<br>Hs2st<br>Epimerase<br>HS6st 1, 2 or 1 & 2<br>serglycin | CS deficient<br>Hsndst2 over-sulfation<br>HS 2OST over-sulfation<br>Epimerase over-epimerization |
| CHA27 + NS1 + NS2 + 2S + Ep + 6S + serglycin | Chsy1 | Hsndst 1 & 2<br>Hs2st<br>Epimerase<br>HS6st 1, 2 or 1 & 2<br>serglycin | CS deficient<br>Hsndst 1 & 2 over-sulfation<br>HS 2OST over-sulfation<br>Epimerase over-epimerization<br>HS 6OST over-sulfation |
| CHA27 + NS1 + 3S + serglycin | Chsy1 | Hsndst 1<br>Hs3st<br>serglycin | CS deficient<br>HS NDST 1 over-sulfation<br>HS 3OST over-sulfation |
| CHA27 + NS2 + 3S + serglycin | Chsy1 | Hsndst 2<br>Hs3st<br>serglycin | CS deficient<br>HS NDST 2 over-sulfation<br>HS 3OST over-sulfation |
| CHA27 + NS1 + NS2 + 3S + serglycin | Chsy1 | Hsndst 1 & 2<br>Hs3st<br>serglycin | CS deficient<br>HS NDST 1 & 2 over-sulfation<br>HS 3OST over-sulfation |
| CHA27 + NS1 + 2S + 3S + serglycin | Chsy1 | Hsndst 1<br>Hs2st<br>Hs3st<br>serglycin | CS deficient<br>HS NDST over-sulfation<br>HS 2OST over-sulfation<br>HS 3OST over-sulfation |
| CHA27 + NS2 + 2S + 3S + serglycin | Chsy1 | Hsndst 2<br>Hs2st<br>Hs3st<br>serglycin | CS deficient<br>Hsndst2 over-sulfation<br>HS 2OST over-sulfation<br>HS 3OST over-sulfation |
| CHA27 + NS1 + NS2 + 2S + 3S + serglycin | Chsy1 | Hsndst 1 & 2<br>Hs2st<br>Hs3st<br>serglycin | CS deficient<br>Hsndst 1 & 2 over-sulfation<br>HS 2OST over-sulfation<br>HS 3OST over-sulfation |
| CHA27 + NS1 + Ep + 3S + serglycin | Chsy1 | Hsndst 1<br>Epimerase<br>Hs3st<br>serglycin | CS deficient<br>HS NDST 1 over-sulfation<br>Epimerase over-epimerization<br>HS 3OST over-sulfation |
| CHA27 + NS2 + Ep + 3S + serglycin | Chsy1 | Hsndst 2<br>Epimerase<br>Hs3st<br>serglycin | CS deficient<br>HS NDST 2 over-sulfation<br>Epimerase over-epimerization<br>HS 3OST over-sulfation |
| CHA27 + NS1 + NS2 + Ep + 3S + serglycin | Chsy1 | Hsndst 1 & 2<br>Epimerase<br>Hs3st<br>serglycin | CS deficient<br>HS NDST 1 & 2 over-sulfation<br>Epimerase over-epimerization<br>HS 3OST over-sulfation |

TABLE 4-continued

| Cell lines producing modified heparin | | | |
|---|---|---|---|
| Cell Line ID | Gene KO | Gene KI | Enzymes |
| CHA27 + NS1 + 2S + Ep + 3S + serglycin | Chsy1 | Hsndst 1<br>Hs2st<br>Epimerase<br>Hs3st<br>serglycin | CS deficient<br>HS NDST over-sulfation<br>HS 2OST over-sulfation<br>Epimerase over-epimerization<br>HS 3OST over-sulfation |
| CHA27 + NS2 + 2S + Ep + 3S + serglycin | Chsy1 | Hsndst 2<br>Hs2st<br>Epimerase<br>Hs3st<br>serglycin | CS deficient<br>Hsndst2 over-sulfation<br>HS 2OST over-sulfation<br>Epimerase over-epimerization<br>HS 3OST over-sulfation |
| CHA27 + NS1 + NS2 + 2S + Ep + 3S + serglycin | Chsy1 | Hsndst 1 & 2<br>Hs2st<br>Epimerase<br>Hs3st<br>serglycin | CS deficient<br>Hsndst 1 & 2 over-sulfation<br>HS 2OST over-sulfation<br>Epimerase over-epimerization<br>HS 3OST over-sulfation |
| CHA27 + NS1 + 6S + 3S + serglycin | Chsy1 | Hsndst 1<br>HS6st 1, 2 or 1 & 2<br>Hs3st<br>serglycin | CS deficient<br>HS NDST 1 over-sulfation<br>HS 6OST over-sulfation<br>HS 3OST over-sulfation |
| CHA27 + NS2 + 6S + 3S + serglycin | Chsy1 | Hsndst 2<br>HS6st 1, 2 or 1 & 2<br>Hs3st<br>serglycin | CS deficient<br>HS NDST 2 over-sulfation<br>HS 3OST over-sulfation<br>HS 3OST over-sulfation |
| CHA27 + NS1 + NS2 + 6S + 3S + serglycin | Chsy1 | Hsndst 1 & 2<br>HS6st 1, 2 or 1 & 2<br>Hs3st<br>serglycin | CS deficient<br>HS NDST 1 & 2 over-sulfation<br>HS 3OST over-sulfation |
| CHA27 + NS1 + 2S + 6S + 3S + serglycin | Chsy1 | Hsndst 1<br>HS2st<br>HS6st 1, 2 or 1 & 2<br>Hs3st<br>serglycin | CS deficient<br>HS NDST over-sulfation<br>HS 2OST over-sulfation<br>HS 6OST over-sulfation<br>HS 3OST over-sulfation |
| CHA27 + NS2 + 2S + 6S + 3S + serglycin | Chsy1 | Hsndst 2<br>Hs2st<br>HS6st 1, 2 or 1 & 2<br>Hs3st<br>serglycin | CS deficient<br>Hsndst2 over-sulfation<br>HS 2OST over-sulfation<br>HS 3OST over-sulfation |
| CHA27 + NS1 + NS2 + 2S + 6S + 3S + serglycin | Chsy1 | Hsndst 1 & 2<br>Hs2st<br>HS6st 1, 2 or 1 & 2<br>Hs3st<br>serglycin | CS deficient<br>Hsndst 1 & 2 over-sulfation<br>HS 2OST over-sulfation<br>HS 3OST over-sulfation |
| CHA27 + NS1 + Ep + 3S + serglycin | Chsy1 | Hsndst 1<br>Epimerase<br>HS6st 1, 2 or 1 & 2<br>Hs3st<br>serglycin | CS deficient<br>HS NDST 1 over-sulfation<br>Epimerase over-epimerization<br>HS 3OST over-sulfation |
| CHA27 + NS2 + Ep + 6S + 3S + serglycin | Chsy1 | Hsndst 2<br>Epimerase<br>HS6st 1, 2 or 1 & 2<br>Hs3st<br>serglycin | CS deficient<br>HS NDST 2 over-sulfation<br>Epimerase over-epimerization<br>HS 3OST over-sulfation |
| CHA27 + NS1 + NS2 + Ep + 6S + 3S + serglycin | Chsy1 | Hsndst 1 & 2<br>Epimerase<br>HS6st 1, 2 or 1 & 2<br>Hs3st<br>serglycin | CS deficient<br>HS NDST 1 & 2 over-sulfation<br>Epimerase over-epimerization<br>HS 3OST over-sulfation |
| CHA27 + NS1 + 2S + Ep + 6S + 3S + serglycin | Chsy1 | Hsndst 1<br>Hs2st<br>Epimerase<br>HS6st 1, 2 or 1 & 2<br>Hs3st<br>serglycin | CS deficient<br>HS NDST over-sulfation<br>HS 2OST over-sulfation<br>Epimerase over-epimerization<br>HS 3OST over-sulfation |

TABLE 4-continued

Cell lines producing modified heparin

| Cell Line ID | Gene KO | Gene KI | Enzymes |
|---|---|---|---|
| CHA27 + NS2 + 2S + Ep + 6S + 3S + serglycin | Chsy1 | Hsndst 2<br>Hs2st<br>Epimerase<br>HS6st 1, 2 or 1 & 2<br>Hs3st<br>serglycin | CS deficient<br>Hsndst2 over-sulfation<br>HS 2OST over-sulfation<br>Epimerase over-epimerization<br>HS 3OST over-sulfation |
| CHA27 + NS1 + NS2 + 2S + Ep + 6S + 3S + serglycin | Chsy1 | Hsndst 1 & 2<br>Hs2st<br>Epimerase<br>HS6st 1, 2 or 1 & 2<br>Hs3st<br>serglycin | CS deficient<br>Hsndst 1 & 2 over-sulfation<br>HS 2OST over-sulfation<br>Epimerase over-epimerization<br>HS 6OST over-sulfation<br>HS 3OST over-sulfation |
| CHA27 + NS1 + serglycin + EXT2, 1, L3 | Chsy1 | Hsndst 1<br>Serglycin<br>EXT2, 1, L3 | CS deficient<br>HS NDST 1 over-sulfation<br>HS over-polymerization |
| CHA27 + NS2 + serglycin + EXT2, 1, L3 | Chsy1 | Hsndst 2<br>Serglycin<br>EXT2, 1, L3 | CS deficient<br>HS NDST 2 over-sulfation<br>HS over-polymerization |
| CHA27 + NS1 + NS2 + serglycin + EXT2, 1, L3 | Chsy1 | Hsndst 1 & 2<br>Serglycin<br>EXT2, 1, L3 | CS deficient<br>HS NDST 1 & 2 over-sulfation<br>HS over-polymerization |
| CHA27 + NS1 + 2S + serglycin + EXT2, 1, L31, L3 | Chsy1 | Hsndst 1<br>Hs2st<br>Serglycin<br>EXT2, 1, L3 | CS deficient<br>HS NDST over-sulfation<br>HS 2OST over-sulfation<br>HS over-polymerization |
| CHA27 + NS2 + 2S + serglycin + EXT2, 1, L3 | Chsy1 | Hsndst 2<br>Hs2st<br>Serglycin<br>EXT2, 1, L3 | CS deficient<br>Hsndst2 over-sulfation<br>HS 2OST over-sulfation<br>HS over-polymerization |
| CHA27 + NS1 + NS2 + 2S + serglycin + EXT2, 1, L3 | Chsy1 | Hsndst 1 & 2<br>Hs2st<br>Serglycin<br>EXT2, 1, L3 | CS deficient<br>Hsndst 1 & 2 over-sulfation<br>HS 2OST over-sulfation<br>HS over-polymerization |
| CHA27 + NS1 + Ep + serglycin + EXT2, 1, L3 | Chsy1 | Hsndst 1<br>Epimerase<br>Serglycin<br>EXT2, 1, L3 | CS deficient<br>HS NDST 1 over-sulfation<br>Epimerase over-epimerization<br>HS over-polymerization |
| CHA27 + NS2 + Ep + serglycin + EXT, 1, L3 | Chsy1 | Hsndst 2<br>Epimerase<br>Serglycin<br>EXT2, 1, L3 | CS deficient<br>HS NDST 2 over-sulfation<br>Epimerase over-epimerization<br>HS over-polymerization |
| CHA27 + NS1 + NS2 + Ep + serglycin + EXT2, 1, L3 | Chsy1 | Hsndst 1 & 2<br>Epimerase<br>Serglycin<br>EXT2, 1, L3 | CS deficient<br>HS NDST 1 & 2 over-sulfation<br>Epimerase over-epimerization<br>HS over-polymerization |
| CHA27 + NS1 + 2S + Ep + serglycin + EXT2, 1, L3 | Chsy1 | Hsndst 1<br>Hs2st<br>Epimerase<br>Serglycin<br>EXT2, 1, L3 | CS deficient<br>HS NDST over-sulfation<br>HS 2OST over-sulfation<br>Epimerase over-epimerization<br>HS over-polymerization |
| CHA27 + NS2 + 2S + Ep + serglycin + EXT2, 1, L3 | Chsy1 | Hsndst 2<br>Hs2st<br>Epimerase<br>Serglycin<br>EXT2, 1, L3 | CS deficient<br>Hsndst2 over-sulfation<br>HS 2OST over-sulfation<br>Epimerase over-epimerization<br>HS over-polymerization |
| CHA27 + NS1 + NS2 + 2S + Ep + serglycin + EXT2, 1, L3 | Chsy1 | Hsndst 1 & 2<br>Hs2st<br>Epimerase<br>Serglycin<br>EXT2, 1, L3 | CS deficient<br>Hsndst 1 & 2 over-sulfation<br>HS 2OST over-sulfation<br>Epimerase over-epimerization<br>HS over-polymerization |
| CHA27 + NS1 + 6S + serglycin + EXT2, 1, L3 | Chsy1 | Hsndst 1<br>HS6st 1, 2 or 1 & 2<br>Serglycin<br>EXT2, 1, L3 | CS deficient<br>HS NDST 1 over-sulfation<br>HS 6OST over-sulfation<br>HS over-polymerization |
| CHA27 + NS2 + 6S + serglycin + EXT2, 1, L3 | Chsy1 | Hsndst 2<br>HS6st 1, 2 or 1 & 2<br>Serglycin<br>EXT2, 1, L3 | CS deficient<br>HS NDST 2 over-sulfation<br>HS over-polymerization |

TABLE 4-continued

Cell lines producing modified heparin

| Cell Line ID | Gene KO | Gene KI | Enzymes |
| --- | --- | --- | --- |
| CHA27 + NS1 + NS2 + 6S + serglycin + EXT2, 1, L3 | Chsy1 | Hsndst 1 & 2<br>HS6st 1, 2 or 1 & 2<br>Serglycin<br>EXT2, 1, L3 | CS deficient<br>HS NDST 1 & 2 over-sulfation<br>HS over-polymerization |
| CHA27 + NS1 + 2S + 6S + serglycin + EXT2, 1, L3 | Chsy1 | Hsndst 1<br>HS2st<br>HS6st 1, 2 or 1 & 2<br>Serglycin<br>EXT2, 1, L3 | CS deficient<br>HS NDST over-sulfation<br>HS 2OST over-sulfation<br>HS 6OST over-sulfation<br>HS over-polymerization |
| CHA27 + NS2 + 2S + 6S + serglycin + EXT2, 1, L3 | Chsy1 | Hsndst 2<br>Hs2st<br>HS6st 1, 2 or 1 & 2<br>Serglycin<br>EXT2, 1, L3 | CS deficient<br>Hsndst2 over-sulfation<br>HS 2OST over-sulfation<br>HS over-polymerization |
| CHA27 + NS1 + NS2 + 2S + 6S + serglycin + EXT2, 1, L3 | Chsy1 | Hsndst 1 & 2<br>Hs2st<br>HS6st 1, 2 or 1 & 2<br>Serglycin<br>EXT2, 1, L3 | CS deficient<br>Hsndst 1 & 2 over-sulfation<br>HS 2OST over-sulfation<br>HS over-polymerization |
| CHA27 + NS1 + Ep + serglycin + EXT2, 1, L3 | Chsy1 | Hsndst 1<br>Epimerase<br>HS6st 1, 2 or 1 & 2<br>Serglycin<br>EXT2, 1, L3 | CS deficient<br>HS NDST 1 over-sulfation<br>Epimerase over-epimerization<br>HS over-polymerization |
| CHA27 + NS2 + Ep + 6S + serglycin + EXT2, 1, L3 | Chsy1 | Hsndst 2<br>Epimerase<br>HS6st 1, 2 or 1 & 2<br>Serglycin<br>EXT2, 1, L3 | CS deficient<br>HS NDST 2 over-sulfation<br>Epimerase over-epimerization<br>HS over-polymerization |
| CHA27 + NS1 + NS2 + Ep + 6S + serglycin + EXT2, 1, L3 | Chsy1 | Hsndst 1 & 2<br>Epimerase<br>HS6st 1, 2 or 1 & 2<br>Serglycin<br>EXT2, 1, L3 | CS deficient<br>HS NDST 1 & 2 over-sulfation<br>Epimerase over-epimerization<br>HS over-polymerization |
| CHA27 + NS1 + 2S + Ep + 6S + serglycin + EXT2, 1, L3 | Chsy1 | Hsndst 1<br>Hs2st<br>Epimerase<br>HS6st 1, 2 or 1 & 2<br>Serglycin<br>EXT2, 1, L3 | CS deficient<br>HS NDST over-sulfation<br>HS 2OST over-sulfation<br>Epimerase over-epimerization<br>HS over-polymerization |
| CHA27 + NS2 + 2S + Ep + 6S + serglycin + EXT2, 1, L3 | Chsy1 | Hsndst 2<br>Hs2st<br>Epimerase<br>HS6st 1, 2 or 1 & 2<br>Serglycin<br>EXT2, 1, L3 | CS deficient<br>Hsndst2 over-sulfation<br>HS 2OST over-sulfation<br>Epimerase over-epimerization<br>HS over-polymerization |
| CHA27 + NS1 + NS2 + 2S + Ep + 6S + serglycin + EXT2, 1, L3 | Chsy1 | Hsndst 1 & 2<br>Hs2st<br>Epimerase<br>HS6st 1, 2 or 1 & 2<br>Serglycin<br>EXT2, 1, L3 | CS deficient<br>Hsndst 1 & 2 over-sulfation<br>HS 2OST over-sulfation<br>Epimerase over-epimerization<br>HS 6OST over-sulfation<br>HS over-polymerization |
| CHA27 + NS1 + 3S + serglycin + EXT2, 1, L3 | Chsy1 | Hsndst 1<br>Hs3st<br>Serglycin<br>EXT2, 1, L3 | CS deficient<br>HS NDST 1 over-sulfation<br>HS 3OST over-sulfation<br>HS over-polymerization |
| CHA27 + NS2 + 3S + serglycin + EXT2, 1, L3 | Chsy1 | Hsndst 2<br>Hs3st<br>Serglycin<br>EXT2, 1, L3 | CS deficient<br>HS NDST 2 over-sulfation<br>HS 3OST over-sulfation<br>HS over-polymerization |
| CHA27 + NS1 + NS2 + 3S + serglycin + EXT2, 1, L3 | Chsy1 | Hsndst 1 & 2<br>Hs3st<br>Serglycin<br>EXT2, 1, L3 | CS deficient<br>HS NDST 1 & 2 over-sulfation<br>HS 3OST over-sulfation<br>HS over-polymerization |

TABLE 4-continued

Cell lines producing modified heparin

| Cell Line ID | Gene KO | Gene KI | Enzymes |
|---|---|---|---|
| CHA27 + NS1 + 2S + 3S + serglycin + EXT2, 1, L3 | Chsy1 | Hsndst 1<br>Hs2st<br>Hs3st<br>Serglycin<br>EXT2, 1, L3 | CS deficient<br>HS NDST over-sulfation<br>HS 2OST over-sulfation<br>HS 3OST over-sulfation<br>HS over-polymerization |
| CHA27 + NS2 + 2S + 3S + serglycin + EXT2, 1, L3 | Chsy1 | Hsndst 2<br>Hs2st<br>Hs3st<br>Serglycin<br>EXT2, 1, L3 | CS deficient<br>Hsndst2 over-sulfation<br>HS 2OST over-sulfation<br>HS 3OST over-sulfation<br>HS over-polymerization |
| CHA27 + NS1 + NS2 + 2S + 3S + serglycin + EXT2, 1, L3 | Chsy1 | Hsndst 1 & 2<br>Hs2st<br>Hs3st<br>Serglycin<br>EXT2, 1, L3 | CS deficient<br>Hsndst 1 & 2 over-sulfation<br>HS 2OST over-sulfation<br>HS 3OST over-sulfation<br>HS over-polymerization |
| CHA27 + NS1 + Ep + 3S + serglycin + EXT2, 1, L3 | Chsy1 | Hsndst 1<br>Epimerase<br>Hs3st<br>Serglycin<br>EXT2, 1, L3 | CS deficient<br>HS NDST 1 over-sulfation<br>Epimerase over-epimerization<br>HS 3OST over-sulfation<br>HS over-polymerization |
| CHA27 + NS2 + Ep + 3S + serglycin + EXT2, 1, L3 | Chsy1 | Hsndst 2<br>Epimerase<br>Hs3st<br>Serglycin<br>EXT2, 1, L3 | CS deficient<br>HS NDST 2 over-sulfation<br>Epimerase over-epimerization<br>HS 3OST over-sulfation<br>HS over-polymerization |
| CHA27 + NS1 + NS2 + Ep + 3S + serglycin + EXT2, 1, L3 | Chsy1 | Hsndst 1 & 2<br>Epimerase<br>Hs3st<br>Serglycin<br>EXT2, 1, L3 | CS deficient<br>HS NDST 1 & 2 over-sulfation<br>Epimerase over-epimerization<br>HS 3OST over-sulfation<br>HS over-polymerization |
| CHA27 + NS1 + 2S + Ep + 3S + serglycin + EXT2, 1, L3 | Chsy1 | Hsndst 1<br>Hs2st<br>Epimerase<br>Hs3st<br>Serglycin<br>EXT2, 1, L3 | CS deficient<br>HS NDST over-sulfation<br>HS 2OST over-sulfation<br>Epimerase over-epimerization<br>HS 3OST over-sulfation<br>HS over-polymerization |
| CHA27 + NS2 + 2S + Ep + 3S + serglycin + EXT2, 1, L3 | Chsy1 | Hsndst 2<br>Hs2st<br>Epimerase<br>Hs3st<br>Serglycin<br>EXT2, 1, L3 | CS deficient<br>Hsndst2 over-sulfation<br>HS 2OST over-sulfation<br>Epimerase over-epimerization<br>HS 3OST over-sulfation<br>HS over-polymerization |
| CHA27 + NS1 + NS2 + 2S + Ep + 3S + serglycin + EXT2, 1, L3 | Chsy1 | Hsndst 1 & 2<br>Hs2st<br>Epimerase<br>Hs3st<br>Serglycin<br>EXT2, 1, L3 | CS deficient<br>Hsndst 1 & 2 over-sulfation<br>HS 2OST over-sulfation<br>Epimerase over-epimerization<br>HS 3OST over-sulfation<br>HS over-polymerization |
| CHA27 + NS1 + 6S + 3S + serglycin + EXT2, 1, L3 | Chsy1 | Hsndst 1<br>HS6st 1, 2 or 1 & 2<br>Hs3st<br>Serglycin<br>EXT2, 1, L3 | CS deficient<br>HS NDST 1 over-sulfation<br>HS 6OST over-sulfation<br>HS 3OST over-sulfation<br>HS over-polymerization |
| CHA27 + NS2 + 6S + 3S + serglycin + EXT2, 1, L3 | Chsy1 | Hsndst 2<br>HS6st 1, 2 or 1 & 2<br>Hs3st<br>Serglycin<br>EXT2, 1, L3 | CS deficient<br>HS NDST 2 over-sulfation<br>HS 3OST over-sulfation<br>HS 3OST over-sulfation<br>HS over-polymerization |
| CHA27 + NS1 + NS2 + 6S + 3S + serglycin + EXT2, 1, L3 | Chsy1 | Hsndst 1 & 2<br>HS6st 1, 2 or 1 & 2<br>Hs3st<br>Serglycin<br>EXT2, 1, L3 | CS deficient<br>HS NDST 1 & 2 over-sulfation<br>HS 3OST over-sulfation<br>HS over-polymerization |
| CHA27 + NS1 + 2S + 6S + 3S + serglycin + EXT2, 1, L3 | Chsy1 | Hsndst 1<br>HS2st<br>HS6st 1, 2 or 1 & 2<br>Hs3st<br>Serglycin<br>EXT2, 1, L3 | CS deficient<br>HS NDST over-sulfation<br>HS 2OST over-sulfation<br>HS 6OST over-sulfation<br>HS 3OST over-sulfation<br>HS over-polymerization |

TABLE 4-continued

| Cell lines producing modified heparin | | | |
|---|---|---|---|
| Cell Line ID | Gene KO | Gene KI | Enzymes |
| CHA27 + NS2 + 2S + 6S + 3S + serglycin + EXT2, 1, L3 | Chsy1 | Hsndst 2<br>Hs2st<br>HS6st 1, 2 or 1 & 2<br>Hs3st<br>serglycin<br>EXT2, 1, L3 | CS deficient<br>Hsndst2 over-sulfation<br>HS 2OST over-sulfation<br>HS 3OST over-sulfation<br>HS over-polymerization |
| CHA27 + NS1 + NS2 + 2S + 6S + 3S + serglycin + EXT2, 1, L3 | Chsy1 | Hsndst 1 & 2<br>Hs2st<br>HS6st 1, 2 or 1 & 2<br>Hs3st<br>Serglycin<br>EXT2, 1, L3 | CS deficient<br>Hsndst 1 & 2 over-sulfation<br>HS 2OST over-sulfation<br>HS 3OST over-sulfation<br>HS over-polymerization |
| CHA27 + NS1 + Ep + 3S + serglycin + EXT2, 1, L3 | Chsy1 | Hsndst 1<br>Epimerase<br>HS6st 1, 2 or 1 & 2<br>Hs3st<br>Serglycin<br>EXT2, 1, L3 | CS deficient<br>HS NDST 1 over-sulfation<br>Epimerase over-epimerization<br>HS 3OST over-sulfation<br>HS over-polymerization |
| CHA27 + NS2 + Ep + 6S + 3S + serglycin + EXT2, 1, L3 | Chsy1 | Hsndst 2<br>Epimerase<br>HS6st 1, 2 or 1 & 2<br>Hs3st<br>Serglycin<br>EXT2, 1, L3 | CS deficient<br>HS NDST 2 over-sulfation<br>Epimerase over-epimerization<br>HS 3OST over-sulfation<br>HS over-polymerization |
| CHA27 + NS1 + NS2 + Ep + 6S + 3S + serglycin + EXT2, 1, L3 | Chsy1 | Hsndst 1 & 2<br>Epimerase<br>HS6st 1, 2 or 1 & 2<br>Hs3st<br>Serglycin<br>EXT2, 1, L3 | CS deficient<br>HS NDST 1 & 2 over-sulfation<br>Epimerase over-epimerization<br>HS 3OST over-sulfation<br>HS over-polymerization |
| CHA27 + NS1 + 2S + Ep + 6S + 3S + serglycin + EXT2, 1, L3 | Chsy1 | Hsndst 1<br>Hs2st<br>Epimerase<br>HS6st 1, 2 or 1 & 2<br>Hs3st<br>Serglycin<br>EXT2, 1, L3 | CS deficient<br>HS NDST over-sulfation<br>HS 2OST over-sulfation<br>Epimerase over-epimerization<br>HS 3OST over-sulfation<br>HS over-polymerization |
| CHA27 + NS2 + 2S + Ep + 6S + 3S + serglycin + EXT2, 1, L3 | Chsy1 | Hsndst 2<br>Hs2st<br>Epimerase<br>HS6st 1, 2 or 1 & 2<br>Hs3st<br>Serglycin<br>EXT2, 1, L3 | CS deficient<br>Hsndst2 over-sulfation<br>HS 2OST over-sulfation<br>Epimerase over-epimerization<br>HS 3OST over-sulfation<br>HS over-polymerization |
| CHA27 + NS1 + NS2 + 2S + Ep + 6S + 3S + serglycin + EXT2, 1, L3 | Chsy1 | Hsndst 1 & 2<br>Hs2st<br>Epimerase<br>HS6st 1, 2 or 1 & 2<br>Hs3st<br>Serglycin<br>EXT2, 1, L3 | CS deficient<br>Hsndst 1 & 2 over-sulfation<br>HS 2OST over-sulfation<br>Epimerase over-epimerization<br>HS 6OST over-sulfation<br>HS 3OST over-sulfation<br>HS over-polymerization |

TABLE 5

| Additional Genes for Transgenic and/or Genetically Deficient Cells Lines Producing Modified HS | |
|---|---|
| Gene(s) | Enzyme |
| GUSB | Beta-glucuronidase |
| GALNS | Galactosamine-6 sulfatase |
| IDUA | Alpha-L-iduronidase |
| SGSH | Sulfamidase |
| HGSNAT4 | Glucosamine N-acetyltransferase |
| IDS | Uronate-2-sulfatase |

TABLE 5-continued

| Additional Genes for Transgenic and/or Genetically Deficient Cells Lines Producing Modified HS | |
|---|---|
| Gene(s) | Enzyme |
| NAGLU | Alpha-N-acetylglucosaminidase |
| PAPSS1, PAPSS2 | PAPS synthase |
| XYLT1 | Xylosyltransferase 1 |
| XYLT2 | Xylosyltransferase 2 |
| b4galt7 | Galactosyltransferase 1 |
| b3galt6 | Galactosyltransferase 2 |

TABLE 5-continued

| Additional Genes for Transgenic and/or Genetically Deficient Cells Lines Producing Modified HS | |
|---|---|
| Gene(s) | Enzyme |
| Glcat3 | Glucuronyltransferase 1 |
| EXTL3 | Exostosin-Like Glycosyltransferase 3 |
| EXT1 | Exostosin Glycosyltransferase 1 |
| EXT2 | Exostosin Glycosyltransferase 2 |
| HPSE | Heparanase |
| GPC1 | Glypican 1 |
| GPC2 | Glypican 2 |
| GPC3 | Glypican 3 |
| GPC4 | Glypican 4 |
| GPC5 | Glypican 5 |
| GPC6 | Glypican 6 |
| SDC1 | Syndecan 1 |

TABLE 5-continued

| Additional Genes for Transgenic and/or Genetically Deficient Cells Lines Producing Modified HS | |
|---|---|
| Gene(s) | Enzyme |
| SDC2 | Syndecan 2 |
| SDC3 | Syndecan 3 |
| SDC4 | Syndecan 4 |
| BGCAN/TGFBR3 | Betaglycan |
| CD47 | CD47 |
| CD44V3 | CD44V3 |
| NRP1 | Neuropillin 1 |
| SRGN | Serglycin |
| PLC | Perlecan |
| AGRN | Agrin |
| COL18A1 | Collagen 18 |

TABLE 6

Genes for Transgenic and/or Genetically Deficient Cells Lines Producing Heparin and Hyper-Sulfated Heparan Sulfate

| Gene (Accession Number) | Protein Name | Enzymatic Activity |
|---|---|---|
| SLC26A2 (NP_000103) | DTDST sulfate anion transporter 1 | Transport of sulfate across plasma membrane |
| PAPSS1 (Y10387) | PAPS synthetase-1 (ATP sulfurylase/APS kinase 1) | PAPS formation<br>KI: increase sulfation<br>KO: decrease sulfation |
| PAPSS2 (AF074331) | PAPS synthetase-2 (ATP sulfurylase/APS kinase 2) | PAPS formation<br>KI: increase sulfation<br>KO: decrease sulfation |
| AB107958 | PAPS transporter | Import of PAPS into Golgi<br>KI: increase sulfation<br>KO: decrease sulfation |
| SLC35B2 (Q8TB61.1) | PAPS transporter 1 | Import of PAPS into Golgi<br>KI: increase sulfation<br>KO: decrease sulfation |
| SLC35B3 (Q9H1N7.1) | PAPS transporter 2 | Import of PAPS into Golgi<br>KI: increase sulfation<br>KO: decrease sulfation |
| SLC35D1 (NP_055954) | UDP-GlcA transporter | Import of UDP-GlcA/UDP-GalNAc<br>KI: increase GAG production<br>KO: decrease GAG production |
| SLC35A3 (NP_036375) | UDP-GlcNAc transporter | Import of UDP-GlcNAc<br>KI: increase GAG production<br>KO: decrease GAG production |
| SLC35A2 (P78381) | UDP-Gal transporter | Import of UDP-Gal<br>KI: increase GAG production<br>KO: decrease GAG production |
| UGDH (AAC36095) | UDP glucose dehydrogenase | Conversion of UDP-Glc to UDP-GlcA<br>KI: increase GAG production<br>KO: decrease GAG production |
| UXS (AAK85410) | UDP-glucose decarboxylase | Conversion of UDP-GlcA to UDP-Xyl<br>KI: increase GAG production<br>KO: decrease GAG production |
| XTI (AJ277441) | Xylosyltransferase I | Attachment of Xylose to Ser of core protein<br>KI: increase GAG production<br>KO: decrease GAG production |
| XTII (AJ277442) | Xylosyltransferase II | Attachment of Xylose to Ser of core protein<br>KI: increase GAG production<br>KO: decrease GAG production |
| XGALT-1 (AB028600) | Galactosyltransferase I (β4GalT7) | Addition of Galβ4 to Xylβ4Ser<br>KI: increase GAG production<br>KO: decrease GAG production |
| GALT-2 (AY050570) | Galactosyltransferase II (β3GalT6) | Addition of Galβ3 to Galβ4Xyl<br>KI: increase GAG production<br>KO: decrease GAG production |
| GLCAT-1 (AB009598) | Glucuronosyltransferase I | Addition of GlcAβ3 to Galβ3Galβ4Xyl<br>KI: increase GAG production<br>KO: decrease GAG production |
| EXTL1 (AH007206) | α-N-acetylglucosaminyltransferase I | Addition of GlcNAcα4 to Galβ3Galβ4Xyl<br>KI: increase GAG production<br>KO: decrease GAG production |

TABLE 6-continued

Genes for Transgenic and/or Genetically Deficient Cells Lines Producing Heparin and Hyper-Sulfated Heparan Sulfate

| Gene (Accession Number) | Protein Name | Enzymatic Activity |
|---|---|---|
| EXTL2 (AF000416) | α-N-acetylglucosaminyltransferase I | Addition of GlcNAcα4 to Galβ3Galβ4Xyl<br>KI: increase GAG production<br>KO: decrease GAG production |
| EXTL3 (AF001690) | α-N-acetylglucosaminyltransferase I | Addition of GlcNAcα4 to Galβ3Galβ4Xyl<br>KI: increase GAG production<br>KO: decrease GAG production |
| EXT1 (S79639) | Exostosin glycosyltransferase 1 | GlcNAcα4 & GlcAβ4 transferases: HS copolymerase<br>KI: increase GAG production<br>KO: decrease GAG production |
| EXT2 (NM_000401) | Exostosin glycosyltransferase 2 | GlcNAcα4 & GlcAβ4 transferases: HS copolymerase<br>KI: increase GAG production<br>KO: decrease GAG production |
| NDST1 (U18918) | N-deacetylase N-sulfotransferase 1 | N-deacetylation and N-sulfation of GlcNAc<br>KI: increase N-sulfation<br>KO: decrease N-sulfation |
| NDST2 (NM_003635) | N-deacetylase N-sulfotransferase 2 | N-deacetylation and N-sulfation of GlcNAc<br>KI: increase N-sulfation<br>KO: decrease N-sulfation |
| NDST3 (AF074924) | N-deacetylase N-sulfotransferase 3 | N-deacetylation and N-sulfation of GlcNAc<br>KI: increase N-sulfation<br>KO: decrease N-sulfation |
| NDST4 (AB036429) | N-deacetylase N-sulfotransferase 4 | N-deacetylation and N-sulfation of GlcNAc<br>KI: increase N-sulfation<br>KO: decrease N-sulfation |
| C5EPI (XM_035390) | C5 glucuronyl epimerase | Conversion of D-GlcA to L-IdoA<br>KI: increase epimerization<br>KO: decrease epimerization |
| HS2ST (AB024568) | Heparan sulfate 2-O-sulfotransferase | 2-O-sulfation of IdoA<br>KI: increase 2-O-sulfation<br>KO: decrease 2-O-sulfation |
| HS6ST1 (AB006179) | Heparan sulfate glucosamine 6-O-sulfotransferase 1 | 6-O-sulfation of glucosamine<br>KI: increase 6-O-sulfation<br>KO: decrease 6-O-sulfation |
| HS6ST2 (NM_147174) | Heparan sulfate glucosamine 6-O-sulfotransferase 2 | 6-O-sulfation of glucosamine<br>KI: increase 6-O-sulfation<br>KO: decrease 6-O-sulfation |
| HS6ST2 (NM_147175) | Heparan sulfate glucosamine 6-O-sulfotransferase 2 short | 6-O-sulfation of glucosamine<br>KI: increase 6-O-sulfation<br>KO: decrease 6-O-sulfation |
| HS6ST3 (AF539426) | Heparan sulfate glucosamine 6-O-sulfotransferase 3 | 6-O-sulfation of glucosamine<br>KI: increase 6-O-sulfation<br>KO: decrease 6-O-sulfation |
| HS3ST1 (AF019386) | Heparan sulfate glucosamine 3-O-sulfotransferase 1 | 3-O-sulfation of glucosamine (GlcAGlcNS(±6S)<br>KI: increase 3-O-sulfation<br>KO: decrease 3-O-sulfation |
| HS35T2 (AF105375) | Heparan sulfate glucosamine 3-O-sulfotransferase 2 | 3-O-sulfation of glucosamine in restricted domains<br>KI: increase 3-O-sulfation<br>KO: decrease 3-O-sulfation |
| HS3ST3A1 (AF105376) | Heparan sulfate glucosamine 3-O-sulfotransferase 3A | 3-O-sulfation of glucosamine in restricted domains<br>KI: increase 3-O-sulfation<br>KO: decrease 3-O-sulfation |
| HS3ST3B1 (AF105377) | Heparan sulfate glucosamine 3-O-sulfotransferase 3B | 3-O-sulfation of glucosamine in restricted domains<br>KI: increase 3-O-sulfation<br>KO: decrease 3-O-sulfation |
| HS35T4 (AF105378) | Heparan sulfate glucosamine 3-O-sulfotransferase 4 | 3-O-sulfation of glucosamine in restricted domains |
| HS3ST5 (AF503292) | Heparan sulfate glucosamine 3-O-sulfotransferase 5 | 3-O-sulfation of glucosamine in restricted domains<br>KI: increase 3-O-sulfation<br>KO: decrease 3-O-sulfation |
| HS3ST6 (AE00640) | Heparan sulfate glucosamine 3-O-sulfotransferase 6 | 3-O-sulfation of glucosamine in restricted domains<br>KI: increase 3-O-sulfation<br>KO: decrease 3-O-sulfation |
| Sdc-1 (Hs.82109) | Syndecan-1 | Membrane spanning proteoglycan<br>KI: increase GAG production<br>KO: decrease GAG production |

TABLE 6-continued

Genes for Transgenic and/or Genetically Deficient Cells Lines Producing Heparin and Hyper-Sulfated Heparan Sulfate

| Gene (Accession Number) | Protein Name | Enzymatic Activity |
|---|---|---|
| Sdc-2 (Hs.1501) | Syndecan-2 (fibroglycan) | Membrane spanning proteoglycan<br>KI: increase GAG production<br>KO: decrease GAG production |
| Sdc-3 (Hs.158287) | Syndecan-3 (N-syndecan) | Membrane spanning proteoglycan<br>KI: increase GAG production<br>KO: decrease GAG production |
| Sdc-4 (Hs.252189) | Syndecan-4 (ryudocan, amphiglycan) | Membrane spanning proteoglycan<br>KI: increase GAG production<br>KO: decrease GAG production |
| Gpc-1 (Hs.328232) | Glypican-1 | GPI-anchored membrane proteoglycan<br>KI: increase GAG production<br>KO: decrease GAG production |
| Gpc-2 (Hs.211701) | Glypican-2 (cerebroglycan) | GPI-anchored membrane proteoglycan<br>KI: increase GAG production<br>KO: decrease GAG production |
| Gpc-3 (Hs.119651) | Glypican-3 | GPI-anchored membrane proteoglycan<br>KI: increase GAG production<br>KO: decrease GAG production |
| Gpc-4 (Hs.58367) | Glypican-4 | GPI-anchored membrane proteoglycan<br>KI: increase GAG production<br>KO: decrease GAG production |
| Gpc-5 (Hs.76828) | Glypican-5 | GPI-anchored membrane proteoglycan<br>KI: increase GAG production<br>KO: decrease GAG production |
| Gpc-6 (Hs.118407) | Glypican-6 | GPI-anchored membrane proteoglycan<br>KI: increase GAG production<br>KO: decrease GAG production |
| CD44 (Hs.502328) | CD44 (epican) | Membrane spanning proteoglycan<br>KI: increase GAG production<br>KO: decrease GAG production |
| Prl (Hs.211573) | Perlecan (HSPG2) | Secreted basement membrane proteoglycan<br>KI: increase GAG production<br>KO: decrease GAG production |
| Agrn (Hs.273330) | Agrin | Secreted basement membrane proteoglycan<br>KI: increase GAG production<br>KO: decrease GAG production |
| Sgc (Hs.451015) | Serglycin | Intracellular granule proteoglycan<br>KI: increase GAG production<br>KO: decrease GAG production |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a heparan sulfate, wherein the composition is at least 99.5% free of chondroitin sulfate, wherein the composition is derived from a cell line comprising a genetic deficiency in Heparan sulfate 2-O-sulfotransferase (HS2ST) and chondroitin sulfate synthase 1 (ChSy1) and transgenic for Sulfatase 2 (Sulf2), and wherein the composition has reduced binding to Platelet Factor 4 (PF4), and/or Vascular Endothelial Growth Factor (VEGF) compared with heparin or heparan sulfate isolated from a wildtype Chinese Hamster Ovary (CHO) cell.

2. The composition of claim 1, wherein the composition is purified from a cell line genetically modified to be deficient for or transgenic for one or more genes selected from the group consisting of DTDST sulfate anion transporter 1, PAPS synthetase-1 (ATP sulfurylase/APS kinase 1), PAPS synthetase-2 (ATP sulfurylase/APS kinase 2), PAPS transporter, PAPS transporter 1, PAPS transporter 2, UDP-GlcA transporter, UDP-GlcNAc transporter, UDP-Gal transporter, UDP glucose dehydrogenase, UDP-glucose decarboxylase, Xylosyltransferase I, Xylosyltransferase II, Galactosyltransferase I (β4GalT7), Galactosyltransferase II (03GalT6), Glucuronosyltransferase I, α-N-acetylglucosaminyltransferase I, α-N-acetylglucosaminyltransferase I, α-N-acetylglucosaminyltransferase I, Exostosin glycosyltransferase 1, Exostosin glycosyltransferase 2, N-deacetylase N-sulfotransferase 3, N-deacetylase N-sulfotransferase 4, Heparan sulfate 2-O-sulfotransferase, Heparan sulfate glucosamine 6-O-sulfotransferase 1, Heparan sulfate glucosamine 6-O-sulfotransferase 2, Heparan sulfate glucosamine 6-O-sulfotransferase 2 short, Heparan sulfate glucosamine 6-O-sulfotransferase 3, Heparan sulfate glucosamine 3-O-sulfotransferase 1, Heparan sulfate glucosamine 3-O-sulfotransferase 2, Heparan sulfate glucosamine 3-O-sulfotransferase 3A, Heparan sulfate glucosamine 3-O-sulfotransferase 3B, Heparan sulfate glucosamine 3-O-sulfotransferase 4, Heparan sulfate glucosamine 3-O-sulfotransferase 5, Heparan sulfate glucosamine 3-O-sulfotransferase 6, Syndecan-1, Syndecan-2 (fibroglycan), Syndecan-3 (N-syndecan), Syndecan-4 (ryudocan, amphiglycan), Glypican-1, Glypican-2 (cerebroglycan), Glypican-3, Glypican-4, Glypican-5, Glypican-6, CD44 (epican), Perlecan (HSPG2), Agrin, and Serglycin.

3. The composition of claim 1, wherein the composition is purified from cells that do not produce chondroitin sulfate.

4. The composition of claim 1, wherein the composition is purified from a cell line genetically modified to be transgenic for Hs3st1.

5. The composition of claim 1, wherein the composition comprises a heparan sulfate with a defined pattern of sulfation compared with a heparan sulfate isolated from a wild-type CHO cell.

6. The composition of claim 1, wherein the composition is at least 95% free of protein and nucleic acid contamination.

7. The composition of claim 1, wherein the composition is at least 95% heparan sulfate.

8. A pharmaceutical composition comprising the composition of claim 1 and a pharmaceutically acceptable carrier or excipient.

* * * * *